(12) United States Patent
Kerns et al.

(10) Patent No.: US 12,091,650 B2
(45) Date of Patent: Sep. 17, 2024

(54) DEVELOPMENT OF SPINAL CORD ON A MICROFLUIDIC CHIP

(71) Applicants: EMULATE, INC., Boston, MA (US); CEDARS-SINAI MEDICAL CENTER, Los Angeles, CA (US)

(72) Inventors: S. Jordan Kerns, Reading, MA (US); Norman Wen, West Roxbury, MA (US); Carolina Lucchesi, Westwood, MA (US); Christopher David Hinojosa, Malden, MA (US); Jacob Fraser, Somerville, MA (US); Geraldine Hamilton, Boston, MA (US); Gad Vatine, Los Angeles, CA (US); Samuel Sances, Santa Monica, CA (US); Clive Svendsen, Pacific Palisades, CA (US); Daniel Levner, Brookline, MA (US); Dhruv Sareen, Porter Ranch, CA (US)

(73) Assignee: EMULATE, INC., Boston, MA (US)

( * ) Notice: Subject to any disclaimer, the term of this patent is extended or adjusted under 35 U.S.C. 154(b) by 709 days.

(21) Appl. No.: 16/286,185

(22) Filed: Feb. 26, 2019

(65) Prior Publication Data

US 2019/0359924 A1 Nov. 28, 2019

Related U.S. Application Data

(63) Continuation of application No. PCT/US2017/049115, filed on Aug. 29, 2017, which is a continuation-in-part of application No. 15/352,289, filed on Nov. 15, 2016, which is a continuation of application No. PCT/US2016/057724, filed on Oct. 19, 2016.

(60) Provisional application No. 62/380,780, filed on Aug. 29, 2016.

(51) Int. Cl.
| | |
|---|---|
| *C12N 5/0793* | (2010.01) |
| *B01L 3/00* | (2006.01) |
| *C12M 1/12* | (2006.01) |
| *C12M 3/06* | (2006.01) |
| *C12N 5/00* | (2006.01) |
| *C12N 5/071* | (2010.01) |
| *C12N 5/079* | (2010.01) |

(52) U.S. Cl.
CPC ....... *C12M 23/16* (2013.01); *B01L 3/502715* (2013.01); *C12M 25/02* (2013.01); *C12N 5/0068* (2013.01); *C12N 5/0619* (2013.01); *C12N 5/0622* (2013.01); *C12N 5/069* (2013.01); *B01L 2200/0647* (2013.01); *B01L 2300/0861* (2013.01); *C12N 2502/081* (2013.01); *C12N 2502/28* (2013.01); *C12N 2506/02* (2013.01); *C12N 2506/45* (2013.01); *C12N 2531/00* (2013.01); *C12N 2539/00* (2013.01)

(58) Field of Classification Search
None
See application file for complete search history.

(56) References Cited

U.S. PATENT DOCUMENTS

| 8,647,861 | B2 | 2/2014 | Ingber et al. | 435/289.1 |
|---|---|---|---|---|
| 2007/0077649 | A1 | 4/2007 | Sammak et al. | 435/325 |
| 2008/0044847 | A1 | 2/2008 | Shusta et al. | 435/29 |
| 2008/0305086 | A1 * | 12/2008 | Poole | C12N 5/0623 |
| | | | | 424/93.7 |
| 2012/0171354 | A1 | 7/2012 | O'Neill et al. | 427/2.25 |
| 2012/0211373 | A1 | 8/2012 | El-Sayed et al. | 205/778 |
| 2014/0065660 | A1 | 3/2014 | Kim et al. | 435/297.2 |
| 2014/0134732 | A1 * | 5/2014 | Ashton | C12N 5/0619 |
| | | | | 435/377 |
| 2014/0142370 | A1 | 5/2014 | Wong et al. | 600/36 |

FOREIGN PATENT DOCUMENTS

| GB | 2561312 A | 10/2018 | |
|---|---|---|---|
| WO | WO-2015138032 A2 * | 9/2015 | B01L 3/5027 |
| WO | WO-2015181253 A1 * | 12/2015 | C12N 5/0619 |
| WO | WO/2017/070224 | 4/2017 | |
| WO | WO/2017/143049 | 8/2017 | |

OTHER PUBLICATIONS

Demers et al. "Development-on-chip: in vitro neural tube patterning with a microfluidic device." Development 143.11 (2016): 1884-1892. (Year: 2016).*
Uzel et al. "Microfluidic device for the formation of optically excitable, three-dimensional, compartmentalized motor units." Science Advances 2.8 (2016): e1501429 (Year: 2016).*
Sances et al. "Modeling ALS with motor neurons derived from human induced pluripotent stem cells." Nature Neuroscience 19.4 (2016): 542-553. (Year: 2016).*
Southam et al. "A Novel in Vitro Primary Culture Model of the Lower Motor Neuron-Neuromuscular Junction Circuit." Microfluidic and Compartmentalized Platforms for Neurobiological Research. Humana Press, New York, NY, 2015. 181-193. (Year: 2015).*
James et al. "Neuronal action on the developing blood vessel pattern." Seminars in Cell & Developmental Biology. vol. 22. No. 9. Academic Press, 2011. (Year: 2011).*
Ashton, R. et al. (2015) "Chemically defined differentiation of human pluripotent stem cells to hindbrain and spinal cord neural stem cells with defined regional identities," *Protocol Exchange*, 1-23.
Bhatia, S. N. et al. (2014) "Microfluidic organs-on-chips," *Nature Biotechnology* 32(8), 760-772.

(Continued)

*Primary Examiner* — Emily A Cordas
(74) *Attorney, Agent, or Firm* — Medlen & Carroll, LLP

(57) ABSTRACT

The invention relates to culturing brain endothelial cells, and optionally astrocytes and neurons in a fluidic device under conditions whereby the cells mimic the structure and function of the blood brain barrier. Culture of such cells in a microfluidic device, whether alone or in combination with other cells, drives maturation and/or differentiation further than existing systems.

20 Claims, 73 Drawing Sheets
(29 of 73 Drawing Sheet(s) Filed in Color)

(56) References Cited

OTHER PUBLICATIONS

Borghese, L. et al. (2010) "Inhibition of notch signaling in human embryonic stem cell-derived neural stem cells delays G1/S phase transition and accelerates neuronal differentiation in vitro and in vivo," *Stem Cells* 28(5), 955-964.
Brown, J. A. et al. (2015) "Recreating blood-brain barrier physiology and structure on chip: A novel neurovascular microfluidic bioreactor," *Biomicrofluidics* 9(5), 054124-054124.
Christopherson, K. S. et al. (2005) "Thrombospondins Are Astrocyte-Secreted Proteins that Promote CNS Synaptogenesis," *Cell* 120(3), 421-433.
Daneman, R. et al. (2010) "Pericytes are required for blood-brain barrier integrity during embryogenesis," *Nature* 468, 562.
Demestre, M. et al. (2015) "Formation and characterisation of neuromuscular junctions between hiPSC derived motoneurons and myotubes," *Stem Cell Research* 15(2), 328-336.
Dhumpa, R. et al. (2012) "Temporal gradients in microfluidic systems to probe cellular dynamics: a review," *Analytica Chimica Acta* 743, 9-18.
Domenech, M. et al. (2009) "Cellular observations enabled by microculture: paracrine signaling and population demographics," *Integrative Biology* 1(3), 267-274.
Douville, N. J. et al. (2010) "Fabrication of Two-Layered Channel System with Embedded Electrodes to Measure Resistance Across Epithelial and Endothelial Barriers," *Analytical Chemistry* 82(6), 2505-2511.
Du, Z.-W. et al. (2015) "Generation and expansion of highly pure motor neuron progenitors from human pluripotent stem cells," *Nature Communications* 6, 6626.
Ebert, A. D. et al. (2013) "EZ spheres: A stable and expandable culture system for the generation of pre-rosette multipotent stem cells from human ESCs and iPSCs," *Stem Cell Research* 10(3), 417-427.
Engelhardt, B. et al. (2014) "Novel insights into the development and maintenance of the blood-brain barrier," *Cell and Tissue Research* 355(3), 687-699.
Ericson, J. et al. (1997) "Pax6 Controls Progenitor Cell Identity and Neuronal Fate in Response to Graded Shh Signaling," *Cell* 90(1), 169-180.
Ferriero, D. M. et al. (1994) "Somatostatin enhances nerve growth factor-induced neurite outgrowth in PC12 cells," *Developmental Brain Research* 80(1), 13-18.
Gross, P. G. et al. (2007) "Applications of microfluidics for neuronal studies," *Journal of the Neurological Sciences* 252, 135-143.
Gu, C. et al. (2013) "The role of semaphorins and their receptors in vascular development and cancer," *Experimental Cell Research* 319(9), 1306-1316.
Guo, J. H. et al. (2015) "Expression pattern of NeuN and GFAP during human fetal spinal cord development," *Child's Nervous System* 31(6), 863-872.
Hesselmans, L. F. G. M. et al. (1993) "Development of innervation of skeletal muscle fibers in man: Relation to acetylcholine receptors," *The Anatomical Record* 236(3), 553-562.
Ho, R. et al. (2015) "ALS disrupts spinal motor neuron maturation and aging pathways within gene co-expression networks," *Nature Neuroscience* 19, 1256.
Huang, D. W. et al. (2008) "Systematic and integrative analysis of large gene lists using DAVID bioinformatics resources," *Nature Protocols* 4, 44.
Kaupmann, K. et al. (1993) "Distribution and second messenger coupling of four somatostatin receptor subtypes expressed in brain," *FEBS Letters* 331(1-2), 53-59.
Kilic, O. et al. (2016) "Brain-on-a-chip model enables analysis of human neuronal differentiation and chemotaxis," *Lab on a Chip* 16(21), 4152-4162.
Kim, T. et al. (2007) "Arterial versus total blood volume changes during neural activity-induced cerebral blood flow change: implication for BOLD fMRI," *Journal of Cerebral Blood Flow & Metabolism* 27(6), 1235-1247.
Kirkby, L. A. et al. (2013) "A role for correlated spontaneous activity in the assembly of neural circuits," *Neuron* 80(5), 1129-1144.
Kurz, H. (2009) "Cell lineages and early patterns of embryonic CNS vascularization," *Cell Adhesion & Migration* 3 (2), 205-210.
Lacar, B. et al. (2016) "Nuclear RNA-seq of single neurons reveals molecular signatures of activation," *Nature Communications* 7, 11022.
Lee, N. V. et al. (2006) "ADAMTSI mediates the release of antiangiogenic polypeptides from TSP1 and 2," *The EMBO Journal* 25(22), 5270-5283.
Lin, H. J. et al. (2004) "Neural stem cell differentiation in a cell—collagen-bioreactor culture system," *Developmental Brain Research* 153(2), 163-173.
Lippmann, E. S. et al. (2014) "A retinoic acid-enhanced, multicellular human blood-brain barrier model derived from stem cell sources," *Scientific Reports* 4, 4160.
Lippmann, E. S. et al. (2012) "Human Blood-Brain Barrier Endothelial Cells Derived from Pluripotent Stem Cells," *Nature Biotechnology* 30(8), 783-791.
Lukaszewicz, A. I. et al. (2011) "Cyclin D1 promotes neurogenesis in the developing spinal cord in a cell cycle-independent manner," *Proceedings of the National Academy of Sciences of the United States of America* 108(28), 11632-11637.
Maury, Y. et al. (2014) "Combinatorial analysis of developmental cues efficiently converts human pluripotent stem cells into multiple neuronal subtypes," *Nature Biotechnology* 33, 89.
Montoya, J. V. et al. (2009) "Muscle-conditioned media and cAMP promote survival and neurite outgrowth of adult spinal cord motor neurons," *Experimental Neurology* 220(2), 303-315.
Moody, W. J. et al. (2005) "Ion Channel Development, Spontaneous Activity, and Activity-Dependent Development in Nerve and Muscle Cells," *Physiological Reviews* 85(3), 883-941.
Niego, B. e. et al. (2013) "Improved Method for the Preparation of a Human Cell-based, Contact Model of the Blood-Brain Barrier," *Journal of Visualized Experiments*(81), 50934.
O'Rourke, J. G. et al. (2016) "C90rf72 is required for proper macrophage and microglial function in mice," *Science* 351(6279), 1324.
Okita, K. et al. (2011) "A more efficient method to generate integration-free human iPS cells," *Nature Methods* 8(5), 409-412.
Palmer, T. D. et al. (2000) "Vascular niche for adult hippocampal neurogenesis," *Journal of Comparative Neurology* 425(4), 479-494.
Pasterkamp, R. J. (2012) "Getting neural circuits into shape with semaphorins," *Nature Reviews Neuroscience* 13, 605.
Persson, M. et al. (2002) "Dorsal-ventral patterning of the spinal cord requires Gli3 transcriptional repressor activity," *Genes & Development* 16(22), 2865-2878.
Pfaff, S. L. et al. (1996) "Requirement for LIM Homeobox Gene Isll in Motor Neuron Generation Reveals a Motor Neuron-Dependent Step in Interneuron Differentiation," *Cell* 84(2), 309-320.
Przybyla, L. et al. (2012) "Probing Embryonic Stem Cell Autocrine and Paracrine Signaling Using Microfluidics," *Annual Review of Analytical Chemistry* 5(1), 293-315.
Rezaie, P. et al. (1999) "Colonisation of the developing human brain and spinal cord by microglia: a review," *Microscopy Research and Technique* 45(6), 359-382.
Rosenberg, S. S. et al. (2011) "Calcium Signaling in Neuronal Development," *Cold Spring Harbor Perspectives in Biology* 3(10).
Rushton, D. J. et al. (2013) "Stimulation of GABA-Induced Ca2+ Influx Enhances Maturation of Human Induced Pluripotent Stem Cell-Derived Neurons," *PLoS One* 8(11), e81031.
Sareen, D. et al. (2014) "Human neural progenitor cells generated from induced pluripotent stem cells can survive, migrate, and integrate in the rodent spinal cord," *Journal of Comparative Neurology* 522(12), 2707-2728.
Sareen, D. et al. (2013) "Targeting RNA foci in iPSC-derived motor neurons from ALS patients with C9ORF72 repeat expansion," *Science Translational Medicine* 5(208), 208ra149-208ra149.
Sasaki, M. et al. (2001) "A disintegrin and metalloprotease with thrombospondin type 1 motifs (ADAMTS-1) and IL-1 receptor type

(56) References Cited

OTHER PUBLICATIONS 1 mRNAs are simultaneously induced in nerve injured motor neurons," *Brain Research. Molecular Brain Research* 89(1-2), 158-163.
Schweitzer, J. et al. (2005) "Tenascin-C is involved in motor axon outgrowth in the trunk of developing zebrafish," *Developmental Dynamics* 234(3), 550-566.
Tuncdemir, Sebnem N. et al. (2016) "Early Somatostatin Interneuron Connectivity Mediates the Maturation of Deep Layer Cortical Circuits," *Neuron* 89(3), 521-535.
Varnum-Finney, B. et al. (1995) "The integrin receptor alpha 8 beta 1 mediates interactions of embryonic chick motor and sensory neurons with tenascin-C," *Neuron* 14(6), 1213-1222.
Wälchli, T. et al. (2015) "Wiring the Vascular Network with Neural Cues: A CNS Perspective," *Neuron* 87(2), 271-296.
Watson, P. M. D. et al. (2013) "Modelling the endothelial blood-CNS barriers: a method for the production of robust in vitromodels of the rat blood-brain barrier and blood-spinal cord barrier," *BMC Neuroscience* 14(1), 59.
wikipedia.com. Gel—Wikipedia (https://en.wikipedia.org/wiki/Gel).
Yamamoto, K. et al. (2005) "Fluid shear stress induces differentiation of Flk-1-positive embryonic stem cells into vascular endothelial cells in vitro," *American Journal of Physiology-Heart and Circulatory Physiology* 288(4), H1915-H1924.
Yu, H. et al. (2007) "Understanding microchannel culture: parameters involved in soluble factor signaling," *Lab on a Chip* 7(6), 726-730.
Zacchigna, S. et al. (2008) "Neurovascular signalling defects in neurodegeneration," *Nature Reviews Neuroscience* 9, 169.
Zilio, C. et al. (2014) "Erratum to: Universal hydrophilic coating of thermoplastic polymers currently used in microfluidics," *Biomedical Microdevices* 16(3), 499-499.
PCT International Search Report of International Application No. PCT/US2017/049115 dated Nov. 28, 2017.
PCT International Search Report of International Application No. PCT/US2016/057724 dated Jan. 9, 2017.
Ross Hunter Booth, "A microfluidic in vitro model of the blood-brain barrier", Dissertation, US, (Dec. 1, 2014), pp. 1-177.
Achyuta, A. K. et al. (2013) "A modular approach to create a neurovascular unit-on-a-chip," *Lab on a Chip* 13(4), 542-553.
Adriani, G. et al. (2015) "Modeling the Blood-Brain Barrier in a 3D triple co-culture microfluidic system," *Conference proceedings—IEEE Engineering in Medicine and Biology Society* 2015, 338-341.
Hu, B.-Y. et al. (2009) "Differentiation of spinal motor neurons from pluripotent human stem cells," *Nature Protocols* 4(9), 1295-1304.
Huh, D. et al. (2013) "Microfabrication of human organs-on-chips," *Nature Protocols* 8(11), 2135-2157.
Lippmann, E. S. et al. (2014) "A retinoic acid-enhanced, multicellular human blood-brain barrier model derived from stem cell sources," *Scientific Reports* 4, Article No. 4160.
Prabhakarpandian, B. et al. (2013) "SyM-BBB: a microfluidic Blood Brain Barrier model," *Lab on a chip* 13(6), 1093-1101.
Canadian Search Report for Application No. 3034614 dated May 3, 2021, Document not provided.
Australian Search Report for Application No. 2017319168 dated Aug. 18, 2020.
Great Britain Examiner's Report for Application No. GB1904049.2 dated Aug. 26, 202.
European Search Report for Application No. 17847365.8 dated Jun. 25, 2021.

\* cited by examiner

FLUORESCEIN SODIUM
Mw: 376.27 g/mol

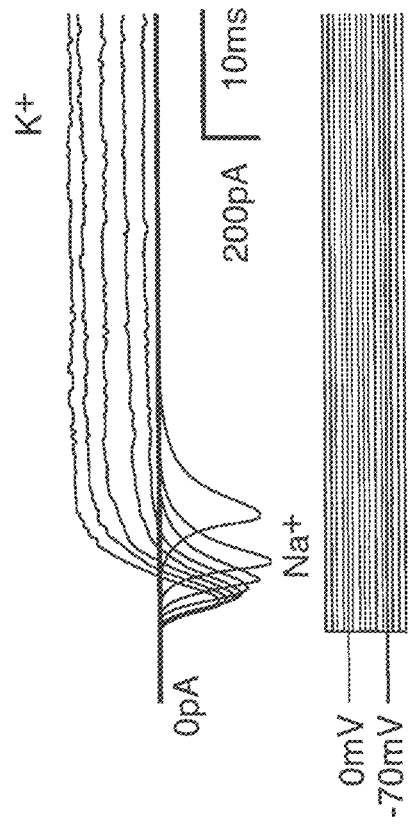
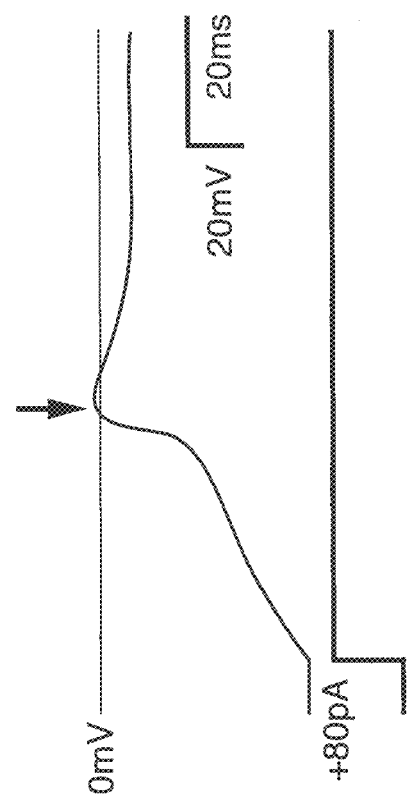
FIG. 18B
FIG. 18A

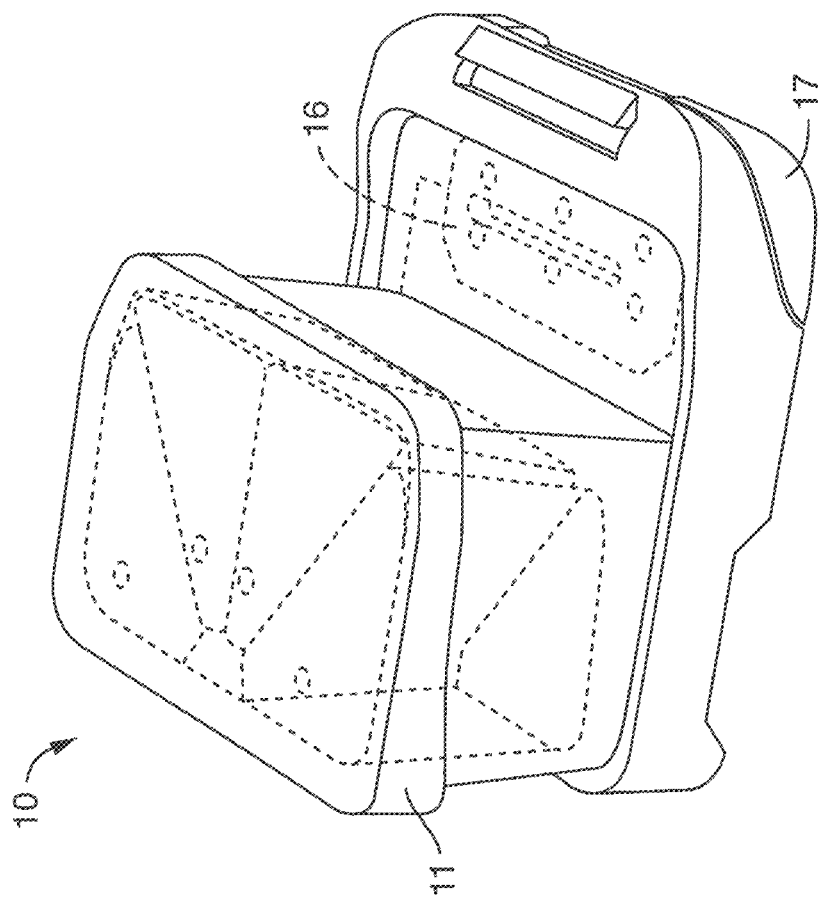
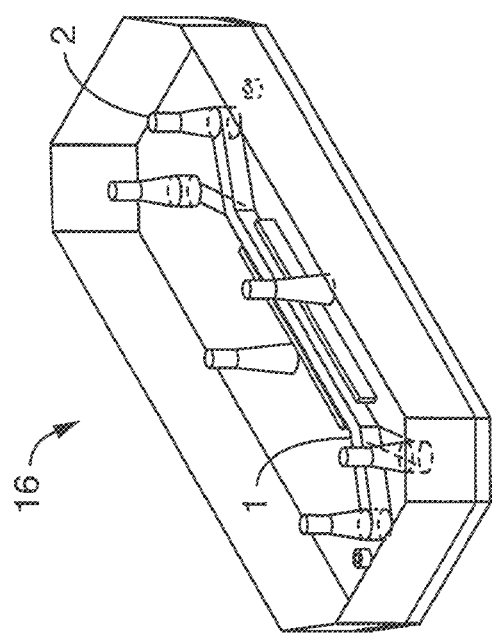
FIG. 22B
FIG. 22A

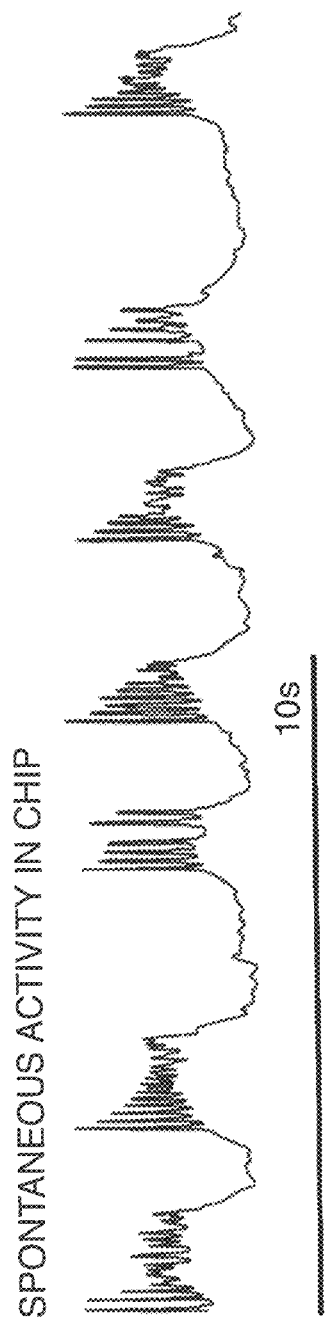
FIG. 24
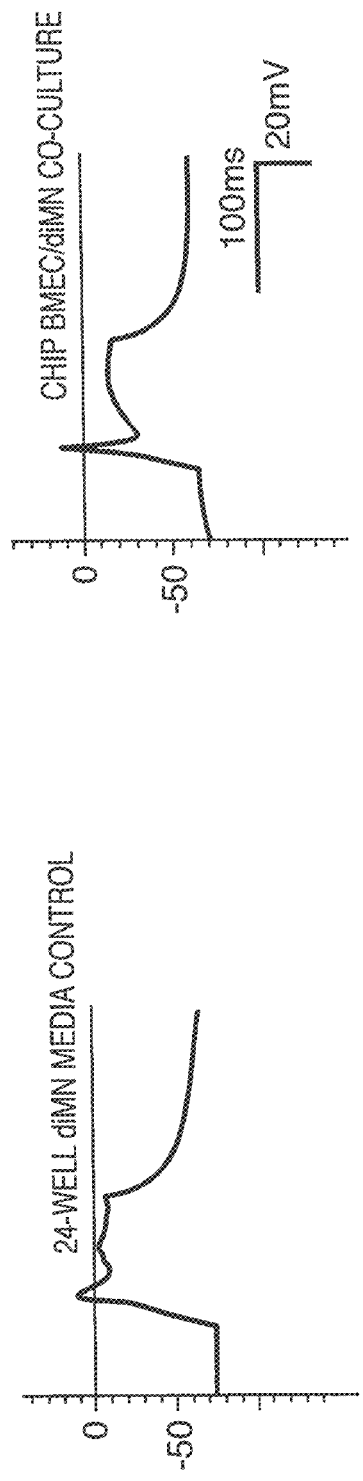
FIG. 25A
FIG. 25B

N = 3 (40-50 NEURONS EA.)

CTRL 96

ECCM 96

MN CHIP

MN/BMEC CHIP

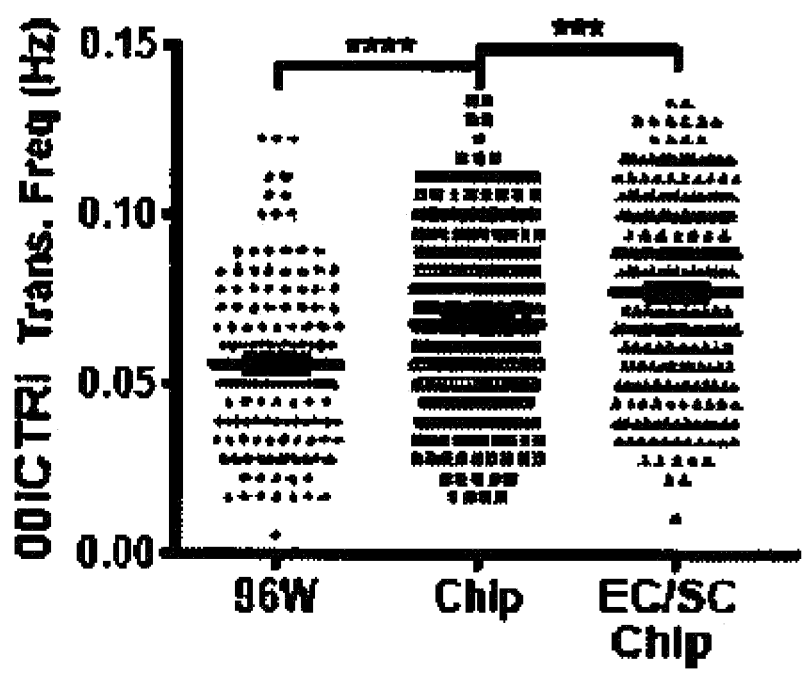

| f | 96W | | | 96CM | | | SC-Chip | | | EC/SC-Chip | | | |
|---|---|---|---|---|---|---|---|---|---|---|---|---|---|
| CCND1 | 23 | 23 | 21 | 26 | 26 | 25 | 46 | 42 | 33 | 66 | 60 | 55 | Response to Stimulus |
| EGR1 | 3.6 | 3.5 | 3.3 | 4.6 | 5.1 | 4.7 | 15 | 8.2 | 8.1 | 11 | 7.4 | 8 | |
| ID1 | 3.8 | 3.8 | 4.5 | 2.3 | 2.4 | 3.1 | 4.4 | 6.4 | 5.4 | 8.3 | 10 | 9.7 | |
| ID2 | 3.9 | 1.6 | 3.8 | 2.5 | 3.1 | 2.5 | 9.4 | 12 | 8.7 | 23 | 22 | 20 | |
| ID3 | 3.2 | 3.7 | 2.1 | 2.3 | 2.6 | 2.3 | 7.5 | 7.3 | 6.8 | 18 | 19 | 18 | |
| ITGA2 | 1.2 | 1.6 | 1.6 | 1.1 | 1.2 | 0.9 | 2.6 | 2.5 | 3 | 2.9 | 3.2 | 3.1 | |
| PCSK1 | 0.1 | 0.1 | 0.1 | 0.2 | 0.2 | 0.2 | 1.5 | 0.9 | 1.1 | 1.3 | 1.3 | 1.1 | |
| MSX1 | 0.2 | 0.3 | 0 | 0.2 | 0.3 | 0.3 | 0.4 | 0.1 | 0.1 | 2.2 | 4.4 | 6.5 | |
| MSX2 | 0.1 | 0.3 | 0.2 | 0.1 | 0 | 0.1 | 0.3 | -0 | 0 | 6.6 | 7.9 | 11 | |

FIG. 35F

| | | | | | | | | | | | | | |
|---|---|---|---|---|---|---|---|---|---|---|---|---|---|
| GLI2 | 1.7 | 1.9 | 1.9 | 2.1 | 2.3 | 2.6 | 4.9 | 4.2 | 3.1 | 4 | 3.6 | 2.9 | Neuron Differentiation |
| GLI3 | 6.2 | 7.3 | 7 | 6 | 6.5 | 5.5 | 12 | 9.5 | 8.9 | 12 | 11 | 13 | |
| ISL1 | 1.5 | 1.1 | 1.1 | 0.6 | 0.9 | 0.6 | 1.1 | 2.5 | 2.9 | 2.5 | 2.3 | 2.4 | |
| SOX5 | 4.6 | 3.7 | 4.3 | 4.7 | 4.9 | 3.9 | 9.3 | 9.6 | 8.8 | 5.9 | 6.7 | 5.6 | |
| HOXA2 | 11 | 12 | 11 | 10 | 9.8 | 9.5 | 21 | 20 | 20 | 16 | 16 | 17 | |
| IRX5 | 1.1 | 1.4 | 1.5 | 1.4 | 1.3 | 1.2 | 3 | 3 | 3.3 | 3 | 2.6 | 2.5 | |
| JAG1 | 5.5 | 5.2 | 6 | 5.3 | 6 | 5.7 | 17 | 16 | 14 | 9.1 | 7.8 | 6.5 | |
| PAX6 | 3.8 | 4.4 | 3.9 | 3.4 | 3.5 | 3.6 | 9.2 | 11 | 9.2 | 7.1 | 5.9 | 5.3 | |
| SLC1A3 | 1.9 | 1.9 | 2.2 | 1.9 | 2.2 | 1.5 | 5.7 | 3.8 | 3.6 | 3.6 | 4 | 4.7 | |
| S1PR1 | 1.7 | 3.4 | 2.8 | 1.9 | 2 | 2 | 5 | 5.8 | 4.8 | 4 | 4.1 | 3 | |
| VSX1 | 1.5 | 1.2 | 1.5 | 1 | 1.1 | 1.1 | 4 | 2.9 | 4.2 | 1.6 | 1.5 | 1.6 | |

-2.0 ▨ RPKM ▨ +2.0  Z-Score

FIG. 35G

| h | 96W | | | 96CM | | | SC-Chip | | | EC/SC-Chip | | | Vascular Development |
|---|---|---|---|---|---|---|---|---|---|---|---|---|---|
| B4GALT1 | 1.9 | 1.4 | 1.8 | 2 | 2.1 | 2.4 | 1.4 | 2.5 | 1.3 | 3.4 | 4.1 | 3.6 | |
| ANXA2 | 21 | 17 | 15 | 14 | 20 | 16 | 11 | 13 | 16 | 40 | 50 | 47 | |
| CAV1 | 0.5 | 0.6 | 0.2 | 0.3 | 0.6 | 0.3 | 0.4 | 0.3 | 0.6 | 1.1 | 1.4 | 1.4 | |
| CXCR4 | 16 | 16 | 14 | 13 | 12 | 15 | 8.3 | 10 | 15 | 22 | 26 | 24 | |
| CTGF | 22 | 15 | 13 | 17 | 26 | 17 | 30 | 25 | 30 | 46 | 54 | 43 | |
| CYR61 | 10 | 7.9 | 6.1 | 9.6 | 16 | 9.6 | 9.1 | 7.9 | 10 | 30 | 27 | 23 | |
| EFNB2 | 8.7 | 6.5 | 5.4 | 5.6 | 7.7 | 6.8 | 5 | 5.2 | 9.1 | 13 | 16 | 14 | |
| HEY1 | 1.9 | 1.8 | 2 | 1.4 | 1.5 | 1.8 | 1.2 | 2.3 | 1.9 | 3.5 | 5 | 2.9 | |
| KDR | 0.7 | 0.4 | 0.3 | 0.4 | 0.9 | 0.6 | 0.3 | 0.2 | 0.3 | 1.2 | 1.3 | 1.3 | |
| SEMA3A | 1.7 | 1.7 | 1.3 | 1.5 | 2 | 1.5 | 2.2 | 2 | 2.3 | 4.1 | 5 | 4.8 | |
| SEMA5A | 0.6 | 0.5 | 0.6 | 0.8 | 0.9 | 0.6 | 1.1 | 0.8 | 0.7 | 3.1 | 3.6 | 5.1 | |

FIG. 35H

| | | | | | | | | | | | | | |
|---|---|---|---|---|---|---|---|---|---|---|---|---|---|
| ADAMTS1 | 0.9 | 1.2 | 1.3 | 1.4 | 1.6 | 1.4 | 1.4 | 0.9 | 0.8 | 2.7 | 3.3 | 2.4 | F |
| ADAMTS18 | 0.2 | 0.3 | 0.1 | 0.2 | 0.2 | 0.3 | 0.1 | 0.1 | 0.1 | 2.2 | 3.1 | 2.2 | |
| MAMDC2 | 0.6 | 0.2 | 0.2 | 0.2 | 0.5 | 0.2 | 0.3 | 0.3 | 0.8 | 1.9 | 1.6 | 1.3 | |
| ANXA2 | 21 | 17 | 15 | 14 | 20 | 16 | 11 | 13 | 16 | 40 | 50 | 47 | |
| COL5A2 | 10 | 12 | 11 | 10 | 12 | 9.3 | 8.1 | 8.4 | 8.5 | 19 | 25 | 20 | |
| COL12A1 | 0.6 | 0.4 | 0.3 | 0.5 | 1 | 0.5 | 0.4 | 0.4 | 0.5 | 1.5 | 1.2 | 1.6 | |
| COL14A1 | 0.9 | 0.4 | 0.5 | 0.5 | 1 | 0.6 | 1 | 0.9 | 1 | 7.6 | 12 | 8.5 | |
| CTGF | 22 | 15 | 13 | 17 | 26 | 17 | 30 | 25 | 30 | 46 | 54 | 43 | Extracellular Matrix |
| FN1 | 6.3 | 6.8 | 6.7 | 5.8 | 8.3 | 6.1 | 3.6 | 3.6 | 3.7 | 11 | 13 | 10 | |
| FLRT3 | 1.7 | 1.6 | 1.5 | 1.2 | 1.9 | 1.8 | 1.2 | 1.6 | 1.8 | 2.8 | 3.4 | 3.4 | |
| LAMB1 | 2.9 | 2.7 | 2.5 | 2.5 | 3.4 | 2.4 | 1.5 | 1.5 | 1.9 | 5.3 | 6.4 | 6.1 | |
| MATN2 | 0.6 | 0.4 | 0.4 | 0.6 | 0.8 | 0.5 | 0.2 | 0.4 | 0.5 | 1.6 | 1.1 | 1.4 | |
| POSTN | 1.1 | 0.8 | 0.4 | 0.4 | 1.3 | 0.6 | 0.1 | 0.3 | 0.5 | 1.8 | 3.1 | 3 | |
| SPARC | 28 | 27 | 27 | 24 | 31 | 26 | 21 | 22 | 21 | 45 | 58 | 51 | |
| SPINT2 | 0.8 | 1.8 | 1.1 | 1 | 1.1 | 0.8 | 0.9 | 0.3 | 1.1 | 2.9 | 2.4 | 3.1 | |
| TNC | 1.4 | 0.5 | 0.9 | 0.9 | 1.5 | 0.7 | 0.5 | 0.5 | 0.5 | 2.5 | 3 | 2.2 | |
| THBS1 | 1.1 | 0.9 | 0.6 | 0.8 | 1.3 | 0.9 | 0.9 | 1.1 | 1.1 | 2.7 | 3 | 3.4 | |
| WNT4 | 0.3 | 0.5 | 0.4 | 0.9 | 0.7 | 0.7 | 0.5 | 0.8 | 0.6 | 1.5 | 2.2 | 2.5 | |

FIG. 35I

FIG. 38C
| | 96W | | | 96CM | | | SC-Chip | | | EC/SC-Chip | | | |
|---|---|---|---|---|---|---|---|---|---|---|---|---|---|
| DLK1 | 1 | 1.9 | 1.6 | 2.3 | 2 | 2.2 | 1.3 | 2.8 | 1.8 | 8.1 | 11 | 10 | Notch Ligand |
| JAG1 | 5.5 | 5.2 | 6 | 5.3 | 6 | 5.7 | 17 | 16 | 14 | 9.1 | 7.8 | 6.5 | |
| DLL1 | 5.1 | 4.8 | 5.3 | 4.3 | 3.9 | 3.6 | 5.6 | 5.6 | 5.4 | 3.3 | 3.2 | 2.9 | |
| DLL3 | 16 | 14 | 12 | 11 | 10 | 11 | 6.7 | 5.5 | 5.1 | 4.6 | 3.3 | 4.1 | |
| DLL4 | 1.1 | 1.3 | 0.9 | 1.1 | 0.7 | 1.1 | 0.7 | 0.5 | 0.4 | 0.7 | 0.5 | 0.4 | |
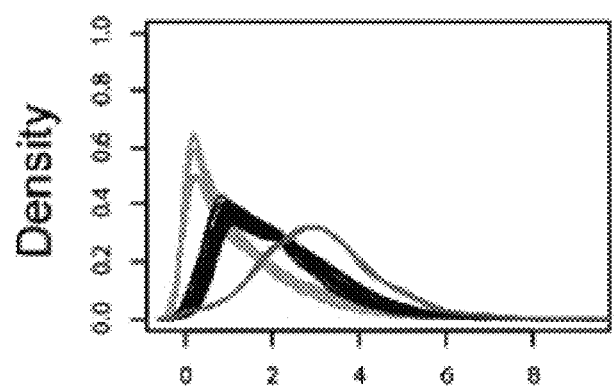
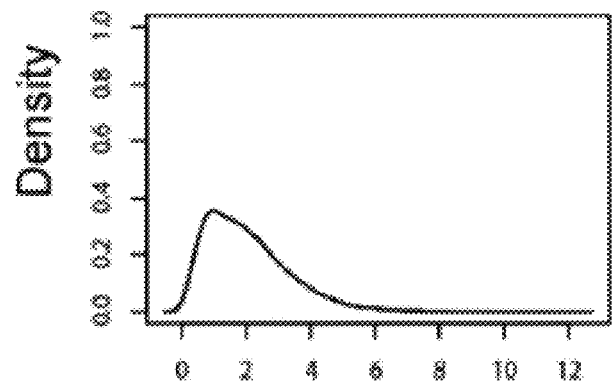
FIG. 39A
N = 9835 Bandwidth = 0.1822

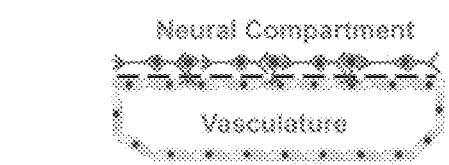
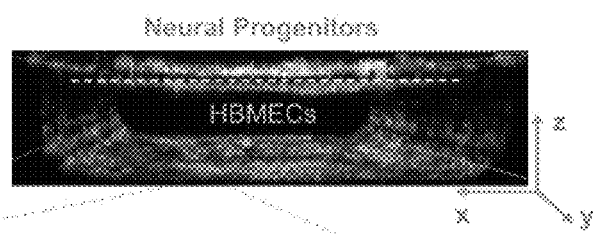
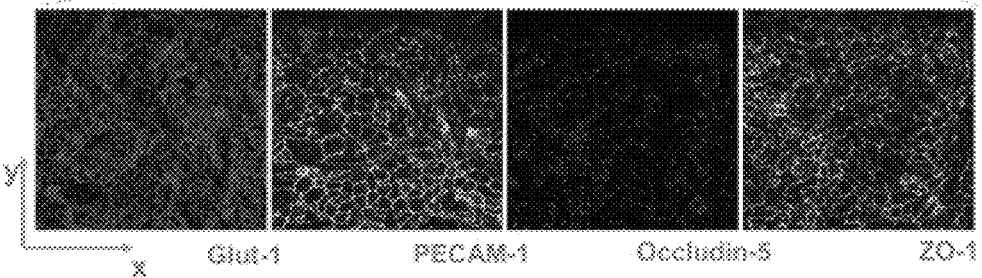
FIG. 42A  FIG. 42B

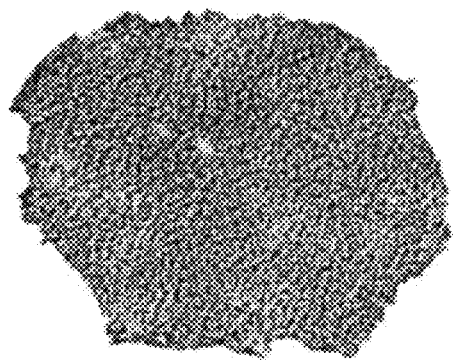
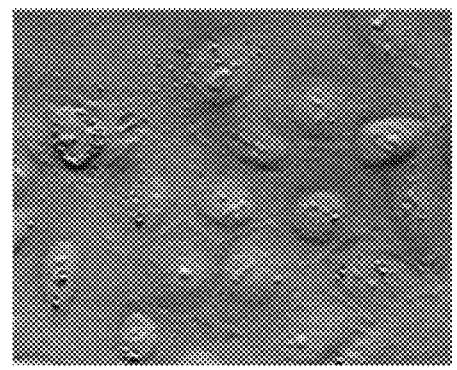
Day 0 → Day 18-22

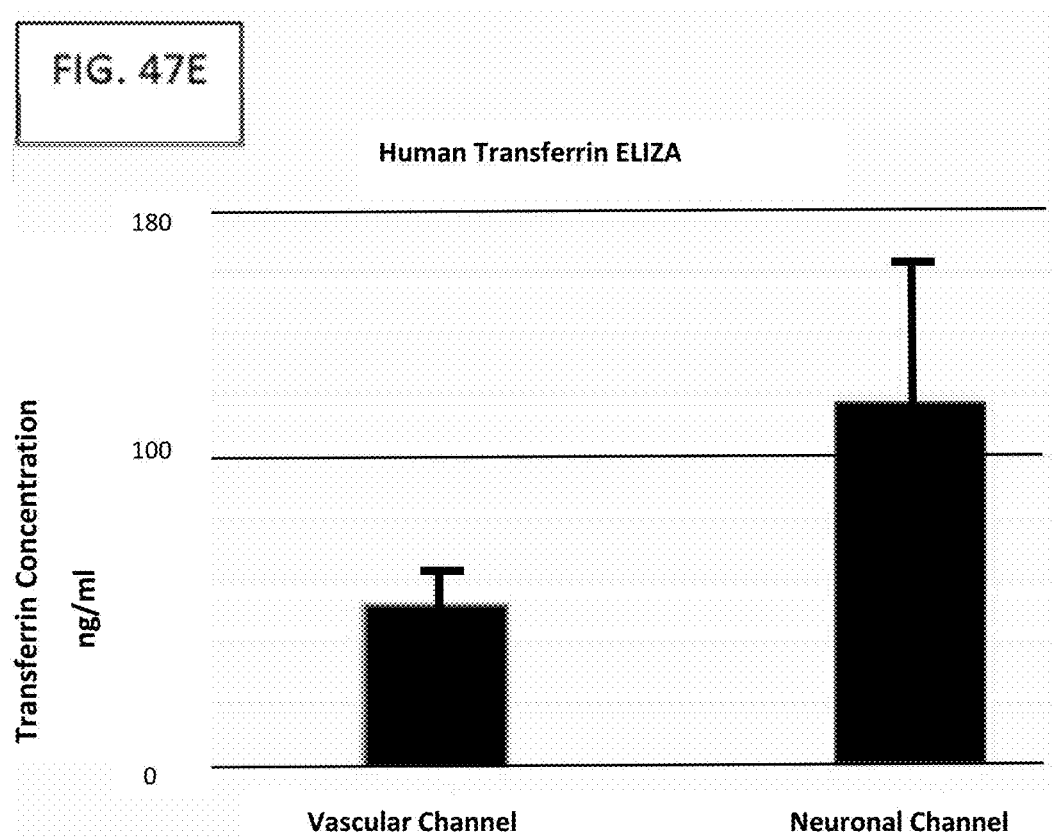

FIGURE 50

Exemplary ECM Calibration on PDMS 24-well plate.

| | ECM | Conditions | Cells | Results |
|---|---|---|---|---|
| Neural | Collagen/fibronectin (4:1) | 1:1 H2O (Transwell conc.) | 03iBMEC<br>1 x 10^5/ml<br>5 x 10^5 | Poor<br>Poor |
| | Collagen/fibronectin (4:1) | 1:5 H2O (Diluted) | 03iBMEC<br>1 x 10^5/ml<br>5 x 10^6 | Poor<br>Best |
| | MATRIGEL® | 0.5 mg/ml | 03iBMEC<br>1 x 10^5/ml<br>5 x 10^6 | Poor<br>Poor |
| | Laminin | 50 microg/ml | 03iEZ<br>5 x 10^4<br>1 x 10^5 | Poor<br>Good |
| Endothelial | Laminin | 5 microg/ml | 03iEZ<br>5 x 10^4<br>1 x 10^5 | Poor<br>Poor |
| | Laminin | 50 microg/ml | 25iMNp<br>5 x 10^4<br>1 x 10^5 | Good<br>Best |
| | Laminin | 5 microg/ml | 25iMNp<br>5 x 10^4<br>1 x 10^5 | Poor<br>Poor |
| | MATRIGEL® | 0.5 mg/ml | 03iEZ<br>25iMNp | Poor<br>Poor |

DEVELOPMENT OF SPINAL CORD ON A MICROFLUIDIC CHIP

This application is a Continuation of, and claims priority to, co-pending PCT Application Serial No. PCT/US17/49115, filed Aug. 29, 2017, which is a continuation in part to U.S. application Ser. No. 15/352,289 filed Nov. 15, 2016, which is a national entry of PCT/US16/57724, filed Oct. 19, 2016, which claims priority to Provisional Application Ser. No. 62/380,780 filed on Aug. 29, 2016, the contents of which are incorporated herein in their entirety.

FIELD OF THE INVENTION

The invention relates to culturing brain cells and particularly astrocytes together with endothelial cells in a fluidic device under conditions whereby the cells mimic the structure and function of the blood brain barrier and/or spinal cord. Good viability and function allow for measurements of barrier integrity and physiology, whether by trans-epithelial electrical resistance (TEER), patch clamp or other testing measures.

BACKGROUND OF THE INVENTION

The blood-brain barrier is of major clinical relevance. Not only because dysfunction of the blood-brain barrier leads to degeneration of the neurovascular unit, but also because drugs that are supposed to treat neurological disorders often fail to permeate the blood-brain barrier. Because of its importance in disease and medical treatment, it would be highly advantageous to have a predictive model of the human blood-brain barrier that recapitulates aspects of the cerebral endothelial microenvironment in a controlled way.

SUMMARY OF THE INVENTION

In one embodiment, the invention relates to culturing brain cells and particularly astrocytes together with endothelial cells in a fluidic device under conditions whereby the cells mimic the structure and function of the blood brain barrier and/or spinal cord. Good viability and function allow for measurements of barrier integrity and physiology, whether by trans-epithelial electrical resistance (TEER), patch clamp or other testing measures.

In one embodiment, the invention relates to culturing endothelial cells (preferably brain-related endothelial cells), optionally astrocytes, optionally neurons and optionally pericytes in a microfluidic device, such as microfluidic chip (described herein) under conditions whereby the cells mimic one or more structural or functional features (e.g. tight junctions) of the blood brain barrier (BBB) and/or spinal cord. Good viability and function allow for measurements of barrier integrity and physiology, whether by transepithelial electrical resistance (TEER), electrophysiology (including, for example, patch clamp) or other testing measures. Indeed, neuronal cells, such as motor neurons, that are allowed to mature on a microfluidic chip, show a more mature electrophysiology (action potential patterns, for example) indicating a more advanced or accelerated maturation. Thus, in one embodiment, the present invention contemplates a microfluidic culture of iPSC-derived neural progenitor cells or (alternatively) neurons (e.g. a culture in a microfluidic setting, such as in a microchannel and/or microfluidic device) in contact with flowing media. In one embodiment, the iPSC-derived neural progenitors or (alternatively) neurons are cultured alone (without other cell types). In one embodiment, said neurons are iPSC-derived neurons. In one embodiment, said iPSC-derived neurons are motor neurons. In one embodiment, said neurons are cultured in a microchannel or on a membrane of a microfluidic chip. In one embodiment, said microfluidic chip comprises two microchannels separated by a porous membrane having first and second surfaces, wherein said neurons are cultured on said first or second surface. In one embodiment, said culturing is performed for 10, 12, 20, 24, 30, 36 or more days. In one embodiment, said neurons exhibit a more mature electrophysiology as compared to the same neurons cultured in a static culture. Culture of cells in the microfluidic chip, whether alone or in combination with other cells, drives maturation and/or differentiation further than existing systems.

It is not intended that the present invention be limited to only one type of test or measurement to assess the more mature phenotype of neurons and BMECs. In one embodiment, gene expression, Ca2+ flux imaging, immunofluorescent staining, and/or tissue morphology is assessed as evidence of more mature neurons, BMECs and/or astrocytes.

Where neurons, such as motor neurons (or their precursors), are co-cultured (i.e. cultured together) on a microfluidic chip with relevant vascular cells, such as brain microvascular endothelial cells, an even greater effect on differentiation, maturation and/or conditioning is observed. Thus, in one embodiment, the present invention contemplates a microfluidic co-culture of iPSC-derived neural progenitors or (alternatively) neurons with vascular cells, e.g. a microfluidic co-culture of neurons with iPSC-derived vasculature (e.g. said vascular cells are iPSC-derived vascular cells). In one embodiment, said iPSC-derived vascular cells are brain microvascular endothelial cells. In one embodiment, said neurons are iPSC-derived neurons. In one embodiment, said iPSC-derived neurons are motor neurons. In one embodiment, said vascular cells are co-cultured with said neurons in a microchannel or on a membrane of a microfluidic chip. In one embodiment, said microfluidic chip comprises two microchannels separated by a porous membrane having first and second surfaces, wherein said neurons are cultured on said first surface and said vascular cells are cultured on said second surface. In one embodiment, said culturing (e.g. under flow conditions) is performed for 10, 12, 20, 24, 30, 36 or more days. In one embodiment, at least a portion of said neurons and vascular cells are in contact with each other (whether by direct physical contact or indirect cell-to-cell communication). In one embodiment, said neurons and vascular cells are in contact with flowing culture media (e.g. the cells are adhered to a surface and the media flows over the cells at a controlled rate, bringing nutrients and removing waste). In one embodiment, said neurons exhibit a more mature electrophysiology as compared to the same neurons cultured in a static culture.

The microfluidic chip culture increases and accelerates function of iPSC-derived neurons, including motor neurons (MNs). Co-culture with iBMECs recreates known vascular-interaction pathways and further increased maturation in vitro. The fact that cells differentiate and mature more fully on a microfluidic chip indicates that the chip is a better culture tool than more conventional culture systems (e.g. transwell cultures and other static systems), providing a better model of what is going on in vivo (including what is going on in disease states). Thus, in one embodiment, the present invention contemplates a microfluidic device or chip comprising a co-culture of neurons, and more specifically, motor neurons, and more typically, induced motor neurons, with brain microvascular endothelial cells, and more typically, induced brain microvascular endothelial cells. In one embodiment, the present invention contemplates a method of making a co-culture on microfluidic device or chip comprising introducing neurons, and more specifically, motor neurons, and more typically, induced motor neurons, and brain microvascular endothelial cells, and more typically, induced brain microvascular endothelial cells into microfluidic device or chip, and flowing media over said cells. In one embodiment, said culturing (e.g. under flow conditions) is performed for 10, 12, 20, 24, 30, 36 or more days. In one embodiment, the microfluidic chip comprises two microchannels separated (at least in part) by a porous membrane (or other porous member) having first and second surfaces, wherein motor neurons, and more typically, induced motor neurons, are cultured on the first side (e.g. top surface) of the porous membrane (or other porous member) and brain microvascular endothelial cells, and more typically, induced brain microvascular endothelial cells, are cultured on the second surface (e.g. bottom surface) of the porous membrane (or other porous member). Vascular blood flow can be recreated by flowing media in the microchannels.

While not intending to limit the invention to any particular mechanism, it is believed that neuronal progenitor cells and neurons grown in contact with (including in direct contact with) iPSC-derived brain microvascular endothelial cells (BMECs) will mature more fully on a microfluidic chip. There may be a variety of components in the microenvironment that contribute to this result, including but not limited to, autocrine and paracrine signaling, ECM (protein) cues, mass transfer (due to flow), and mechanical forces (including fluid shear). Importantly, the data shows that the improved differentiation, maturation and/or conditioning can be achieved without the addition of exogenous factors.

In one embodiment, the present invention contemplates contact of neurons and brain related vascular cells, and more preferably, direct contact of iMNs and iBMECs on the microfluidic chip to enhance neuronal physiology as measured by electrophysiology and transcriptomics. It has been found that the chip accelerates diMN electrophysiological maturation. Moreover, a highly complex spontaneous activity of the neurons is observed in the chip. Indeed, neural tissue has more mature electrophysiological properties in the chip and in co-culture with BMECs. In some embodiments, more developed currents are observed in the neurons on the chip. In a preferred embodiment, the iMNs and iBMECs are generated from the same person, e.g. the stem cells of the same person. In one embodiment, the iMNs and iBMECs generated from the same patient line, e.g. the same patient stem cells. In one embodiment, the patient has symptoms of a CNS disorder, and more specifically, a neurodegenerative disease. In one embodiment, the neurodegenerative disease is ALS. In one embodiment, the neurodegenerative disease is Parkinson's disease. In one embodiment, the CNS disorder is Alzheimer's disease.

Relevant markers can be detected by fluorescence staining and immunochemistry. In a specific embodiment, cell morphology and movement on (or through) the "BBB-on-chip" is monitored in real-time. Furthermore, in one embodiment, the in vitro model presented by a "BBB-on-chip" can be used to inform drug development or the study of existing agents, by permitting the testing of drug candidates to see if they cross the BBB, harm it, or make it less permissive, potentially under specific coincident conditions or for specific individuals or populations. The BBB-on-chip may also be used for pre-screening and optimization of new treatments potentially as an alternative to animal work, serving as an in vitro proof of principle for clinical studies. Furthermore, the BBB-on-chip model may be used to study disease, including but not limited the role of genetics, environment, cell-to-cell communication, and the role of barrier integrity (or lack thereof) in CNS disease progression. In one embodiment, the present invention contemplates a BBB-on-chip where at least one population of cells is derived from a patient diagnosed with a disorder of the nervous system. In addition, the BBB-on-chip model may be used diagnostically in order to determine, for example, the presence of a medical condition (e.g. a genetic or acquired disease, syndrome or predisposition) or to predict the response of an individual to a potential treatment (e.g. tailoring the dose of medication on the basis of that patient's blood-brain barrier permeability to that medication).

In one embodiment, the present invention contemplates a method of culturing cells, comprising: a) providing a fluidic device comprising a membrane, said membrane comprising a top surface and a bottom surface; b) seeding cells on said bottom surface; and c) culturing said seeded cells under conditions that support the maturation of brain microvascular endothelial cells. In one embodiment, said cells are selected from the group consisting of stem cell-derived cells, cells differentiated from stem cells and primary cells. In one embodiment, said cells differentiated from stem cells are brain microvascular endothelial cells. In one embodiment, said cells differentiated from stem cells are iBMECs. In one embodiment, the method further comprises seeding said cells on said top surface and culturing said top surface seeded cells under conditions that support the maturation of at least one of astrocytes and neurons. In one embodiment, said neurons exhibit a more mature electrophysiology as compared to the same neurons cultured in a static culture. For example, a mature electrophysiology includes negative sodium channel current, positive potassium channel current, and/or action potential spikes of amplitude, duration and frequency similar to neurons in a physiological environment or when compared to static culture neurons, static culture neurons lack one or more of the aforementioned features. In one embodiment, said culturing of said top surface seeded cells further comprises culturing said seeded cells under conditions such that an astrocyte or portion thereof transmigrates said membrane and contacts one or more brain microvascular endothelial cells on said bottom surface. In one embodiment, said cells differentiated from stem cells seeded on said top surface are derived or extracted from EZ spheres, induced neural progenitor cells (iNPCs) or iMNPs. In one embodiment, said stem cells are human induced pluripotent stem cells. In one embodiment, said stem cells are human induced pluripotent stem cells. In one embodiment, prior to step b) at least one of said top or bottom surface are coated with one or more extracellular matrix proteins. In one embodiment, said top surface is coated with laminin. In one embodiment, said bottom surface is coated with a mixture of collagen and fibronectin, and lacks laminin. In one embodiment, said cells seeded on said top surface further comprise pericytes. In one embodiment, said conditions of step c) comprise exposing said seeded cells to a flow of culture media for a period of time (e.g. 4, 7, 10, 12, 20, 24, 30, 36 or more days). In one embodiment, said flow promotes differentiation of said induced motor neuron progenitor (iMNP) cells. In one embodiment, said flow promotes the formation of tight cell-to-cell junctions among said brain microvascular endothelial cells. In one embodiment, the method further comprises detecting said tight cell-to-cell junctions. In one embodiment, said tight cell-to-cell junctions are detected by TEER measurements. In one embodiment, the method further comprises step e) measuring of neuron or astrocyte activity by at least one of intracellular electrophysiology measurements (e.g. patch clamp measurements across the cell membrane), extracellular electrophysiology measurements (e.g field potentials generated by a plurality of cells), imaging using calcium-sensitive dyes or proteins, or imaging using voltage-sensitive dyes or proteins. In one embodiment, said tight cell-to-cell junctions are detected by cell permeability assays. In one embodiment, said brain microvascular endothelial cells express the marker Glut 1. In one embodiment, said culturing of step c) is performed for at least four days. In one embodiment, said culturing of step c) is performed for at least seven days. In one embodiment, said culturing of step c) is performed for 10, 12, 20, 24, 30, 36 or more days. In one embodiment, said fluidic device further comprises at least one inlet port and at least one outlet port, and said culture media enters said inlet port and exits said outlet port. In one embodiment, said membrane comprises a nanopatterned surface which promotes extended and directed neurite growth. The preferred nanopattern is linear valleys and ridges, but alternatives such as circular, curved, or any other desired shape or combination thereof are also contemplated.

In one embodiment, the present invention contemplates a method of culturing cells, comprising: a) providing a microfluidic device comprising a membrane, said membrane comprising a top surface and a bottom surface; b) coating said top surface of said membrane with laminin and said bottom surface with a mixture of collagen and fibronectin, said mixture free of laminin; c) seeding stem-cell derived brain cells on said top surface and brain microvascular endothelial cells on said bottom surface so as to create seeded cells; d) exposing said seeded cells to a flow of culture media for a period of time (e.g. 4, 7, 10, 12, 20, 24, 30, 36 or more days); and e) culturing said seeded cells under conditions such that said brain microvascular endothelial cells on said bottom surface form tight junctions. In one embodiment, said brain microvascular endothelial cells are free of neurons. In one embodiment, said microfluidic device comprises a first fluidic channel in fluidic communication with said top surface of said membrane and a second fluidic channel in fluidic communication with said bottom surface of said membrane, said first and second fluidic channels each comprising a surface that is parallel to said membrane, and each comprising side walls. In one embodiment, said brain microvascular endothelial cells grow on the parallel surface and side walls of the second fluidic channel so as to form a lumen. In one embodiment, said brain microvascular endothelial cells express the marker Glut 1. In one embodiment, said culturing of step e) is performed for at least four days. In one embodiment, said culturing of step e) is performed for at least seven days. In one embodiment, said culturing of step e) is performed for 10, 12, 20, 24, 30, 36 or more days. In one embodiment, said fluidic device further comprises at least one inlet port and at least one outlet port, and said culture media enters said inlet port and exits said outlet port. In one embodiment, said first and second fluidic channels comprise polydimethylsiloxane. In one embodiment, prior to step b) said first and second channels undergo a treatment to promote wetting. In one embodiment, said treatment to promote wetting is selected from the group consisting of plasma treatment, ion treatment, gas-phase deposition, liquid-phase deposition, adsorption, absorption or chemical reaction with one or more agents. In one embodiment, said stem-cell derived brain cells are seeded on wet laminin. In one embodiment, said mixture of collagen and fibronectin is dried prior to step c). In one embodiment, said fluidic device is stored after step b) and before step c). In one embodiment, said fluidic device is stored at a temperature below 25° C. In one embodiment, said fluidic device is stored in a refrigerator. In one embodiment, said induced motor neuron progenitor cells were stored frozen and then thawed prior to step c).

In one embodiment, the present invention contemplates a method of culturing cells, comprising: a) providing a fluidic device comprising a membrane, said membrane comprising a top surface and a bottom surface; b) coating said top surface of said membrane with laminin and said bottom surface with a mixture of collagen and fibronectin, said mixture free of laminin; c) seeding induced motor neuron progenitor cells on said top surface and brain microvascular endothelial cells on said bottom surface so as to create seeded cells; d) exposing said seeded cells to a flow of culture media for a period of time (e.g. 4, 7, 10, 12, 20, 24, 30, 36 or more days); and e) culturing said seeded cells under conditions such that said brain microvascular endothelial cells on said bottom surface form tight junctions. In one embodiment, said induced motor neuron progenitor cells are derived from induced pluripotent stem cells from a human patient diagnosed with a CNS disorder. In one embodiment, said flow promotes the differentiation of said induced motor neuron progenitor cells. In one embodiment, said induced motor neuron progenitor cells are derived from induced pluripotent stem cells from a patient diagnosed with Amyotrophic lateral sclerosis (ALS). In one embodiment, said brain microvascular endothelial cells are derived from induced pluripotent stem cells from a patient diagnosed with MCT8-specific thyroid hormone cell-membrane transporter deficiency. In one embodiment, said induced motor neuron progenitor cells were stored frozen and then thawed prior to step c).

In one embodiment, the present invention contemplates a fluidic device comprising a membrane, said membrane comprising a top surface and a bottom surface, said top surface comprising at least one stem-cell derived brain cell and said bottom surface comprising brain microvascular endothelial cells. In one embodiment, said at least one stem-cell derived brain cell is selected from the group consisting of induced motor neuron progenitor cells, EZ Sphere-derived cells and iNPCs. In one embodiment, the device further comprises a first fluidic channel in fluidic communication with said top surface of said membrane and a second fluidic channel in fluidic communication with said bottom surface of said membrane, said first and second fluidic channels each comprising a surface that is parallel to said membrane, and each comprising side walls. In one embodiment, said brain microvascular endothelial cells are present on the parallel surface and side walls of the second fluidic channel so as to constitute a lumen.

In one embodiment, the present invention contemplates a system, comprising a) a fluidic device comprising a membrane, said membrane comprising a top surface and a bottom surface, said top surface comprising at least one stem-cell derived brain cell and said bottom surface comprising brain microvascular endothelial cells, said microfluidic device further comprising a first fluidic channel in fluidic communication with said top surface of said membrane and a second fluidic channel in fluidic communication with said bottom surface of said membrane, b) a fluid source in fluidic communication with said first and second fluidic channels, whereby said cells are exposed to fluid at a flow rate for a period of time (e.g. 4, 7, 10, 12, 20, 24, 30, 36 or more days). In one embodiment, said at least one stem-cell derived brain cell is selected from the group consisting of induced motor neuron progenitor cells, EZ Sphere-derive cells and iNPCs.

Traditional in vitro systems used in human stem cell-based modeling of neurodegenerative diseases such as Amyotrophic Lateral Sclerosis (ALS) possess inherent limitations for biological and pathological relevance. Studies have revealed that stem cell-derived neural tissue is unable to mature fully in vitro. This fetal-like immature phenotype presents a challenge when studying genetic contribution to adult-onset pathogenesis in vitro. Here, we hypothesize that iPSC-derived motor neurons (MNs) can better mature through enhanced endogenous media conditioning and the addition of developmentally relevant, non-neuronal cell types in co-culture. To address this, such motor neurons are matured in a microfluidic device and the functional effects of micro-media volumes are assessed on the neuronal maturation of induced pluripotent stem cell (iPSC)-derived MNs originating from non-disease control and ALS patients.

Without being bound to theory, the influence of non-neuronal cell types (e.g. astrocytes, etc.) on neuron maturation can be enhanced by recirculating one or more of the fluids in the microfluidic device. For example, medium flowing through a neuronal compartment can be recirculated by fluidically connecting the output of that channel back into its input, optionally by flowing through a recirculation pump. Many methods of recirculation are known in the art, including for example, discrete recirculation wherein output fluids are introduced back into an input reservoir using a pipetting or liquid-handling operation or a specialized valving system.

In some embodiments, the effect of non-neuronal cell types on neuron maturation can be obtained by providing the microfluidic device with fluidics that have been conditioned by culture with one or more non-neuronal cell types. For example, medium cultured with BMECs and/or astrocytes can be used as input or combined, mixed and/or interleaved with one or more input fluids of the BBB-chip. The use of conditioned fluids may be used in addition to or instead of the including of non-neuronal cell types within the chip.

The data (e.g. maturation data (PCA), electrophysiology data and calcium imaging data showing more activity) show that iPSC-derived motor neurons (MNs) can better mature (e.g. develop to a more mature state) through enhanced endogenous media conditioning and/or the addition of developmentally relevant, neuronal or non-neuronal cell types in co-culture. Developmentally relevant cell types include brain microvascular endothelial cells and astrocytes that emerge at the time point at which current standard culture methods are known to be stagnated. The evidence also supports improved maturation of the astrocytes and BMECs. As described herein, astrocytes were observed to send out of processes to contact the endothelial cells. As described herein, improved and sustained barrier function indicates maturation of the BMECs.

Without intending that the present invention be bound by theory as to the mechanism by which the cells cultured in a microfluidic setting exhibit a more mature phenotype, it is believed that it is the improved microenvironment that the Chip provides that is responsible for the effect. The relevant elements of the Chip microenvironment include (but are not limited to): a) improved communication between cells of the same type, e.g. because of a lower volume of dilution/distribution within the chip (in one embodiment, enhanced endogenous media conditioning is employed); b) communication between the different cell type (e.g. neuron/astrocyte communication, astrocyte/endo communication (in one embodiment, the present invention contemplates developmentally relevant, neuronal or non-neuronal cell types in co-culture); c) mass transport properties related to the fluidic environment (e.g. flow affects autocrine signaling, paracrine signaling, washing out waste products, providing nutrients, etc.); d) access to both the apical and basal sides of the BMECs and, potentially, the biochemical independence/isolation of those two sides; e) mechanical forces, especially shear forces in this case (e.g. shear force is known to affect endothelial cell phenotype); 0 enhanced replenishment of media factors related to differentiation (e.g. as opposed to static culture, where the concentration of the factors may deplete through culture/incubation); g) improved ECM signaling, both the ability to coat with multiple ECMs in different regions (e.g. one ECM for the neuronal compartment and a different one for the endothelial cells) and the ability of the cells in the system to remodel the ECM and its composition (e.g. the BMECs may be laying down ECM that could influence the astrocytes).

Without being bound by theory, it is believed that the Chip microenvironment promotes differentiation for largely the same reasons that it helps maturation (see above). In the microfluidic setting, it is believed that the cells derived from stem cells reach the intended fate more completely, more accurately and/or faster.

Without being bound by theory, it is believed that the microfluidic setting promotes improved longevity of the cells and/or improved maintenance of at least one function of the BBB, neurons or neurovascular junction. We observe such improved longevity and maintenance of function, for example, in the survival of the neurons and maintenance of their firing, and in the maintenance of the BMEC barrier function.

While not intending to be limited to any specific mechanism, the data indicates that culturing the cells under flow (preferably continuous flow) conditions (instead of a static culture) increased the number of iMNs and BMECs per chip when measured over time, e.g. 10, 12, 20, 24, 30 and 36 days or more. In a preferred embodiment, MNs are co-cultured with iPSC-derived BMECs under flow (preferably continuous flow) conditions (e.g. MNs on the top surface of the membrane and BMECs on the bottom surface). Such cultures became dense, thick tissue indicating a three dimensional structure. At the membrane, both cell types could be observed interacting. Just below the membrane both cell types interacted and diMNs were observed to infiltrate in large clusters into the bottom channel. BMECs persisted on the bottom channel and continued to form tight junctions.

In one embodiment, the present invention contemplates a method of culturing cells, comprising: a) providing a microfluidic device comprising a membrane, said membrane comprising a top surface and a bottom surface; b) seeding stem-cell derived brain cells on said top surface and brain microvascular endothelial cells on said bottom surface so as to create seeded cells; c) exposing said seeded cells to a flow of culture media for a period of time; and d) culturing said seeded cells under conditions such that a percentage of said cells exhibit periodic spontaneous bursts of calcium transient activity indicative of spinal cord development. It is not intended that the present invention be limited to the precise duration of exposing of step c) or culturing of step d). However, in one embodiment, said seeded cells are cultured for more than twenty days (e.g. and exposed to flow for that period). In another embodiment, said seeded cells are cultured for more than twenty-five days (e.g. and exposed to flow for that period). It is also not intended that the present invention be limited to any particular percentage of cells of cells exhibiting periodic spontaneous bursts of calcium transient activity. In one embodiment, the percentage is between 1 and 5% of active cells, more preferably between 5 and 10% of active cells, and still more preferably between 10 and 20% of active cells. In one embodiment, the percentage of cells exhibiting periodic spontaneous bursts of calcium transient activity is at least 20%. In another embodiment, the percentage of cells exhibiting periodic spontaneous bursts of calcium transient activity is at least 30% (or more than 30%).

In one embodiment of the above-described method, said stem-cell derived neurons seeded on said top surface are disposed within a gel or gel-precursor. In one embodiment, said stem-cell derived neurons are seeded on top of a gel present on said top surface of said membrane.

In one embodiment, said stem-cell derived neurons are derived from induced pluripotent stem-cells. In one embodiment, said stem-cell derived neurons are derived from embryonic stem-cells. In one embodiment, said neurons comprise one or more cell types selected from the list comprising of motor neurons, upper motor neurons, lower motor neurons, sensory neurons, and interneurons. In one embodiment, the method further comprises seeding glial cells on said top surface. In one embodiment, glial cells comprise one or more cell types selected from the list comprising astrocytes, oligodendrocytes, ependymal cells, Schwann cells, microglia, and satellite cells.

In one embodiment, said culture media is serum free. In another embodiment, said culture media comprises blood or at least one blood component (e.g. serum).

It is not intended that the seeded cells be restricted to any one particular region or area. However, in one embodiment, said brain microvascular endothelial cells grow on the parallel surface and side walls of the second microfluidic channel so as to form a lumen.

The cells can be assessed for markers that indicate the state of maturation or differentiation. In one embodiment, said brain microvascular endothelial cells express the marker Glut 1.

In preferred embodiments, the cells are seeded after coating the surface of the microfluidic device (e.g. the surface which the cells contact) with an ECM. In one embodiment, said stem-cell derived brain cells are seeded on wet laminin.

It is not intended that the present invention be limited by the nature of the stem-cell derived brain cells. However, in a preferred embodiment, said stem-cell derived brain cells comprise induced motor neuron progenitor cells.

A variety of microfluidic designs are contemplated. In one embodiment, said microfluidic device comprises a first microfluidic channel in fluidic communication with said top surface of said membrane and a second microfluidic channel in fluidic communication with said bottom surface of said membrane, said first and second microfluidic channels each comprising a surface that is parallel to said membrane, and each comprising side walls. In one embodiment, said microfluidic device further comprises at least one inlet port and at least one outlet port, and said culture media enters said inlet port and exits said outlet port.

It is not intended that the present invention be limited to the material used to make the microfluidic device (or portions thereof). In one embodiment, said first and second microfluidic channels comprise polydimethylsiloxane.

In yet another embodiment, the present invention contemplates a method of culturing cells, comprising: a) providing a microfluidic device comprising a membrane, said membrane comprising a top surface and a bottom surface; b) seeding induced motor neuron progenitor cells on said top surface and brain microvascular endothelial cells on said bottom surface so as to create seeded cells; c) exposing said seeded cells to a flow of culture media for a period of time; and d) culturing said seeded cells under conditions such that a percentage of said cells exhibit periodic spontaneous bursts of calcium transient activity indicative of spinal cord development. Again, it is not intended that the present invention be limited to the precise duration of exposing of step c) or culturing of step d). However, in one embodiment, said seeded cells are cultured for more than twenty days (e.g. and exposed to flow for that period). In another embodiment, said seeded cells are cultured for more than twenty-five days (e.g. and exposed to flow for that period). It is also not intended that the present invention be limited to any particular percentage of cells. In one embodiment, the percentage is between 1 and 5% of active cells, more preferably between 5 and 10% of active cells, and still more preferably between 10 and 20% of active cells. In one embodiment, the percentage of cells exhibiting periodic spontaneous bursts of calcium transient activity is at least 20%. In another embodiment, the percentage of cells exhibiting periodic spontaneous bursts of calcium transient activity is at least 30% (or more than 30%).

In one embodiment, said induced motor neuron progenitor cells are derived from induced pluripotent stem cells from a human patient diagnosed with a CNS disorder. In one embodiment, said flow promotes the differentiation of said induced motor neuron progenitor cells. In one embodiment, said induced motor neuron progenitor cells differentiate into neurons. In one embodiment, said neurons exhibit a more mature electrophysiology as compared to the same neurons cultured in a static culture.

In one embodiment of the above-described method, said neuron progenitors are seeded on said top surface are disposed within a gel or gel-precursor. In one embodiment, said neuron progenitors are seeded on top of a gel present on said top surface of said membrane. In one embodiment, said neuron progenitors are derived from induced pluripotent stem-cells. In one embodiment, said neuron progenitors are derived from embryonic stem-cells. In one embodiment, said neuron progenitors comprise one or more cell types selected from the list comprising of motor neuron progenitors, upper motor neuron progenitors, lower motor neuron progenitors, sensory neuron progenitors, and interneuron progenitors. In one embodiment, the method further comprises seeding glial cells on said top surface. In one embodiment, glial cells comprise one or more cell types selected from the list comprising astrocytes, oligodendrocytes, ependymal cells, Schwann cells, microglia, and satellite cells.

In one embodiment, said culture media is serum free. In one embodiment, said culture media comprises blood or at least one blood component (e.g. serum).

In yet another embodiment, the present invention contemplates a method of culturing cells, comprising: a) providing a microfluidic device comprising a membrane, said membrane comprising a top surface and a bottom surface; b) seeding induced motor neuron progenitor cells on said top surface and brain microvascular endothelial cells on said bottom surface so as to create seeded cells; c) exposing said seeded cells to a flow of culture media for a period of time; and d) culturing said seeded cells under conditions such that a portion of said progenitor cells differentiate to neurons and a percentage of said neurons exhibit complex and repetitive bursts of neuronal activity indicative of neuronal networks being established in the microfluidic device. Again, it is not intended that the present invention be limited to the precise duration of exposing of step c) or culturing of step d). However, in one embodiment, said seeded cells are cultured for more than twelve days (e.g. and exposed to flow for that period). In another embodiment, said seeded cells are cultured for more than twenty days, or even more than twenty-five days (e.g. and exposed to flow for that period). It is also not intended that the present invention be limited to any particular percentage of cells of cells exhibiting periodic spontaneous bursts of calcium transient activity. In one embodiment, the percentage is between 1 and 5% of active cells, more preferably between 5 and 10% of active cells, and still more preferably between 10 and 20% of active cells. In one embodiment, the percentage of cells is at least 20%. In another embodiment, the percentage of cells is at least 30% (or more than 30%).

In yet another embodiment, the present invention contemplates a method of culturing cells, comprising: a) providing a microfluidic device comprising a top chamber, a bottom chamber, and a membrane disposed in at least one interface region between said top and bottom chambers; b) seeding stem-cell derived neurons within at least a portion of said top chamber and brain microvascular endothelial cells within at least a portion of said bottom chamber so as to create seeded cells; c) exposing at least a portion of said seeded cells to a flow of a first fluid for a period of time; and d) culturing said seeded cells under conditions such that a percentage of said neurons exhibit development indicative of the spinal cord. In one embodiment, said exhibited development indicative of the spinal cord comprises spontaneous bursts of calcium transient activity. In one embodiment, said spontaneous bursts activity is periodic. In one embodiment, said exhibited development indicative of the spinal cord comprises at least one marker selected from the list comprising SMI32, nuclear marker islet 1 (ISL1), Beta 3 tubulin (TUBB3), NKX6.1, neurofilament marker microtubule-associated protein 2 (MAP2), and synaptic marker synaptophysin (SYNP). In one embodiment, said top chamber comprises an open region. In one embodiment, said microfluidic device further comprises a top channel, said top channel fluidically coupled to said top chamber. In one embodiment, said top channel comprises the top chamber. In one embodiment, said microfluidic device further comprises a bottom channel, said bottom channel fluidically coupled to said bottom chamber. In one embodiment, said bottom channel comprises the bottom chamber. In one embodiment, said stem-cell derived neurons seeded within at least a portion of said top chamber are disposed within a gel or gel-precursor. In one embodiment, said stem-cell derived neurons are seeded on top of a gel present within a portion of said top chamber. In one embodiment, said stem-cell derived neurons are derived from induced pluripotent stem-cells. In one embodiment, said stem-cell derived neurons are derived from embryonic stem-cells. In one embodiment, said neurons comprise one or more cell types selected from the list comprising of motor neurons, upper motor neurons, lower motor neurons, sensory neurons, and interneurons. In one embodiment, the method further comprises seeding glial cells on said top surface. In one embodiment, said glial cells comprise one or more cell types selected from the list comprising astrocytes, oligodendrocytes, ependymal cells, Schwann cells, microglia, and satellite cells. In one embodiment, said first fluid comprises culture media. In one embodiment, said first fluid comprises blood or at least one blood component.

In yet another embodiment, the present invention contemplates a method of culturing cells, comprising: a) providing a microfluidic device comprising a top chamber, a bottom chamber, and a membrane disposed in at least one interface region between said top and bottom chambers; b) seeding neuron progenitors within at least a portion of said top chamber and brain microvascular endothelial cells within at least a portion of said bottom chamber so as to create seeded cells; c) exposing at least a portion of said seeded cells to a flow of a first fluid for a period of time; and d) culturing said seeded cells under conditions such that a portion of said progenitor cells differentiate to neurons and a percentage of said neurons exhibit development indicative of the spinal cord. In one embodiment of this method, said exhibited development indicative of the spinal cord comprises spontaneous bursts of calcium transient activity. In one embodiment, said spontaneous bursts activity is periodic. In one embodiment, said exhibited development indicative of the spinal cord comprises at least one marker selected from the list comprising SMI32, nuclear marker islet 1 (ISL1), Beta 3 tubulin (TUBB3), NKX6.1, neurofilament marker microtubule-associated protein 2 (MAP2), and synaptic marker synaptophysin (SYNP). In one embodiment, said top chamber comprises an open region. In one embodiment, said microfluidic device further comprises a top channel, said top channel fluidically coupled to said top chamber. In one embodiment, said top channel comprises the top chamber. In one embodiment, said microfluidic device further comprises a bottom channel, said bottom channel fluidically coupled to said bottom chamber. In one embodiment, said bottom channel comprises the bottom chamber. In one embodiment, said neuron progenitors seeded within at least a portion of said top chamber are disposed within a gel or gel-precursor. In one embodiment, said neuron progenitors are seeded on top of a gel present within a portion of said top chamber. In one embodiment, said neuron progenitors are derived from induced pluripotent stem-cells. In one embodiment, said neuron progenitors are derived from embryonic stem-cells. In one embodiment, said neurons comprise one or more cell types selected from the list comprising of motor neurons, upper motor neurons, lower motor neurons, sensory neurons, and interneurons. In one embodiment, the method further comprises seeding glial cells on said top surface. In one embodiment, said glial cells comprise one or more cell types selected from the list comprising astrocytes, oligodendrocytes, ependymal cells, Schwann cells, microglia, and satellite cells. In one embodiment, said first fluid comprises culture media. In one embodiment, said first fluid comprises blood or at least one blood component.

In still another embodiment, the present invention contemplates seeding a microfluidic device with spinal neural progenitor cells. In one embodiment, the present invention contemplates differentiation of spinal neural progenitors (SNPs) on-chip or off-chip from induced pluripotent stem cell (iPSC) cultures. In one embodiment, cells are fated to neural ectoderm (NE) using a WNT agonist (e.g. CHIR99021) and SMAD inhibitors (e.g. LDN193189 and SB431542) for a plurality of days (e.g. 6 days) then patterned to ventral spinal neurons using Retinoic Acid (RA) and Sonic hedgehog agonist (SAG) in culture plates (e.g. 6-well plates). If cultured off-chip, the resulting SNPs can thereafter (e.g. at day 10, 11, 12 or thereafter) be seeded on the microfluidic device (e.g. the chip). Alternatively, at day 12 (or thereafter), SNPs can be frozen, banked (stored) and later thawed for seeding on the chip. It is not intended that the present invention be limited by the nature of the "microfluidic device" or "chip" used when seeding SNPs. However, preferred microfluidic devices and chips are described in U.S. Pat. No. 8,647,861, hereby incorporated by reference, and they are microfluidic "organ-on-chip" devices comprising living cells in microchannels, e.g. cells on membranes in microchannels exposed to culture fluid at a flow rate. In one embodiment, the microfluidic device comprises top and bottom channels separated by a membrane, and the SNPs are seeded in the top channel. In one embodiment, after seeding, periodic spontaneous bursts of calcium transient activity are detected.

Definitions

Some abbreviations are used herein. For example, "MN" refers to motor neurons. The letter "i" indicates "induced." Thus, "iMN" indicates induced motor neurons, i.e. motor neurons that were induced or generated from other cells, e.g. stem cells. "diMN" indicates direct induced motor neurons. "iMNP" indicates induced motor neuron progenitor cells, which are not fully differentiated into mature neurons.

In one embodiment, the starting material for generating at least one cellular component for the BBB generated on a microfluidic device (or simply "BBB-on-chip") comprises stem cells (e.g. see the protocol in Example 1, below). In particular embodiments, these stem cells may include, for example, induced pluripotent stem cells (iPS cells) or embryonic stem cells. In one embodiment, progenitor cells (derived from stem cells) related to neural or vascular lineages or cells directly reprogrammed into astrocytes, neurons, pericytes, endothelial cells, neural lineage progenitors or endothelial lineage progenitors are employed/seeded on the chip. It is important to note that not all cell types involved in the BBB-on-chip must be generated from stem cells. For example, the BBB-on-chip may employ primary brain microvascular endothelial cells (BMECs). Techniques are known in the art to reprogram, expand and characterize human iPS cells from human skin or blood tissues of healthy subjects and diseased patients. For example, a non-integrating system based on the oriP/EBNA1 (Epstein-Barr nuclear antigen-1) episomal plasmid vector system can be used to avoid potential deleterious effects of random insertion of proviral sequences into the genome. See Okita K, et al., "A more efficient method to generate integration-free human iPS cells," Nat Methods. 2011 May;8:409. It is preferred that the iPSC lines so generated express the pluripotency markers (SSEA4, TRA-1-81, OCT3/4, SOX2) along with a normal karyotype. In the present invention, iPS cells are used to generate components of the BBB-on-chip, e.g. BMECs, neurons, etc. While in many cases, the iPS cells are from normal subjects, it is also contemplated that the iPS cells can be derived from patients exhibiting symptoms of disease. In one embodiment, the BBB-on-chip is populated with cells derived from iPS cells from a patient diagnosed with a disorder of the nervous system, including but not limited to iPSC-derived motor neurons from Amyotrophic lateral sclerosis (ALS) patients. See D. Sareen et al., "Targeting RNA foci in iPSC-derived motor neurons from ALS patients with C9ORF72 repeat expansion" Sci Transl Med. 2013 Oct. 23; 5(208): 208ra149.

In one embodiment, the present invention contemplates differentiating "stem-cell derived brain cells" on the chip, i.e. in a microfluidic environment. The term "stem-cell derived brain cells" refers to cells derived from stem cells that fall on a spectrum of differentiation. For example, in one embodiment, induced motor neuron progenitor cells (including but not limited to, iPSC-derived forebrain neural progenitors) are derived from induced pluripotent stem cells, but they are not fully differentiated. In one embodiment, induced motor neuron progenitor cells are differentiated on-chip to generate motor neurons, and ultimately mature motor neurons. Thus, in one embodiment, the present invention contemplates a method of culturing cells, comprising: a) providing a microfluidic device (optionally comprising a membrane, said membrane comprising a top surface and a bottom surface); b) seeding induced motor neuron progenitor cells (optionally on said top surface and optionally brain microvascular endothelial cells on said bottom surface so as to create seeded cells); c) exposing said seeded cells to a flow of culture media for a period of time (days to weeks to months) under conditions such that said at least a portion of said progenitor cells differentiate into motor neurons (and preferably wherein said motor neurons display a mature phenotype based on testing described herein or staining). In one embodiment, the method (optionally) further comprises e) culturing said seeded cells under conditions such that said brain microvascular endothelial cells on said bottom surface form tight junctions.

As another example, in one embodiment, induced brain microvascular endothelial progenitor cells are derived from induced pluripotent stem cells, but they are not fully differentiated. In one embodiment, induced brain microvascular endothelial progenitor cells are differentiated on-chip to generate BMECs, and ultimately mature BMECs. Thus, in one embodiment, the present invention contemplates a method of culturing cells, comprising: a) providing a microfluidic device (optionally comprising a membrane, said membrane comprising a top surface and a bottom surface); b) seeding induced brain microvascular endothelial progenitor cells (on said top surface or on said bottom surface so as to create seeded cells); c) exposing said seeded cells to a flow of culture media for a period of time (days to weeks to months) under conditions such that said at least a portion of said progenitor cells differentiate into brain microvascular endothelial cells (and preferably wherein said BMECs display a mature phenotype based on testing described herein or staining).

It is not intended that the present invention be limited by the nature of the "microfluidic device" or "chip." However, preferred microfluidic devices and chips are described in U.S. Pat. No. 8,647,861, hereby incorporated by reference, and they are microfluidic "organ-on-chip" devices comprising living cells in microchannels, e.g. cells on membranes in microchannels exposed to culture fluid at a flow rate. It is important to note that the features enabling the actuation of strain or mechanical forces on the cells within the "organ-on-chip" device are optional with regards to the "BBB-on-chip" and may be omitted. Flow is important and stands in contrast to static 2D culture. Using a flow in the microchannel(s) allows for the perfusion of cell culture medium throughout the cell culture during in vitro studies and as such offer a more in vivo-like physical environment. In simple terms, an inlet port allows injection of cell culture medium, blood, blood component or mixture thereof into a cell-laden microfluidic channel or chamber, thus delivering nutrients and oxygen to cells. An outlet port then permits the exit of remaining liquid as well as harmful metabolic by-products. While continuous flow is preferable due to its application of controlled shear forces, either of the device's fluidic paths could also be cultured under "stop flow" conditions, where the flow is engaged intermittently, interspersed by static culture.

Microfluidic devices are conveniently made of polydimethylsiloxane (PDMS), polyurethane, polycarbonate, polystyrene, polymethyl methacrylate, polyimide, styrene-ethylene-butylene-styrene (SEBS), polypropylene, or any combinations thereof. The present invention contemplates treatment of such substances to promote cell adhesion, selection or differentiation or fluid wetting such as treatments selected from the group consisting of plasma treatment, ion treatment, gas-phase deposition, liquid-phase deposition, adsorption, absorption or chemical reaction with one or more agents.

Additionally, the term "microfluidic" as used herein relates to components where moving fluid is constrained in or directed through one or more channels wherein one or more dimensions are 10 mm or smaller (microscale). Microfluidic channels may be larger than microscale in one or more directions, though the channel(s) may be on the microscale in at least one direction. In some instances the geometry of a microfluidic channel may be configured to control the fluid flow rate through the channel. Microfluidic channels can be formed of various geometries to facilitate a wide range of flow rates through the channels. However, it is important to note that while the present disclosure makes frequent reference to "microfluidic" devices, much of what is taught applies similarly or equally to larger fluidic devices. Larger devices may be especially relevant if the "BBB-on-chip" is intended for therapeutic application. Examples of applications that may make advantage of larger fluidic devices include the use of the device for the generation of highly differentiated cells (e.g. the device can used to drive cell differentiation and/or maturation, whereupon the cells are extracted for downstream use, which may include implantation, use in an extracorporeal device, or research use), or use of the device for implantation or extracorporeal use, for example, as an artificial blood-brain barrier or a dialysis-like technology.

As used herein, the phrases "connected to," "coupled to," and "in communication with" refer to any form of interaction between two or more entities, including mechanical, electrical, magnetic, electromagnetic, fluidic, and thermal interaction. For example, in one embodiment, first and second channels in a microfluidic device are in fluidic communication with a fluid reservoir. Two components may be coupled to each other even though they are not in direct contact with each other. For example, two components may be coupled to each other through an intermediate component (e.g. tubing or other conduit).

The surfaces of the microchannels and/or the membrane can be coated with cell adhesive, selective or promotive molecules to support the attachment of cells and promote their organization into tissues. Where a membrane is used, tissues can form on either the upper surface of the membrane, the lower surface of the membrane, any of the surfaces of the channels or cavities present on either side of the membrane or any combination thereof. In one embodiment, different cells are living on the upper and lower surfaces, thereby creating one or more tissue-tissue interfaces separated by the membrane. The membrane may be porous, flexible, elastic, or a combination thereof with pores large enough to only permit exchange of gases and/or small chemicals, or large enough to permit migration and tran-schannel passage of large proteins, as well as whole living cells and/or portions thereof (e.g. the endfoot of an astrocyte). Depending on the size-scale of the pores and manufacturing preferences, the pores may be defined, for example, using lithography, molding, laser-drilling or track-etching, intrinsic to a selected material (for example, polyacrylamide gel, collagen gel, paper, cellulose) or engineered into the material (e.g. by generating an open-cell polymer or matrix).

It is not intended that the present invention be limited to particular "flow rates" or means for generating flow rates. In one embodiment, a flow rate of between 5 and 200 uL/hr, and more preferably between 20-100 uL/hr, and still more preferably between 10 and 60 uL/hr, and still more preferably between 20-50 uL/hr, is contemplated. In one embodiment, pressure is applied through the lid (11) and the lid seals against the reservoir(s) (see FIG. 22B). For example, when one applies 1 kPa, this nominal pressure results, in one embodiment, in a flow rate of approximately 30-40 uL/hr. When one applies a pressure of between 0.5 kPa, this nominal pressure results, in one embodiment, in a flow rate of between 15 uL/hr and 30 uL/hr.

There are many ways to evaluate the integrity and physiology of an in vitro system that mimics the blood brain barrier. Two of the most common methods are Transepithelial Electric Resistance (TEER) and Lucifer Yellow (LY) rejection. Importantly, manipulations must be performed using aseptic techniques in order for the cells to remain in culture without contamination. TEER measures the resistance to pass current across one or more cell layers on a membrane. The measurement may be affected by the pore size and density of the membrane, but it aims to ascertain cell and/or tissue properties. The TEER value is considered a good measure of the integrity of the cell monolayer.

Lucifer Yellow (LY) travels across cell monolayers only through passive paracellular diffusion (through spaces between cells) and has low permeability. Therefore it is considerably impeded in passing across cell monolayers with tight junctions. Permeability (Papp) for LY of <5 to 12 nm/s has been reported to be indicative of well-established monolayers.

Description of the Tables

FIG. 50 shows various conditions (especially related to surface treatment and cell seeding) tested for seeding neural cells (EZ spheres and iMNPs) and endothelial cells (iBMECs), which may optionally originate from frozen stocks of cells. Ebert et al., "EZ spheres: A stable and expandable culture system for the generation of pre-rosette multipotent stem cells from human ESCs and iPSCs" Stem Cell Res. (2013) 10(3):417-427; Lippmann et al., "Human Blood-Brain Barrier Endothelial Cells Derived From Pluripotent Stem Cells" Nat. Biotechnol. (2012) 30(8):783-791; and Sareen et al., "Human neural progenitor cells generated from induced pluripotent stem cells can survive, migrate, and integrate in the rodent spinal cord" J. Comp. Neurol. (2014) 522(12): 2707-2728. The best results for iBMECs were achieved with a mixture of collagen and fibronectin (4:1 ratio). The best results for iMNPs were achieved with laminin. A variety of surface treatments and coating materials are known in the art (e.g. from traditional plate-based tissue culture or microfluidic tissue culture), for example, plasma treatment, corona treatment, aminopropyl triethoxysilane (APTES), collagen (including type I and type IV), fibronectin, laminin, gelatin, MATRIGEL® substrate, and mixtures thereof. The BBB-on-chip can make use of stem cells as the origin for either one or more of its neural components (which includes at least astrocytes or related cells), one or more of its endothelial components, or both. In particular embodiments, these stem cells may include induced pluripotent stem cells (iPS cells) or embryonic stem cells. In one embodiment, progenitor cells related to neural or vascular lineages or cells directly reprogrammed into astrocytes, endothelial cells, neural lineage progenitors or endothelial lineage progenitors are contemplated for seeding on the chip. The cells may be differentiated into respective cells type before they are deposited in the BBB-on-chip, differentiated within the BBB-on-chip, or partially differentiated before deposition in the BBB-on-chip with further differentiated within the BBB-on-chip. The BBB-on-chip may promote the differentiation and/or maturation of any of the involved cell types. This may be accomplished, for example, by the microenvironment generated by or present within the BBB-on-chip (e.g. cell-cell signaling, protein coating, fluid flow), by the use of differentiation protocols designed for fluidic culture (e.g. facilitated by flow in microfluidic channels), or combination thereof. Selecting the surface coating is important in order to promote initial cell attachment and viability. Moreover, surface coating may be helpful and sometime necessary in order to select for specific cell populations (e.g. when seeding a mixed population as is commonplace in stem-cell derived cells) and/or to provide differentiation or maturation signals to the cells. The effects or success of surface coatings can vary depending on the underlying substrate. Accordingly, the results illustrated in FIG. 50 correspond to a PDMS substrate.

Table 1 shows various conditions tested for seeding neural (EZ spheres, iNPCs and iMNPs) and endothelial cells (iBMECs) on the apical and basal sides of a microfluidic chip. This chip comprised a porous membrane separating a top fluidic channels and bottom fluidic channel (the chip was modeled after an embodiment disclosed in U.S. Pat. No. 8,647,861 without the optional vacuum operating channels). In typical embodiments of the present disclosure that comprise a porous membrane, any brain cells (e.g. astrocytes, neurons) are disposed within the said top fluidic channel, and endothelial cells (e.g. iBMECs, primary BMECs, HUVECs) are disposed within the said bottom fluidic channel. In other embodiments, however, endothelial cells are disposed within the top fluidic channel and brains cells are disposed within the bottom fluidic channel, while in yet other embodiments, both endothelial and brain cells are disposed within the same fluidic channel (top, bottom or both).

Tables 2 and 3 show various conditions tested for seeding fresh neural cells (iMNPs) and fresh endothelial cells (iBMECs), where the particular conditions are associated by microfluidic chip number, allowing for a correlation of good tight junctions with the seeding conditions. Chips can be seeded with a variety of seeding density, with the optimal density determined by factors including (but not limited) to cell type, stage of differentiation, surface coating, substrate material, media composition, whether the cells proliferate after seeding, seeding incubation time, channel dimensions, etc. Seeding densities for neural cells including EZ spheres, iNPCs, and iMNPs in the device illustrated in Table 1 can range, for example, between $1 \times 10^3$ cells/mL and $1 \times 10^8$ cells/mL or between $1 \times 10^4$ cells/mL and $5 \times 10^8$ cells/mL. Seeding densities for endothelial cells including iBMECs in the device illustrated in Table 1 can range, for example, between $2.5 \times 10^3$ cells/mL and $1 \times 10^8$ cells/mL or between $2 \times 10^4$ cells/mL and $5 \times 10^8$ cells/mL.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4C is a vertical 2D projection of a 3D confocal stack of images slices, which allows for visualization of the neurons and endothelial cells together, even though they are not in the same plane on the microfluidic device.

FIGS. 9A and C show the results for Chip 664 where BMECs (on collagen/fibronectin) and iMPs (on wet laminin) were co-cultured. FIGS. 9B and D show the results for Chip 663 where iMPs (on laminin) were cultured alone.

FIG. 12A shows the results/readout from transepithelial electrical resistance (TEER) measurements on the microfluidic chip under flow, static, and control conditions. Clearly, flow is important for optimum results. FIG. 12B show TEER measurements on transwells. TEER is a typical measure of in vitro BBB models and is used both for evaluating the model as well as an experimental readout (e.g. after subjecting the BBB model to an experimental condition). Some aspects of the present invention include measuring the TEER of one or more BBB-on-chips. This can be done, for example, to evaluate BBB-on-chip development, maturation or quality, as a readout for experiments involve an introduced agent, as a readout for experiments involving specific cells or cell types (e.g. patient specific, a disease population, or treated to simulate a disease or condition), etc. It is known in the art how to integrate electrodes suitable for TEER measurement into microfluidic devices. Douville et al., "Fabrication of Two-Layered Channel System with Embedded Electrodes to Measure Resistance Across Epithelial and Endothelial Barriers" Anal Chem. 2010 March 15; 82(6): 2505-2511.

FIG. 13A is an enlarged schematic view showing how electrodes on the chip were connected, along with pipette tips engaging the chip.

FIG. 17C shows the ratio of T4 to IS on the Y-axis, and T4 transport across the BBB on the X-axis. After flowing patient blood through the microfluidic chips into the channel under the BMECs, it was possible to measure the transport of compounds from the blood into the neural compartment, i.e. through the BMEC barrier. In this case, the experiment included a control set of BBB-on-chips comprising iPS-derived cells originating from a non-diseased individual, and a second set of BBB-on-chips comprising iPS-derived cells originating from a patient diagnosed with Allan-Herndon-Dudley syndrome (AHDS). The mass-spectrometry data in FIG. 17A is an initial experiment to confirm that the MCT8 transporter defect can be recapitulated on an Organ-Chip.

FIG. 18A-B shows electrophysiology recordings collected by patch-clamp from neurons in the microfluidic device ("BBB-on-Chip"). An arrow (FIG. 18A) indicates single action potential. Current recordings (FIG. 18B, right) show negative sodium channel currents (Na t) and positive potassium channel ($K^+$). These measurements on-chip can be used, for example, to provide an indication of neuronal maturation or as a readout of neuron health. In turn, neuronal maturation or health can be used as indicators of BBB-on-chip quality (for example, before starting an experiment) or as an experimental endpoint indicating, for example, that an agent as crossed the BBB, a disease condition has emerged, the BBB has been modified or compromised, or conversely, that the BBB or neural function or health have improved. Patch clamping can be performed on the BBB-on-chip by a variety of methods, including for example, by inserting the patch-clamp electrodes through the soft body of an elastomeric BBB-on-chip device. Similarly to patch-clamping, other electrophysiological readouts can be obtained, for example by including one or more electrodes in the device. In particular, a multi-electrode array (MEA) can be integrated on the membrane of embodiments that possess one or similarly in fluidic channels or cavities within the device. Electrophysiological measurements (patch-clamping, MEA) can also be applied to astrocytes, which have been shown in the art to be excitable.

FIG. 22A is a schematic showing one embodiment of the microfluidic device or chip (16), comprising two microchannels (1), each with an inlet and outlet port (2), as well as (optional) vacuum ports. FIG. 22B is a topside schematic of an embodiment of the perfusion disposable or "pod" (10) featuring the transparent (or translucent) cover (11) over the reservoirs, with the chip (16) inserted in the carrier (17). The chip can be seeded with cells and then placed in a carrier for insertion into the perfusion disposable or pod, whereupon culture media in the reservoirs flows into the microchannels and perfuses the cells (e.g. both BMECs and MNs).

FIG. 23B shows an exploded view of the device of FIG. 23A, showing a bottom piece (97) having channels (98) in a parallel configuration, and a top piece (99) with a plurality of ports (2), with a tissue-tissue interface simulation region comprising a membrane (101) between the top (99) and bottom (97) pieces, where (in one embodiment) cell behavior and/or passage of gases, chemicals, molecules, particulates and cells are monitored. In an embodiment, an inlet fluid port and an outlet fluid port are in communication with the first central microchannel such that fluid can dynamically travel from the inlet fluid port to the outlet fluid port via the first central microchannel, independently of the second central microchannel. It is also contemplated that the fluid passing between the inlet and outlet fluid ports may be shared between the central microchannels. In either embodiment, characteristics of the fluid flow, such as flow rate and the like, passing through the first central microchannel is controllable independently of fluid flow characteristics through the second central microchannel and vice versa.

FIG. 24 is a print out of electrophysiological data from neurons cultured in a microfluidic device or chip, showing highly complex spontaneous activity in a chip.

FIG. 25A-B shows print outs of electrophysiological data from neurons cultured alone (FIG. 25A, top panel) and co-cultured with BMECs (FIG. 25B, bottom panel) in a microfluidic device or chip, showing that neural tissue have more mature electrophysiological properties in the chip, and in co-culture with BMECs.

FIG. 32a Schematic of Spinal neural progenitor (SNP) differentiation from induced pluripotent stem cell (iPSC) cultures. Cells were fated to neural ectoderm (NE) using WNT agonist CHIR99021 and SMAD inhibitors LDN193189 and SB431542 for 6 days then patterned to ventral spinal neurons using Retinoic Acid (RA) and Sonic hedgehog agonist (SAG) in 6-well plates. At day 12, SNPs were frozen, banked and thawed for experiments (Cryobank). SNPs were seeded into the top channel of the SC-chip (dotted line) and incubated for 6 days. FIG. 32b Schematic of dual-channel organ chip seeded with SNPs in top channel. FIG. 32c Phosphorylated neurofilament heavy chain (SMI32) is enriched in spinal motor neurons (spMNs) and expressed in cells populating entire top channel. Scale bar=200 microns. FIG. 32d Immunostaining of main channel of the chip of markers of spMNs SMI32, nuclear marker islet1 (ISL1), Beta 3 tubulin (TUBB3), NKX6.1, neurofilament marker microtubule-associated protein 2 (MAP2), and synaptic marker synaptophysin (SYNP), scale=200 microns (left); 40 microns (right). FIG. 32e Representative image of SC-chip neurons treated with Fluo-4 calcium activated dye and acquired live in FITC channel. FIG. 32f Florescence of individual active neurons normalized to baseline florescence and plotted over time (dF/F). FIG. 32g Raster plot showing detected events of corresponding traces.

FIG. 33a Schematic of dual-differentiation and seeding paradigm in EC/SC-Chip. Both SNPs and BMECs are generated from human iPSCs and seeded into top and bottom channels respectively. Transverse section of the EC/SC-Chip (right) shows two compartments separated by porous membrane. FIG. 33b Immunostaining of whole SC-Chip at 6-days incubation expressing SMI32 in top channel and ISL 1 expressed by BMECs on bottom channel. FIG. 33c Maximum projection images cropped along Z-axis to show top and bottom compartments of seeding end of EC/SC-Chip immunostained with MN markers SMI32 and islet 1 (ISL1), and tight junction marker zona occludens 1 (ZO-1), Scale bar=400 microns (left) 40 microns (right). FIG. 33d Confocal optical reconstruction at along Z axis (top) of SC-Chip exhibits distinct separation of cultures at 6 days separated by porous PDMS membrane. Perspective view (bottom) exhibits confluent layer of BMECs surrounding entire bottom channel, Scale bar=100 microns. FIG. 33e Representative images of cells attached to porous membrane in the main channel (top and bottom planes). SC-Chip was seeded either with SNPs alone in the top channel (SC-Chip) or with the addition of non-GFP BMECs into the bottom compartment (EC/SC-Chip). FIG. 33f High magnification of top compartment show GFP negative, ISL1 positive clusters indicating BMEC infiltration. Quantification of FIG. 33g GFP and FIG. 33h ISL1 populations in top compartment. Error bars represent standard deviation. Plots were determined from 6 individual chips from three culture rounds (dots). No significant difference cultures determined by t-test (ns).

FIG. 34A-H Exemplary SC-Chip environment increases spontaneous neural activity. FIG. 34a Individual Representative calcium transient activity of SNP (top) and BMEC (bottom) cultures acquired at the seeding compartments plotted by change in florescence intensity over background (dF/F) with respect to time totaling 180 seconds. FIG. 34b Calcium transient activity plots of 30 representative neurons from each culture condition. Transient frequency of 194-297 neurons spanning three separate replicates per condition calculated in two individual lines FIG. 34c 83GFP and FIG. 34d 00iCTR. Neuron activity completely ablated with the administration of tetrodotoxin (TTX). FIG. 34e Immunocytochemistry staining of islet 1 (ISL1) and smi32 (right) of site previously acquired for live calcium transients using fluro-4 dye (left). ISL1$^+$ neurons (arrows) superimposed to determine MN firing specificity. FIG. 34f Mean transient frequency of representative active neurons compared to ISL1 overlaid MNs. Charts showing representative transient events from FIG. 34g ISL1 SMI32 double-positive neurons quantified and displayed as raster plot and plotted in FIG. 34h as frequency in hertz (Hz). Means represented by black bars and error bars represent standard error of the mean. Significance calculated by ANOVA,  denotes P<0.01, *=P<0.005, and ****=P<0.001.

FIG. 35A-I Exemplary SC-Chip induces neural differentiation and vascular interaction gene expression. FIG. 35a GFP-MN isolation schematic: nuclear GFP expressing SNPs seeded on top channel with isogenic non-GFP expressing BMECs on bottom. Fluorescence-assisted cell sorting (FACS) conducted on FITC to purify spMNs after BMEC co-culture. FIG. 35b Single population histogram of chips seeded only with non-GFP BMECs (black) or GFP-MNs (green) that defined negative and positive fractions respectively. Number of events displayed on y-axis and FITC intensity on x-axis FIG. 35c Mean RPKM data of purified SC-Chip and EC/SC-Chip cultures normalized to RPKM data from iPSC derived BMECs cultured alone. Canonical markers claudin 5 (CLDN5), occluding (OCLN), Tight junction protein 1 (TJP1), Glut-1 (SLC2A1), von willebrand factor (VWF), Tie2 receptor (TEK), endoglin (ENG), and melanoma cell adhesion molecule (MCAM). FIG. 35d Principle component analysis plots of first two principle components (PC) (top) and PCs 2, and 3 (bottom). Arrows indicate weighting along the axis of each respective PC. FIG. 35e Top 200 ranked genes from each PC displayed as Z-score calculated across all conditions for each row and indicated by colorimetric scale. Each PC was entered into DAVID ontology pathway analysis and top 7 categories listed for each PC. The number of genes (count) in each category is displayed with corrected significance values from DAVID analysis (Bonferonni). FIG. 35f FIG. 35g Differentially expressed genes contributing to the "Response to Protein Stimulus" and "Neural Differentiation" DAVID terms enriched in PC2. RPKM data averaged across sample replicates and normalized to 96W control. (FIG. 35h, FIG. 35i) Differentially expressed genes contributing to "Vascular Development" and "Extracellular Matrix" DAVID terms enriched in PC3.

FIG. 36a PCA comparing expression data of differentially expressed genes from PC2 and PC3 and including in vivo adult laser captured MNs (green), in vivo fetal spinal cord (purple), and in vitro experimental data. FIG. 36b Heatmap of top ranking genes from Dev-PC2 that describe variance in fetal gene expression. Z-score calculated from $Log_2$ RPKM data per gene row and displayed by colorimetric scale. FIG. 36c Mean Somatostatin (SST) expression plotted for each condition, error bars represent standard deviation. FIG. 36d Representative images of 96 well (96W) and SC-Chips co-cultured with BMECs (EC/SC-Chip) immunostained with SST and MN markers SMI32 and ISL1, scale bars=40 microns. FIG. 36e Whole mount image of day 67 human fetal spinal cord (top) immunostained with SST, SMI32 and ISL1. Higher magnification of ventral horn ISL1 positive MN pool (box) co-expressing SST (bottom).

FIG. 37A Schematic of relative emergence of cell types that directly interact with developing human MNs in vivo. FIG. 37B Days 53 and 67 human fetal spinal cords immunostained with neuronal marker neuofilament heavy chain (NFH), BMEC marker glucose transporter 1 (GLUT1), and transcription factor ISL1. High magnification of ventral horns (box) show ISL1 positive MN pools (yellow dotted line). FIG. 37C Images of iPSC-derived BMECs cultured in 96-well plate for 6 days and immunostained with GLUT1, ISL 1, and tight junction markers zona occludens 1 (ZO-1) and Occludin (OCLDN). FIG. 37D Images of SNPs cultured in 96W plate and immunostained with markers of spMNs SMI32, nuclear marker islet1 (ISL1), Beta 3 tubulin (TUBB3), NKX6.1, neurofilament marker microtubule-associated protein 2 (MAP2), and synaptic marker synaptophysin (SYNP).

FIG. 38A-C An Exemplary Comparison Of Gene Expression Showing Density Plots And Comparison Of Datasets. FIG. 38A Density plots of 10,001 genes for each sample for transcriptomic analysis. Quantile normalized data (right). FIG. 38B Pierson correlation coefficient analysis of normalized RPKM datasets displayed by colorimetric scale. FIG. 38C Notch pathway genes differentially expressed in the SC-Chip conditions.

FIG. 39A-B An Exemplary Comparison Of Gene Expression Between Density And Principle Component Analysis (PCA). FIG. 39A Density plots of 10,001 genes of developmental comparison containing adult laser captured MNs (green: peaks on the left), fetal Spinal cord (purple: peaks on the right) and sorted iPSC-derived neurons (black: middle peaks); upper graph. Quantile normalized data (bottom). FIG. 39B PCA analysis of variance across all samples and all 10,001 genes. Adult laser captured MNs (green: upper left dots), fetal Spinal cord (purple: cluster of dots on the left) and sorted iPSC-derived neurons (black: lower left dots). Quantile normalized data (bottom).

FIG. 40A shows a schematic illustration of the histology of a cross section of a brain blood vessel in vivo depicting a blood vessel lumen formed by and surrounded by endothelial cells (EC), a vascular basement membrane separating ECs from pericytes (PC), which in turn are overlain with astrocytes. Kim, et. al., Journal of Cerebral Blood Flow and Metabolism. 2006. FIG. 40B shows one embodiment of a chip in vitro: 1. Upper channel, where the arrow depicts directional fluid flow. 2. Lower channel, where arrow depicts directional fluid flow. 3. Cell layer in upper channel. 4. Enodothelial cell layer in lower channel. 5. Porous Membrane. 6. Optional vacuum chambers for providing membrane stretch.

FIG. 41A shows an exemplary overview (looking up through the lower channel (dark-purple staining of cells) into the upper channel (light-green staining of cells)) demonstrating cell coverage of both channels along with cell morphology. FIG. 41B shows an exemplary micrograph of immunofluorescently labeled cell markers in an enlarged view from FIG. 41A where the two channels begin overlapping. The cells on the upper right in the upper channel are labeled light-green for a GFAP marker. The cells on the upper left in the lower channel are stained for a Phalloidin marker (dark-purple) for cells restricted to the vascular channel. FIG. 41C shows an exemplary micrograph of an immunofluorescently labeled cell marker showing ZO-1 tight junctions (outlines) of endothelial cells in the vascular channel. Nuclei are stained with DAPI (blue). FIG. 41D shows an exemplary micrograph of an immunofluorescently labeled cell marker showing light-green for a GFAP marker in the neuronal channel, as an enlarged view from FIG. 41A. Nuclei are stained with DAPI (blue).

FIG. 42A-B Shows one embodiment of a chip in vitro as a blood brain barrier (BBB) on-chip demonstrating cell morphology of exemplary endothelial cells in the Vascular Compartment (lower channel). FIG. 42A schematic illustration of one embodiment of an On-Chip System showing neuronal cells in a neural compartment (upper channel) and cells lining a vasculature forming a simulated blood vessel in the lower channel as one embodiment for a chip as shown in FIG. 42B. FIG. 42B shows a micrograph demonstrating a cross section of one embodiment of a blood brain barrier on-chip as a 3D-Reconstruction of a Confocal Micrograph Image of fluorescently labeled cells, i.e. neuronal progenitors in the upper channel and HBMECs in the lower channel. As shown in the insert, endothelial cell markers (left to right) show immunofluorescent staining of Glut-1, PECAM-1, Occludin-5, and ZO-1.

FIG. 43A shows exemplary micrographs of fluorescently labeled cells using markers for demonstrating exemplary pericytes (upper micrograph) labeled for alpha-SMA (green) and astrocytes (lower micrograph) labeled for GFAP (red) on-chips.

FIG. 43B shows an exemplary micrograph of a lower power confocal micrograph image of fluorescently labeled cells as in FIG. 43A. Nuclei are stained with DAPI (blue). As shown in the insert, these labeled pericytes and astrocytes are an example of cells illustrated schematically in the neuronal compartment (upper channel) above a vascular channel in one embodiment of a blood brain barrier (BBB) on-chip.

FIG. 44A-C Exemplary micrographs of differentiating iPSC-derived endothelial cells on-chip and an exemplary chart showing that on-chip iPSC-derived endothelial cells form a tighter cell layer simulating a blood brain endothelial barrier. FIG. 44A An exemplary timeline for providing iPSC-derived endothelial cells on-chip. Day 0: exemplary morphology of an iPSC colony stained with GFP showing nuclei (blue). After expansion of iPSc colonies, Day 8-12 Start HBMECs Differentiation. Day 18-22 HBMECs selection for providing HBMECs. FIG. 44B shows a phase contrast micrograph of Human Brain Microvascular Endothelial Cells (HBMECs). FIG. 44C_iPS-derived HBMECs (right column) demonstrates higher and more physiologically-relevant TEER values as compared to a brain endothelial cell-line (left column). $\Omega.cm^2$ vs. Average TEER (ohm.cm$^2$).

FIG. 46A An exemplary chart showing Dextran Diffusion as % Dextran (fluorescence). The majority of dextrin is in the vascular channel. FIG. 46B An exemplary Barrier Function Schematic illustrating the movement of dextrin from the Vascular Channel to the Neuronal Channel.

FIG. 47A-F A Barrier Function test demonstrates exemplary low diffusion of human IgG and albumin but not transferrin indicating intact barrier function of the vasculature in one embodiment of a blood brain barrier (BBB) on-chip. FIG. 47A-B Low diffusion of IgG indicates robust and physiological barrier integrity at the vascular-neuronal interface. FIG. 47C-D Low diffusion of Albumin indicates robust and physiological barrier integrity at the vascular-neuronal interface. FIG. 47E-F High levels of transferrin in the neuronal channel indicates presence of transferrin transporters functionally active on iPS-derived brain endothelial cells. FIGS. 47A, C and E Exemplary charts showing human IgG measured by ELISA, human albumin diffusion as albumin concentration ug/ml, and human transferrn (ELISA), respectively. The majority of human IgG and albumin is in the vascular channel. FIGS. 47B, D and F Illustrate exemplary barrier function schematics illustrating the movement of human IgG, albumin or transferrin, respectively, from the Vascular Channel to the Neuronal Channel.

FIG. 50 shows exemplary ECM Calibration on PDMS 24-well plate. The various conditions (especially related to surface treatment and cell seeding) tested for seeding neural cells (EZ spheres and iMNPs) and endothelial cells (iBMECs), which may optionally originate from frozen stocks of cells.

DESCRIPTION OF THE INVENTION

Figure 1:
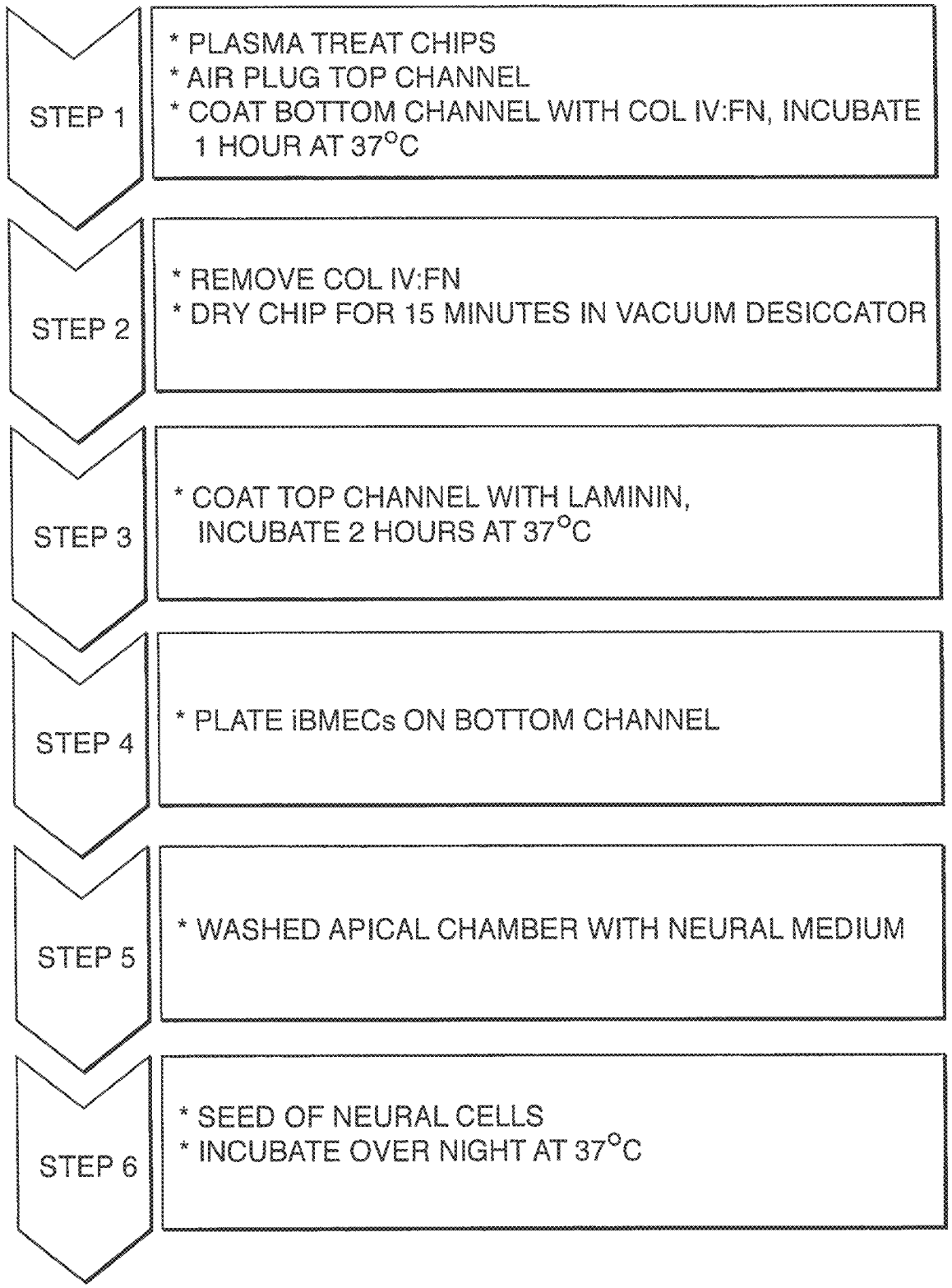
FIG. 1 shows a schematic of one embodiment of a workflow for preparing and seeding a microfluidic chip comprising six steps. This embodiment addresses the different surface coating needs/preferences apparent for iBMECs and iMNPs based on experiments such as those illustrated in FIG. 50 and Table 1. In particular, the workflow aims to provide, in one embodiment, different surface coatings for the top fluidic channel and bottom fluidic channel of the device.

In one embodiment, the invention relates to culturing brain cells and particularly astrocytes together with endothelial cells in a fluidic device under conditions whereby the cells mimic the structure and function of the blood brain barrier and/or spinal cord. Good viability and function allow for measurements of barrier integrity and physiology, whether by trans-epithelial electrical resistance (TEER), patch clamp or other testing measures.

In one embodiment, the invention relates to culturing endothelial cells (preferably brain-related endothelial cells) and optionally astrocytes, optionally neurons, and optionally pericytes in a fluidic device under conditions whereby the cells mimic one or more structural or functional features (e.g. tight junctions) of the blood brain barrier and/or the spinal cord. Culture of these cells in a microfluidic device, such as a microfluidic chip with flow as herein described, whether alone or in combination with other cells, drives maturation and/or differentiation further than existing systems. For example, a mature electrophysiology of the neurons includes negative sodium channel current, positive potassium channel current, and/or action potential spikes of amplitude, duration and frequency similar to neurons in a physiological environment or when compared to static culture neurons, static culture neurons lack one or more of the aforementioned features. The evidence also supports improved maturation of the astrocytes and BMECs.

As described herein, astrocytes were observed to send out of processes to contact the endothelial cells. As described herein, improved and sustained barrier function indicates maturation of the BMECs. Good viability and function allow for measurements of barrier integrity and physiology, whether by TEER, permeability assays, patch clamp (or other electrophysiological methods), calcium or voltage imaging, or other testing measures. Observed characteristics of the in vitro "BBB-on-chip" of the present invention include: (1) tight junctions between endothelial cells (which creates selective permeability to substances); (2) optional cell-to-cell communication exemplified by contact of the endothelial cells with astrocytes (e.g. endfoot contact by partial transmigration of the membrane separating these cells); (3) optional extended neurite projections, (4) optional fluid flow that influences cell differentiation and tight junction formation; and (5) high electrical resistance representing the maturity and integrity of the BBB components. With respect to neurite projections, in one embodiment, the present invention contemplates seeding on nanopatterned surfaces which promote extended and direct (e.g. along a relatively linear path) neurite growth. The preferred nanopattern is linear valleys and ridges, but alternatives such as circular, curved, or any other desired shape or combination thereof are also contemplated. With respect to endothelial cells, in one embodiment, the present invention contemplates BMECs which form a lumen on the chip (for example, completely lining a flow channel, at least for a portion of its length). Among other advantage (e.g. endothelial layer stability) this potentially enables the use of the device with blood or blood components. With respect to selective permeability, the present invention contemplates, in one embodiment, introducing substances in a channel under the BMECs such that at least one substance passes through the BMEC barrier (e.g. BMEC cells on the bottom side of the membrane) and into a channel above the membrane, and detecting said at least one substance (e.g. with antibodies, mass spec, etc.).

Figure 40A:
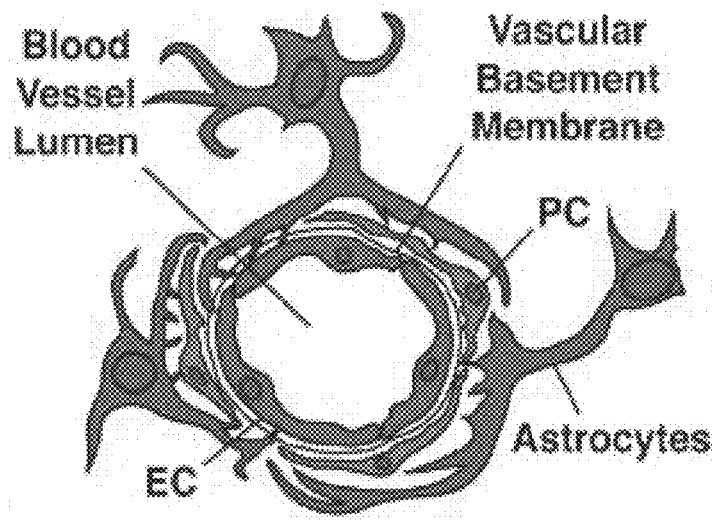
FIG. 40A-B Exemplary schematic illustrations of a brain blood vessel in vivo and a microfluidic chip in vitro.
Figure 40B:
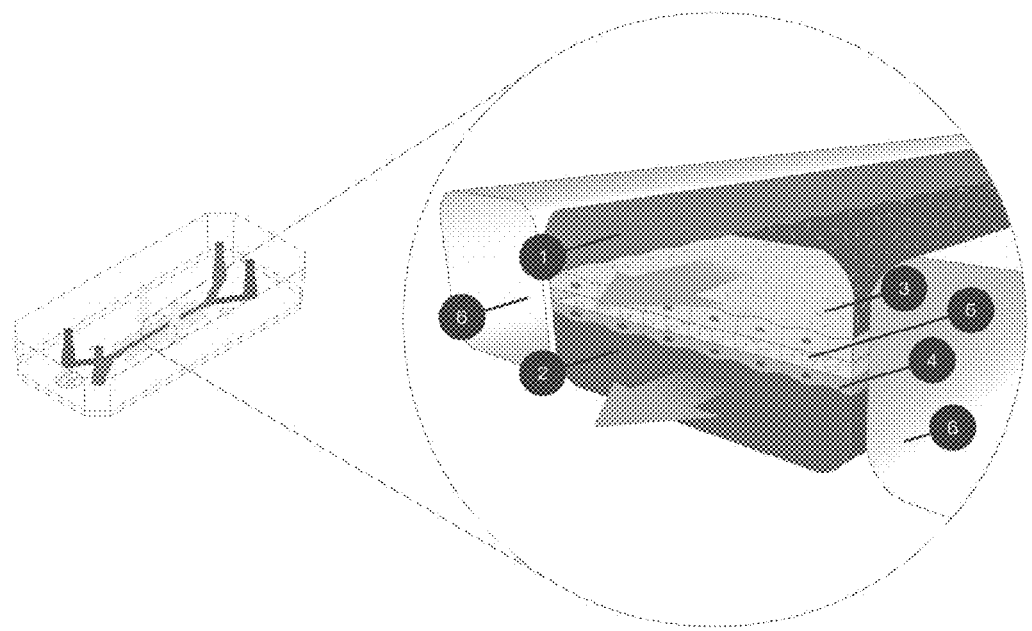

More specifically, cells for use on-chip include but are not limited to brain microvascular endothelial cells, astrocytes, and pericytes. Brain microvascular endothelial cells, for example, may be iPSc derived (e.g. 83i cells from a patient used for some of the experiments as described herein). Astrocytes and pericytes for use on-chips may be obtained as primary cells. In some embodiments, primary astrocytes and primary pericytes may be obtained from explants, i.e. biopsies, of patients, purchased commercially, e.g., from ScienCell (6076 Corte Del Cedro Carlsbad, CA 92011). As exemplary primary cells offered by ScienCell, astrocytes are isolated from human brain (cerebral cortex) then cryopreserved at passage one for delivery as a frozen stock. As another example, pericytes are isolated from Human Brain Vascular areas then offered for sale by ScienCell as a frozen cell pellet. One or more of these cell types are added to microfluidic chips. See, FIG. 40A-B Exemplary schematic illustrations of a brain blood vessel in vivo and a microfluidic chip in vitro. FIG. 40A shows a schematic illustration of the histology of a cross section of a brain blood vessel in vivo depicting a blood vessel lumen formed by and surrounded by endothelial cells (EC), a vascular basement membrane separating ECs from pericytes (PC), which in turn are overlain with astrocytes. Kim, et. al., Journal of Cerebral Blood Flow and Metabolism. 2006. FIG. 40B shows one embodiment of a chip in vitro: 1. Upper channel, where the arrow depicts directional fluid flow. 2. Lower channel, where arrow depicts directional fluid flow. 3. Cell layer in upper channel. 4. Enodothelial cell layer in lower channel. 5. Porous Membrane. 6. Optional vacuum chambers for providing membrane stretch. In some embodiments, membrane stretch may be used to mimic movement of blood vessels within a living organism.

In some embodiments, methods for seeding cells on-chip are provided, as follows for one example: Day—1: Activate and Coat Chips, Day 0: Seed HBMECs, Astrocytes and Pericytes.; Day 1: Initiate flow of media @60 µl/hr. Bottom channel only or Top and bottom channels.; Day 2: Initiate permeability assay: Dextran+ Serum proteins+ Compounds of interest.; Day 3: End permeability assay. Collect media and freeze.; Day 4: Test permeability modulators/experimental stimuli Day 5: Repeat permeability assay.; Day 6: End permeability assay—Collect media and freeze. Fix or lyse chips.

Exemplary embodiments of cells on-chip, e.g. HBMECs, astrocytes and pericytes, are provided in the following figures.

Figures 41A, 41B, 41C, 41D:
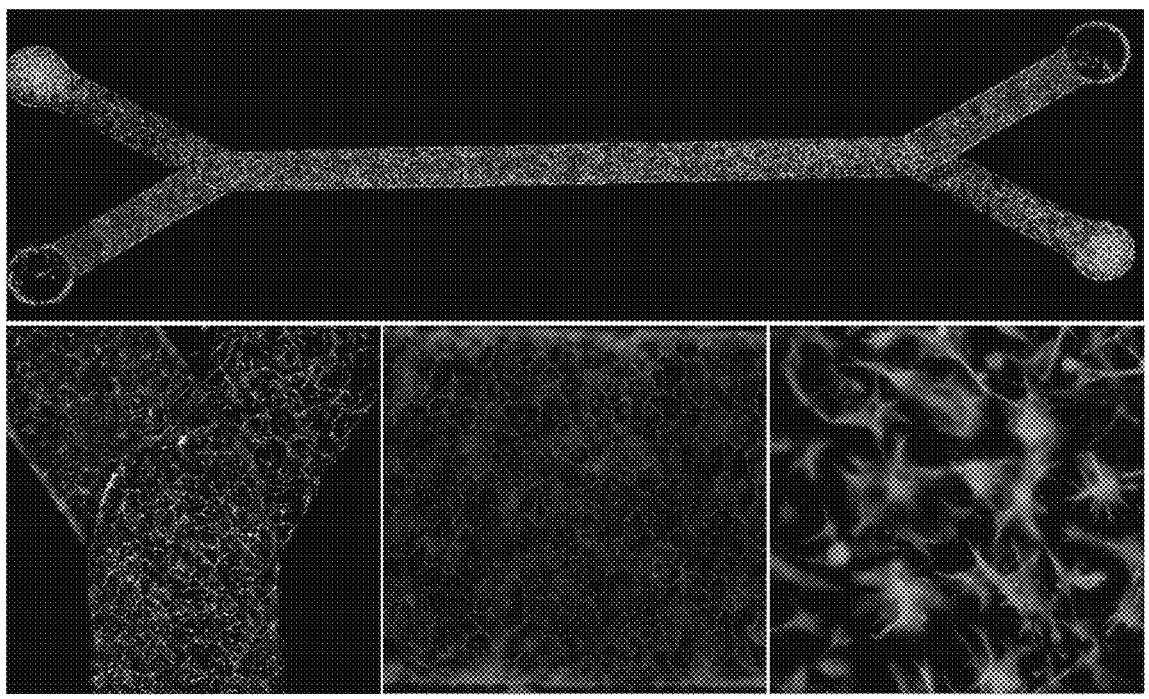
FIG. 41A-D Shows one embodiment of a chip in vitro as a blood brain barrier (BBB) on-chip demonstrating exemplary micrographs of immunofluorescently labeled cells in neuronal and vascular channels.

FIG. 41A-D Shows one embodiment of a chip in vitro as a blood brain barrier (BBB) on-chip demonstrating exemplary micrographs of immunofluorescently labeled cells in neuronal and vascular channels. FIG. 41A shows an exemplary overview (looking up through the lower channel (dark-purple staining of cells) into the upper channel (light-green staining of cells)) demonstrating cell coverage of both channels along with cell morphology. FIG. 41B shows an exemplary micrograph of immunofluorescently labeled cell markers in an enlarged view from FIG. 41A where the two channels begin overlapping. The cells on the upper right in the upper channel are labeled light-green for a GFAP marker. The cells on the upper left in the lower channel are stained for a Phalloidin marker (dark-purple) for cells restricted to the vascular channel. FIG. 41C shows an exemplary micrograph of an immunofluorescently labeled cell marker showing ZO-1 tight junctions (outlines) of endothelial cells in the vascular channel. Nuclei are stained with DAPI (blue). FIG. 41D shows an exemplary micrograph of an immunofluorescently labeled cell marker showing light-green for a GFAP marker in the neuronal channel, as an enlarged view from FIG. 41A. Nuclei are stained with DAPI (blue).

FIG. 42A-B Shows one embodiment of a chip in vitro as a blood brain barrier (BBB) on-chip demonstrating cell morphology of exemplary endothelial cells in the Vascular Compartment (lower channel). FIG. 42A schematic illustration of one embodiment of an On-Chip System showing neuronal cells in a neural compartment (upper channel) and cells lining a vasculature forming a simulated blood vessel in the lower channel as one embodiment for a chip as shown in FIG. 42B. FIG. 42B shows a micrograph demonstrating a cross section of one embodiment of a blood brain barrier on-chip as a 3D-Reconstruction of a Confocal Micrograph Image of fluorescently labeled cells, i.e. neuronal progenitors in the upper channel and HBMECs in the lower channel. As shown in the insert, endothelial cell markers (left to right) show immunofluorescent staining of Glut-1, PECAM-1, Occludin-5, and ZO-1.

Figure 43A:
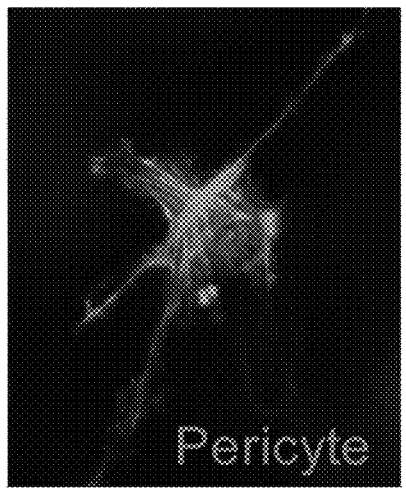
FIG. 43A-B Shows one embodiment of a chip in vitro as a blood brain barrier (BBB) on-chip demonstrating cell morphology of exemplary pericytes and astrocytes as part of a neural compartment (upper channel).
Figure 43A:
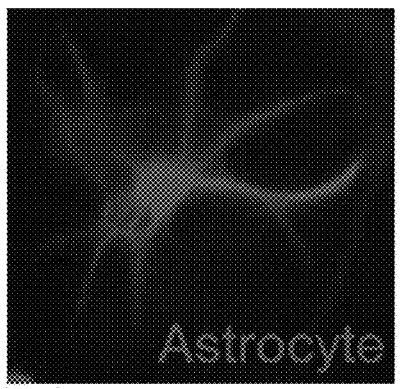
Figure 43B:
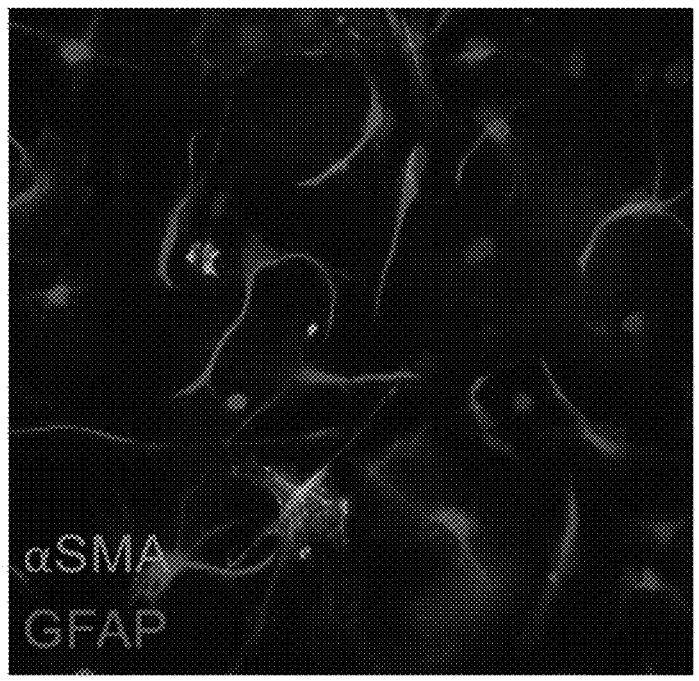
Figure 43B:
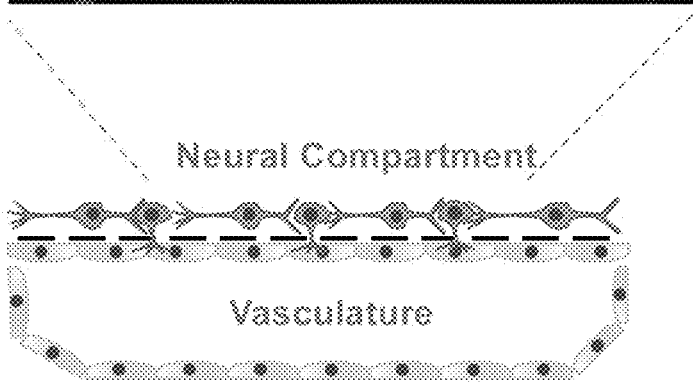

FIG. 43A-B Shows one embodiment of a chip in vitro as a blood brain barrier (BBB) on-chip demonstrating cell morphology of exemplary pericytes and astrocytes as part of a neural compartment (upper channel). FIG. 43A shows exemplary micrographs of fluorescently labeled cells using markers for demonstrating exemplary pericytes (upper micrograph) labeled for alpha-SMA (green) and astrocytes (lower micrograph) labeled for GFAP (red) on-chips. FIG. 43B shows an exemplary micrograph of a lower power confocal micrograph image of fluorescently labeled cells as in FIG. 43A. Nuclei are stained with DAPI (blue). As shown in the insert, these labeled pericytes and astrocytes are an example of cells illustrated schematically in the neuronal compartment (upper channel) above a vascular channel in one embodiment of a blood brain barrier (BBB) on-chip.

Figure 44C:
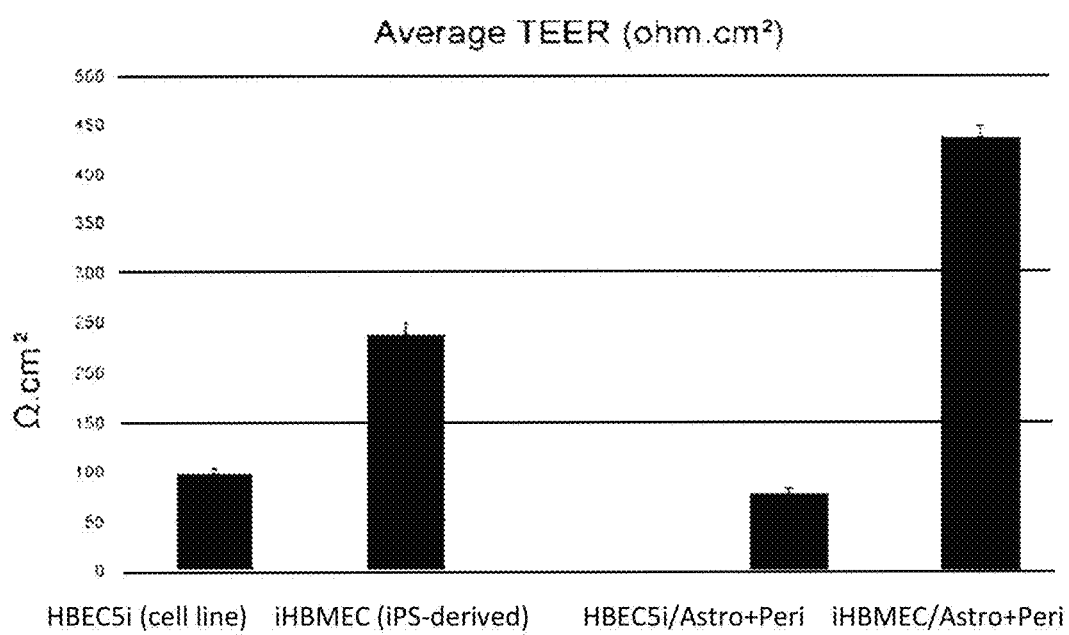

FIG. 44A-C Exemplary micrographs of differentiating iPSC-derived endothelial cells on-chip and an exemplary chart showing that on-chip iPSC-derived endothelial cells form a tighter cell layer simulating a blood brain endothelial barrier. FIG. 44A An exemplary timeline for providing iPSC-derived endothelial cells on-chip. Day 0: exemplary morphology of an iPSC colony stained with GFP showing nuclei (blue). After expansion of iPSc colonies, Day 8-12 Start HBMECs Differentiation. Day 18-22 HBMECs selection for providing HBMECs. FIG. 44B shows a phase contrast micrograph of Human Brain Microvascular Endothelial Cells (HBMECs). FIG. 44C iPS-derived HBMECs (right blue column) demonstrates higher and more physiologically-relevant TEER values as compared to a brain endothelial cell-line (left grey column). $\Omega.cm^2$ vs. Average TEER (ohm.cm$^2$).

Figure 45:
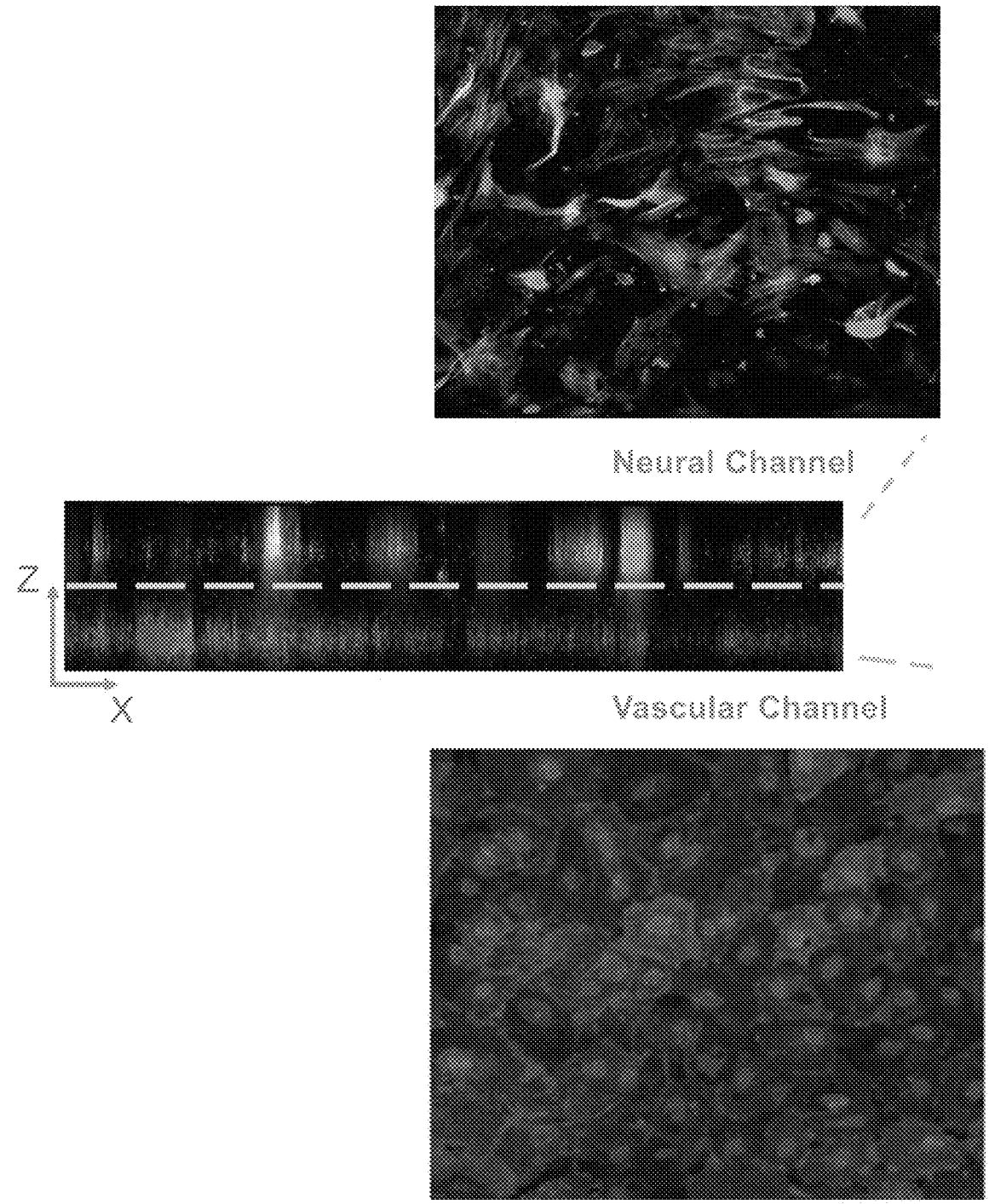
FIG. 45 Shows one embodiment of a chip in vitro as a blood brain barrier (BBB) on-chip demonstrating cells expressing typical markers of Astrocytes, Pericytes and HMBECs after 5 days on-chip. Middle fluorescent confocal micrograph shows a cross section of cells on a chip. Upper fluorescent confocal micrograph at a higher magnification shows cell morphology of exemplary pericytes (αSMA-red) and astrocytes (GFAP-green) as part of a neural compartment (upper neuronal channel). Nuclei are stained with DAPI (blue). Lower fluorescent confocal micrograph at a higher magnification shows cell morphology of exemplary endothelial cells (iHBMEC (Glut1-red) as part of a vascular compartment (lower vascular channel). Nuclei are stained with DAPI (blue).

FIG. 45 Shows one embodiment of a chip in vitro as a blood brain barrier (BBB) on-chip demonstrating cells expressing typical markers of Astrocytes, Pericytes and HMBECs after 5 days on-chip. Middle fluorescent confocal micrograph shows a cross section of cells on a chip. Upper fluorescent confocal micrograph at a higher magnification shows cell morphology of exemplary pericytes (αSMA-red) and astrocytes (GFAP-green) as part of a neural compartment (upper neuronal channel). Nuclei are stained with DAPI (blue). Lower fluorescent confocal micrograph at a higher magnification shows cell morphology of exemplary endothelial cells (iHBMEC (Glut1-red) as part of a vascular compartment (lower vascular channel). Nuclei are stained with DAPI (blue).

Figure 46A:
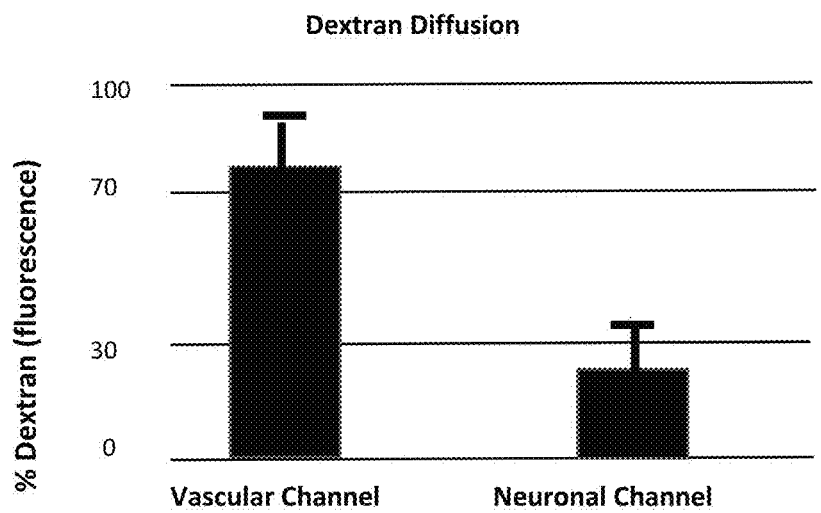
FIG. 46A-B A Barrier Function test using Fluorescent Dextran (3 kDa) demonstrates exemplary low diffusion of Dextran indicating intact barrier function of the vasculature in one embodiment of a blood brain barrier (BBB) on-chip.
Figure 46B:
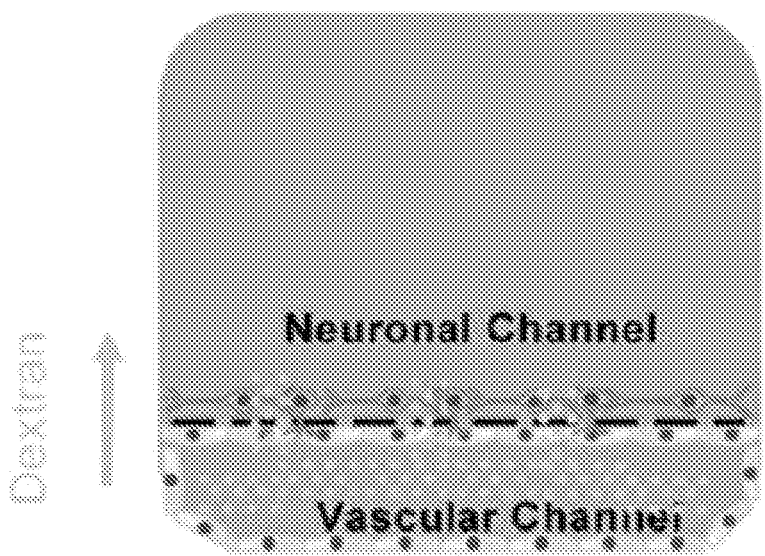

FIG. 46A-B A Barrier Function test using Fluorescent Dextran (3 kDa) demonstrates exemplary low diffusion of Dextran indicating intact barrier function of the vasculature in one embodiment of a blood brain barrier (BBB) on-chip. FIG. 46A An exemplary chart showing Dextran Diffusion as % Dextran (fluorescence). The majority of dextrin is in the vascular channel. FIG. 46B An exemplary Barrier Function Schematic illustrating the movement of dextrin from the Vascular Channel to the Neuronal Channel.

In some embodiments, an IgG-to-albumin ratio (i.e. Albumin Ratio), see, data in FIG. 47A-F, is used as a diagnostic for clinical relevance. (www.mayomedicallaboratories.com/test-catalog/Overview/33038). As one on-chip example, IgG:Albumin in neuronal channel of one embodiment of a BBB On-Chip=0.005. According to Mayo Clinic resources, an IgG:Albumin in CSF in vivo=0.0-0.21. Thus, the IgG-to-albumin ratio on-chip is within a normal range. An increase in this index in vivo is a reflection of IgG accumulation in the CNS. For one clinical example, an IgG:Albumin ratio is used as a marker for CNS inflammatory diseases, such as Multiple Sclerosis. Thus, in additional embodiments, comparative IgG:Albumin ratios are contemplated for modeling CNS inflammatory diseases on-chip.

Figure 47A:
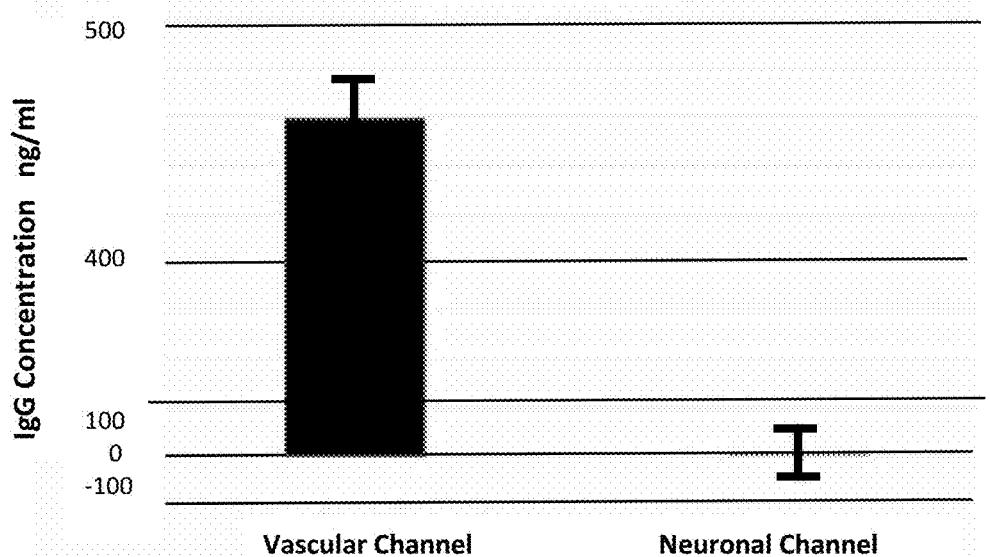
Figure 47C:
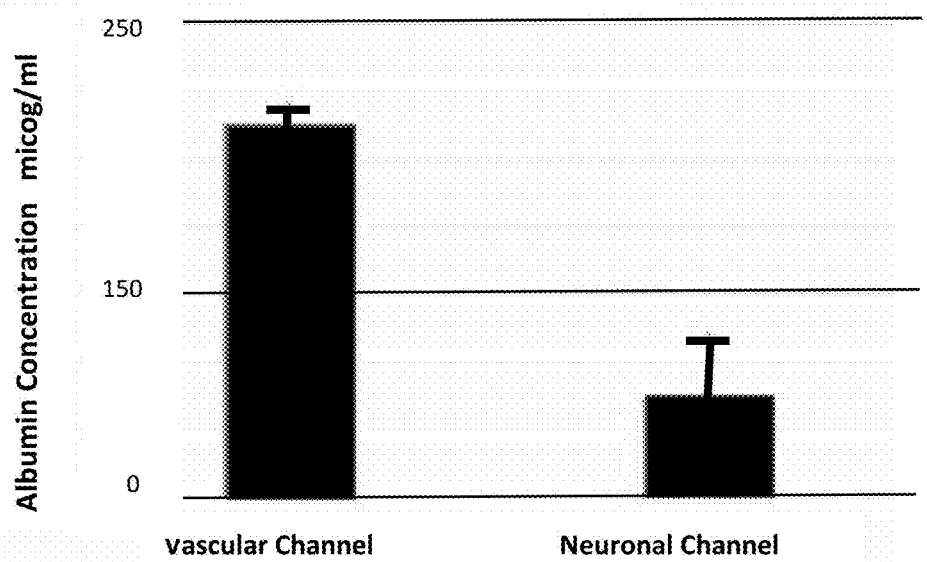
Figure 47B:
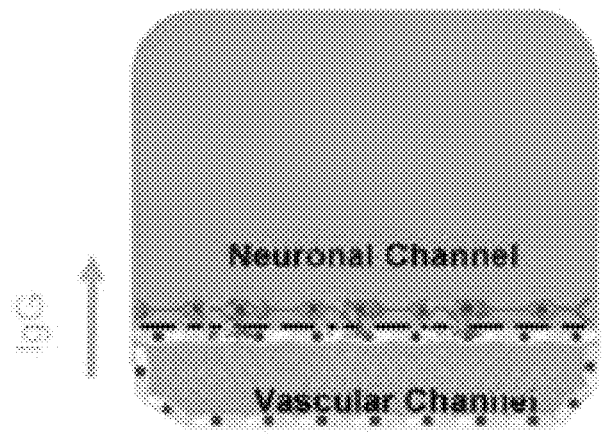
Figure 47D:
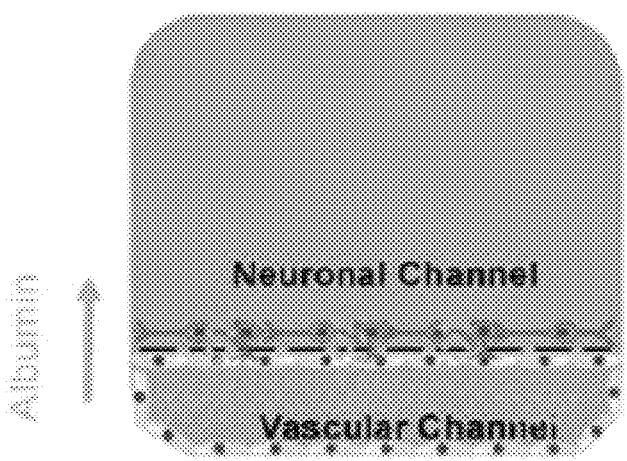
Figure 47F:
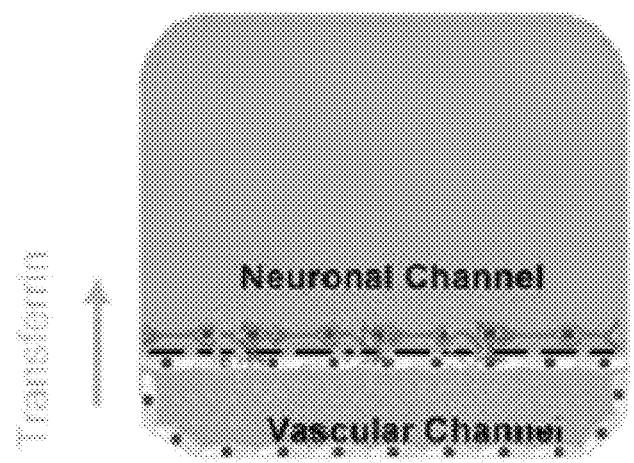

FIG. 47A-F A Barrier Function test demonstrates exemplary low diffusion of human IgG and albumin but not transferrin indicating intact barrier function of the vasculature in one embodiment of a blood brain barrier (BBB) on-chip. FIG. 47A-B Low diffusion of IgG indicates robust and physiological barrier integrity at the vascular-neuronal interface. FIG. 47C-D Low diffusion of Albumin indicates robust and physiological barrier integrity at the vascular-neuronal interface. FIG. 47E-F High levels of transferrin in the neuronal channel indicates presence of transferrin transporters functionally active on iPS-derived brain endothelial cells. FIGS. 47A, C and E Exemplary charts showing human IgG measured by ELISA, human albumin diffusion as albumin concentration ug/ml, and human transferrn (ELISA), respectively. The majority of human IgG and albumin is in the vascular channel. FIGS. 47B, D and F Illustrate exemplary barrier function schematics illustrating the movement of human IgG, albumin or transferrin, respectively, from the Vascular Channel to the Neuronal Channel.

In some embodiments, on-chip cells are contemplated for treating with inflammatory agents, such as 1L-13, IFN-gamma, etc., for inducing inflammation on-chips. In some embodiments, on-chip cells are subjected to shear forces. In some embodiments, on-chip pericyte and/or astrocyte cells further include neuronal cells. In some embodiments, a panel of compounds are contemplated for use in testing permeability across the blood brain barrier on-chip. In further embodiments, cell cultures on-chip are contemplated to extend up to 14 days.

Although there is a strong need for a model of the human blood-brain barrier, it is also desirable to develop models of blood-brain barriers of other organisms (not limited to animals). Of particular interest are models of, for example, mouse, rat, dog, and monkey, as those are typically used in drug development. Accordingly, the BBB-on-chip can make advantage of not only human-derived cells but also cells from other organisms. Moreover, although it is preferable that all cell types used originate from the same species (for example, in order to ensure that cell-cell communication is effective), it may be desirable at time to mix species (for example, if a desired cell type is scarce or possess technical challenges).

In some embodiments, neuronal progenitor cells are MN progenitor cells, including but not limited to spinal MN cells. In fact, one of the discoveries during the development of the present inventions found that spinal cord progenitor motor neuron cells on-chip accelerates neuronal maturation in vitro.

Some human stem cell derived models of neurodegenerative diseases are limited by the lack of systems for providing mature functioning cells in vitro. For more accurate modeling with clinical applications, in part, large numbers of maturing functional neuronal cells are needed, in addition to having standard culture methods for accurate comparative analysis and drug testing.

In vivo, developing neurons interact with multiple non-neuronal cell types and extracellular substrates along with receiving extracellular signals as the developing neurons mature and migrate into their biological niche.

Figure 37A:
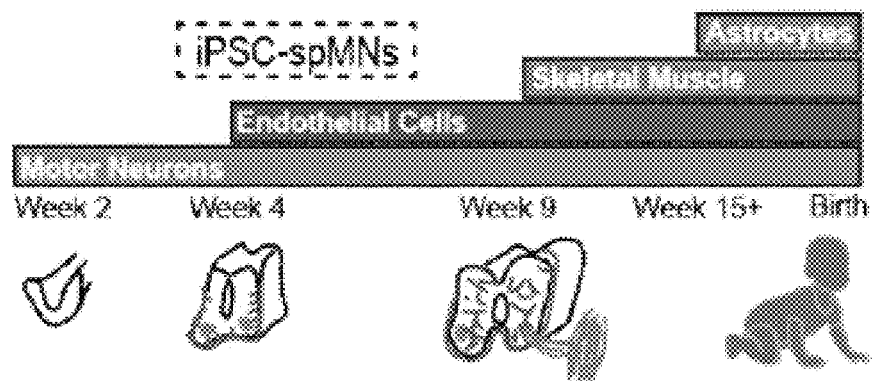
FIG. 37A-D Shows an illustrative comparison of fetal developmental stages (week 2 through birth) to differentiation of specialized cell types, including Motor Neurons, Endothelial Cells, Skeletal Muscle Cells and Astrocytes and examples of cell staining.

In vivo, during neuronal development, brain microvascular endothelial cells (BMECs) invade the neural tube from the perineural vascular plexus beginning at 4 weeks post-fertilization (PF), preceding astrocyte emergence, and form a primitive blood brain barrier that directly interacts with developing neural tube neurons and progenitors (Kurz, 2009; Engelhardt and Liebner, 2014) (FIG. 37a). During development, vascular angiogenesis and axon neurite outgrowth share common morphogenic mechanisms known as angioneurins (Zacchigna, Lambrechts, et al., 2008, Walchli, Wacker, et al., 2015). Brain Microvascular endothelial cells (BMECs) as described herein, share many common signaling pathways with neurons early in development. However, there is much speculation in relation to their contribution to human neuronal maturation. Thus, concordant developmental timing of the two cell types in vivo, as well as shared developmental signaling pathways supported testing a microfluidic chip containing BMECS derived from iPSCs combined with iPSC-derived MN cultures in vitro.

Thus, a microfluidic chip was developed for combining iPSC derived neuronal progenitor motor neuron cells with BMECs. In one example, induced pluripotent stem cells were used to derive spinal motor neuron progenitor cells. In another example, induced pluripotent stem cells were used to derive brain microvascular endothelial cells. During the development of the present inventions, neurons cultured alone in a chip microvolume, i.e. one channel, displayed increased calcium transient function and chip-specific gene expression compared to equivalent cell samples cultured in 96 well plates. In contrast, BMECs seeded into a distinct channel in the chip with neuronal progenitor cells seeded into the other channel of a 2-channel microfluidic chip, were seen to directly contact developing neural cells. This cellular interaction associated neural function was further enhanced over the single channel neuronal progenitor cultures as demonstrated by vascular-neural interactions and expression of niche genes. Moreover, transcriptomic comparisons to fetal and adult spinal cord tissue revealed enhanced in vivo-like signatures arising from the chip co-cultures.

Exemplary embodiments of cells on-chip, e.g. HBMECs and neuronal progenitor cells, are provided in the following figures.

Figure 32A:
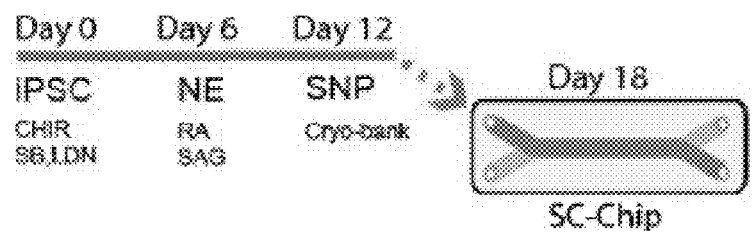
FIG. 32A-G Exemplary Spinal Neural Progenitor (SNP) Neurons Survive And Mature In The Chip Microenvironment.
Figure 32B:
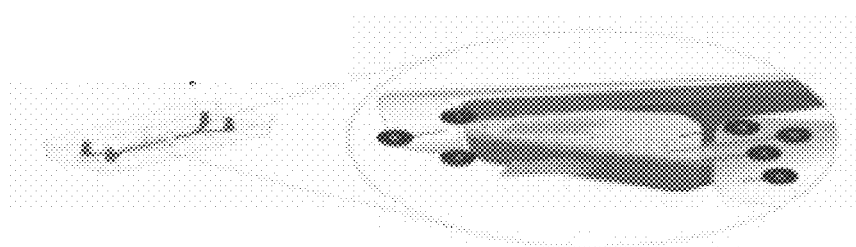
Figure 32C:
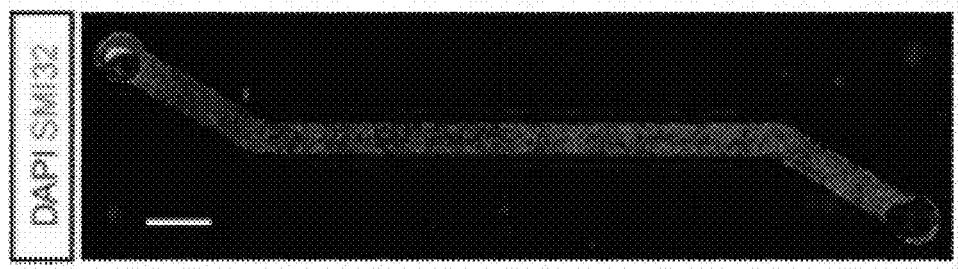
Figure 32D:
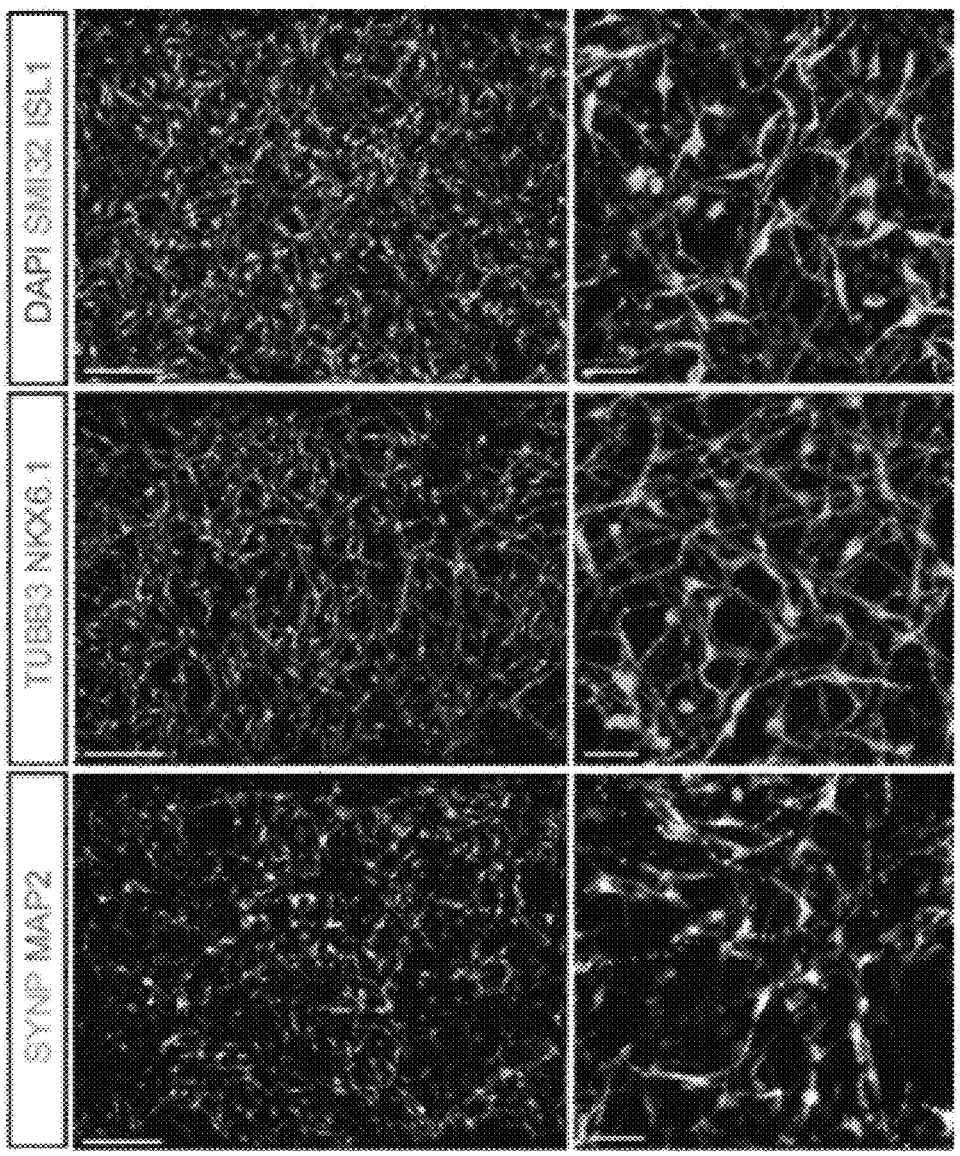
Figure 32E:
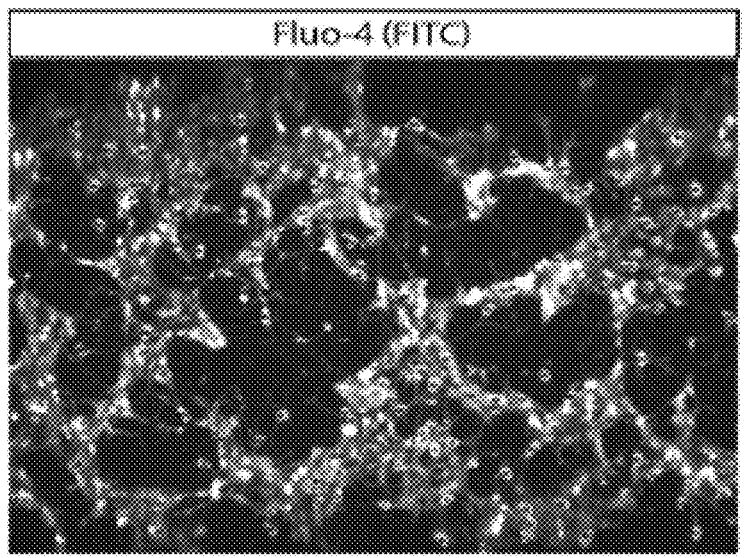
Figure 32F:
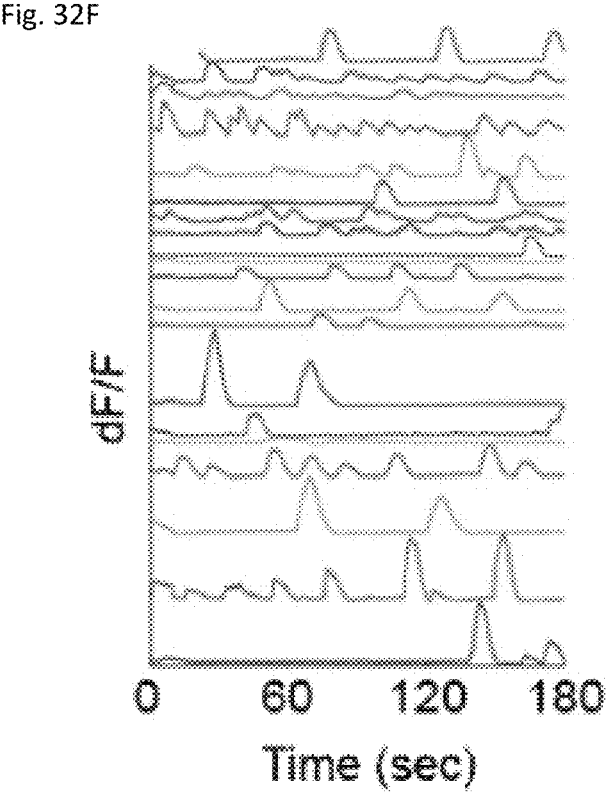
Figure 32G:
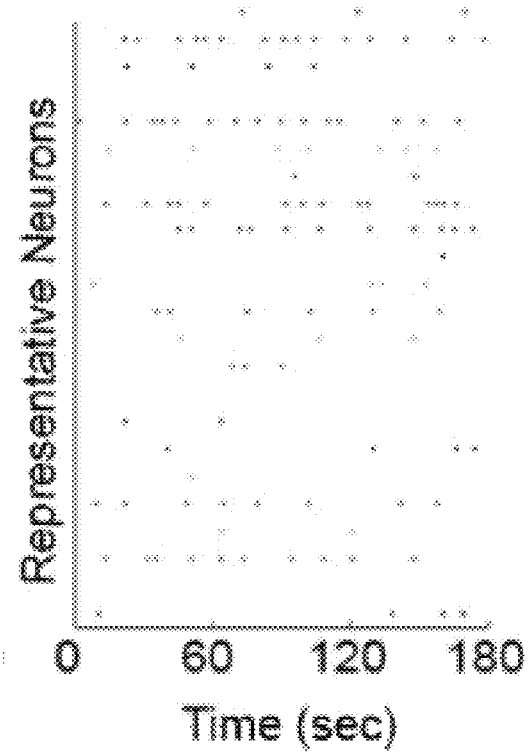

FIG. 32A-G Exemplary Spinal Neural Progenitor (SNP) Neurons Survive And Mature In The Chip Microenvironment. FIG. 32a Schematic of Spinal neural progenitor (SNP) differentiation from induced pluripotent stem cell (iPSC) cultures. Cells were fated to neural ectoderm (NE) using WNT agonist CH1R99021 and SMAD inhibitors LDN193189 and SB431542 for 6 days then patterned to ventral spinal neurons using Retinoic Acid (RA) and Sonic hedgehog agonist (SAG) in 6-well plates. At day 12, SNPs were frozen, banked and thawed for experiments (Cryobank). SNPs were seeded into the top channel of the SC-chip (dotted line) and incubated for 6 days. FIG. 32b Schematic of dual-channel organ chip seeded with SNPs in top channel. FIG. 32c Phosphorylated neurofilament heavy chain (SMI32) is enriched in spinal motor neurons (spMNs) and expressed in cells populating entire top channel. Scale bar=200 microns. FIG. 32d Immunostaining of main channel of the chip of markers of spMNs SMI32, nuclear marker islet1 (ISL1), Beta 3 tubulin (TUBB3), NKX6.1, neurofilament marker microtubule-associated protein 2 (MAP2), and synaptic marker synaptophysin (SYNP), scale=200 microns (left); 40 microns (right). FIG. 32e Representative image of SC-chip neurons treated with Fluo-4 calcium activated dye and acquired live in FITC channel. FIG. 32f Florescence of individual active neurons normalized to baseline florescence and plotted over time (dF/F). FIG. 32g Raster plot showing detected events of corresponding traces.

Figure 33A:
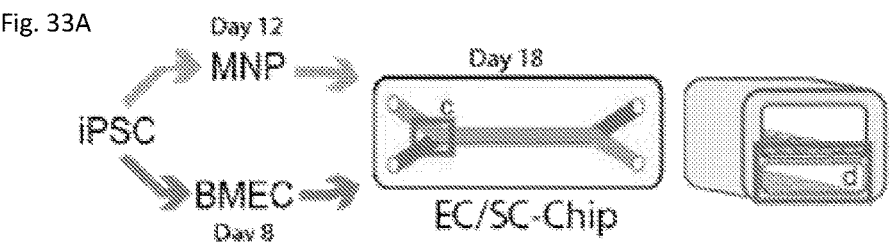
FIG. 33A-H Exemplary Co-culture of iPSC derived MNs and BMECs in SC-Chip.
Figure 33B:
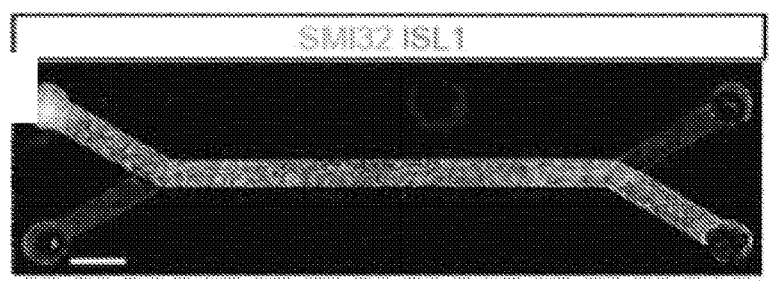
Figure 33C:
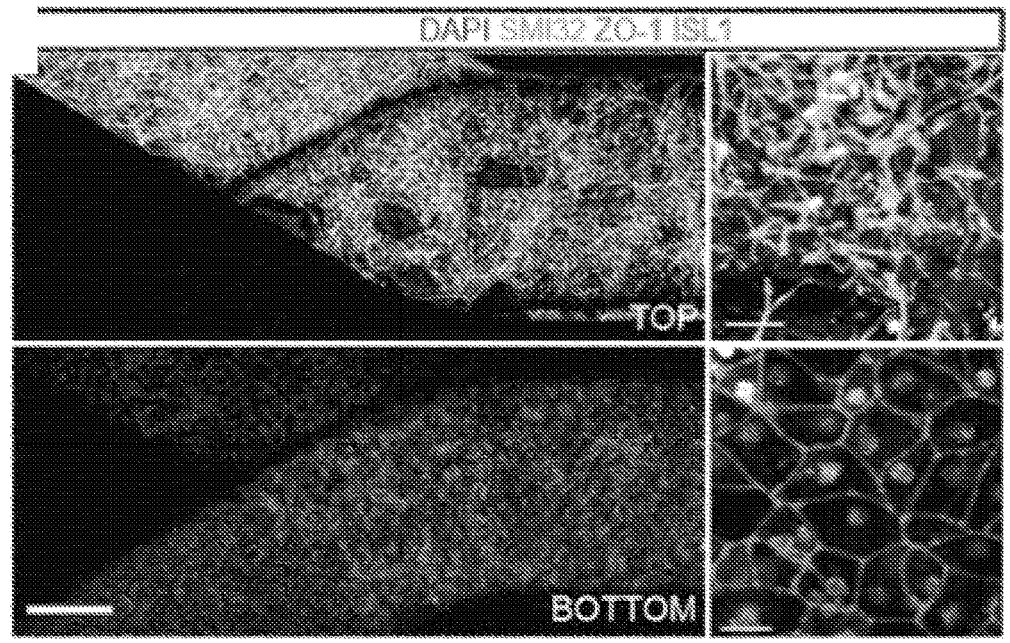
Figure 33D:
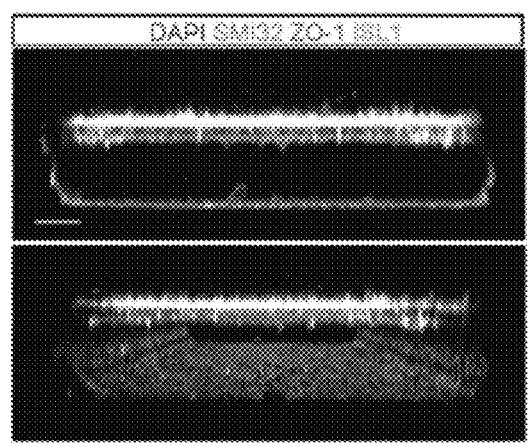
Figure 33E:
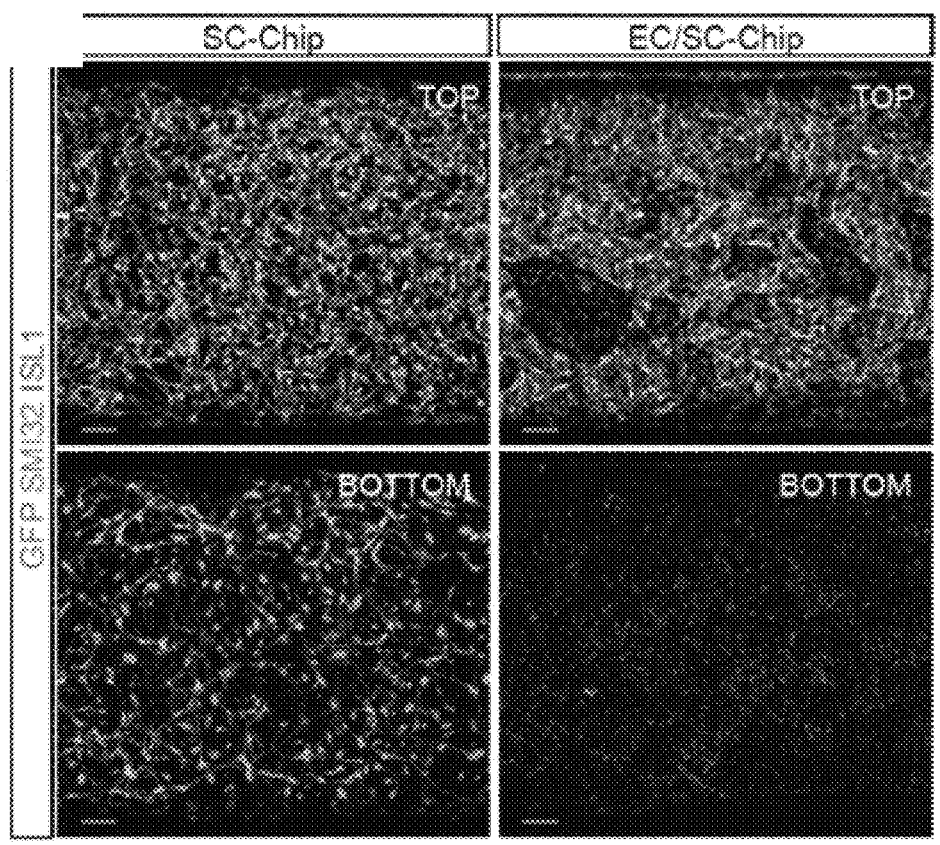
Figure 33F:
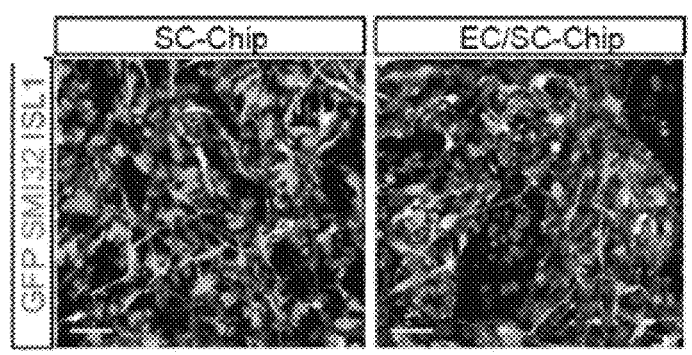
Figure 33G:
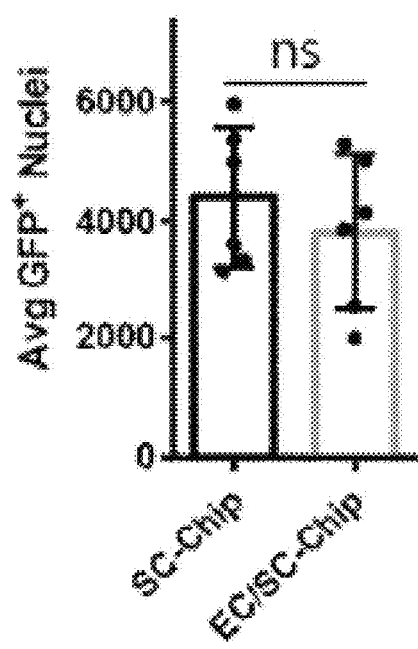
Figure 33H:
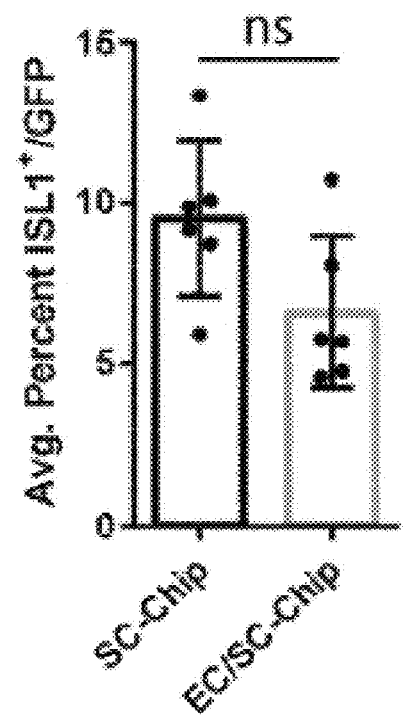

FIG. 33A-H Exemplary Co-culture of iPSC derived MNs and BMECs in SC-Chip. FIG. 33a Schematic of dual-differentiation and seeding paradigm in EC/SC-Chip. Both SNPs and BMECs are generated from human iPSCs and seeded into top and bottom channels respectively. Transverse section of the EC/SC-Chip (right) shows two compartments separated by porous membrane. FIG. 33b Immunostaining of whole SC-Chip at 6-days incubation expressing SMI32 in top channel and ISL1 expressed by BMECs on bottom channel. FIG. 33c Maximum projection images cropped along Z-axis to show top and bottom compartments of seeding end of EC/SC-Chip immunostained with MN markers SMI32 and islet 1 (ISL1), and tight junction marker zona occludens 1 (ZO-1), Scale bar=400 microns (left) 40 microns (right). FIG. 33d Confocal optical reconstruction at along Z axis (top) of SC-Chip exhibits distinct separation of cultures at 6 days separated by porous PDMS membrane. Perspective view (bottom) exhibits confluent layer of BMECs surrounding entire bottom channel, Scale bar=100 microns. FIG. 33e Representative images of cells attached to porous membrane in the main channel (top and bottom planes). SC-Chip was seeded either with SNPs alone in the top channel (SC-Chip) or with the addition of non-GFP BMECs into the bottom compartment (EC/SC-Chip). FIG. 33f High magnification of top compartment show GFP negative, ISL1 positive clusters indicating BMEC infiltration. Quantification of FIG. 33g GFP and FIG. 33h ISL1 populations in top compartment. Error bars represent standard deviation. Plots were determined from 6 individual chips from three culture rounds (dots). No significant difference cultures determined by t-test (ns).

Figure 34B:
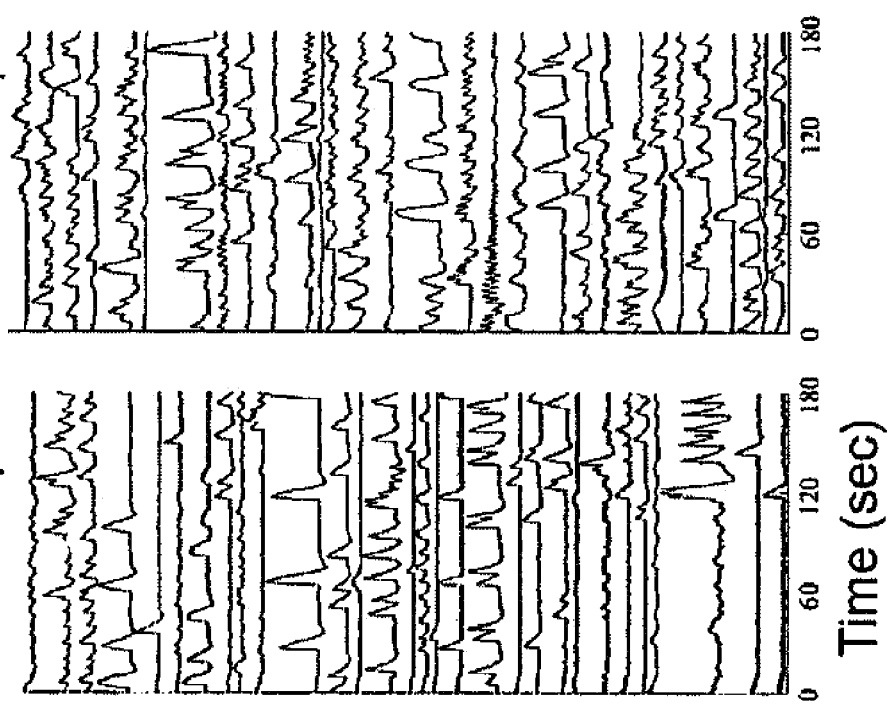
Figure 34A:
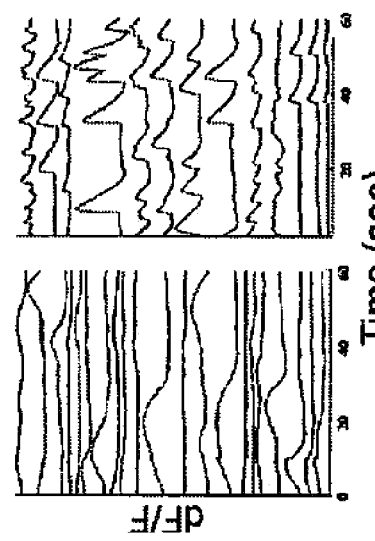
Figure 34C:
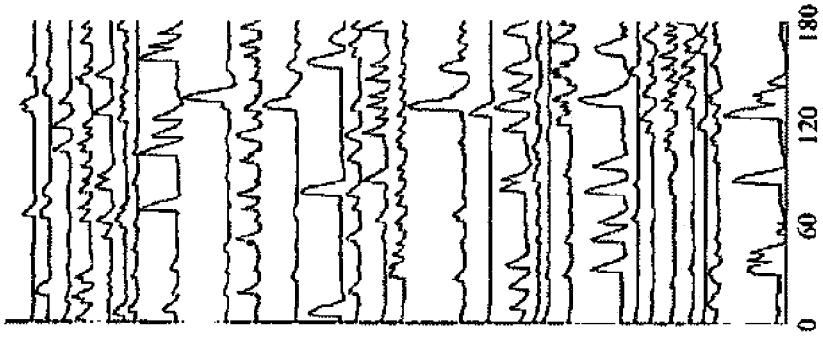
Figure 34E:
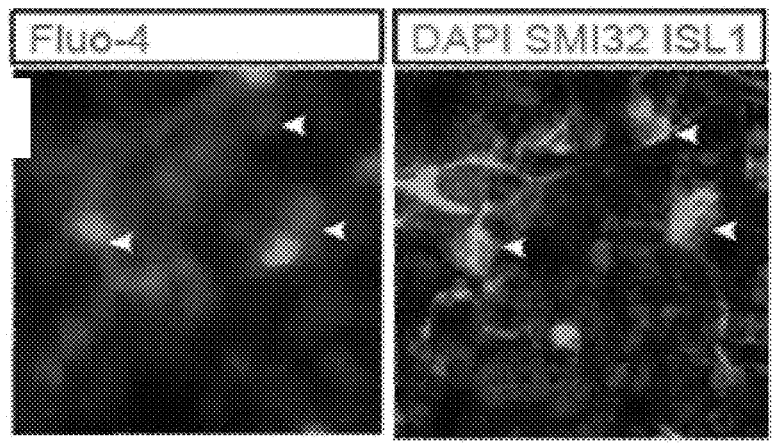
Figure 34F:
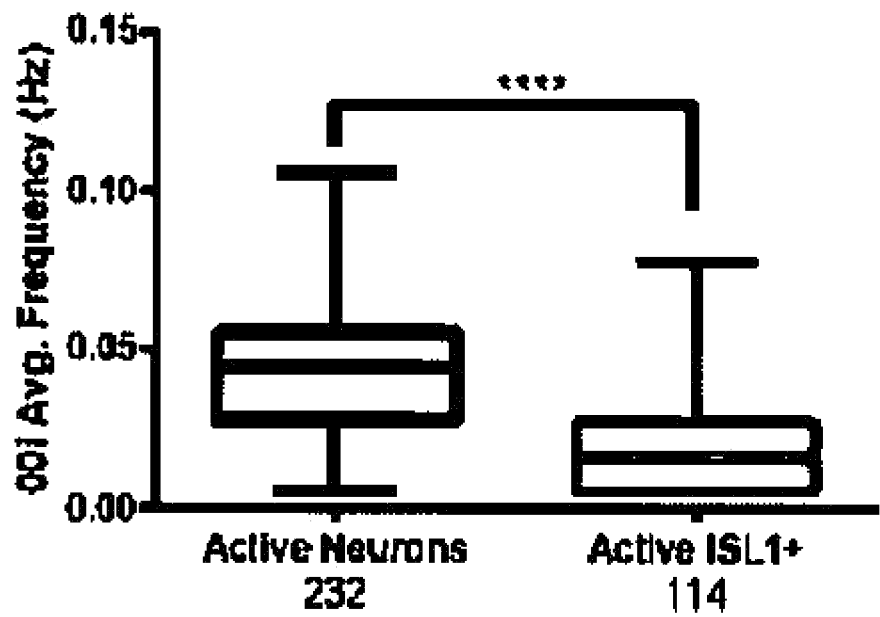
Figure 34G:
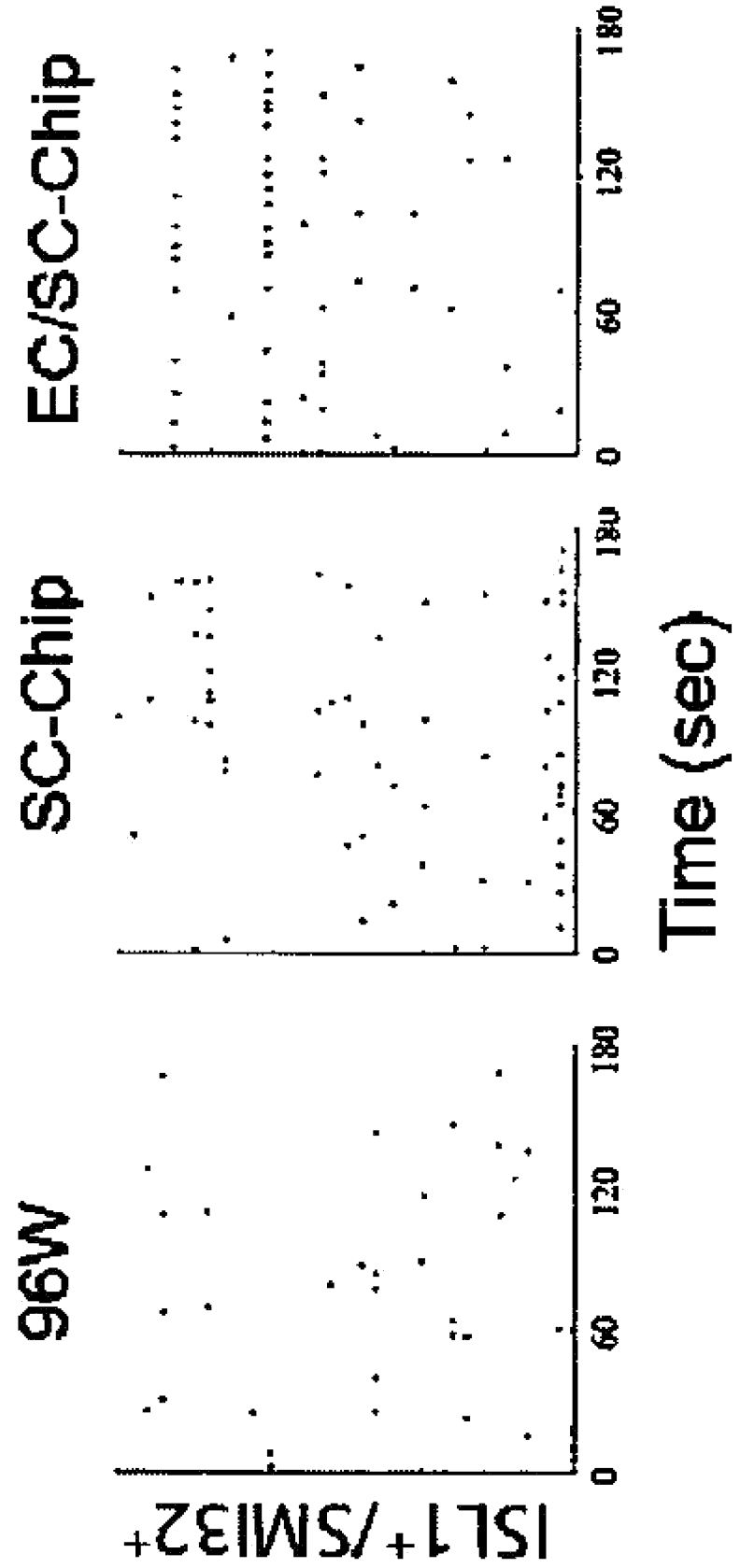
Figure 34H:
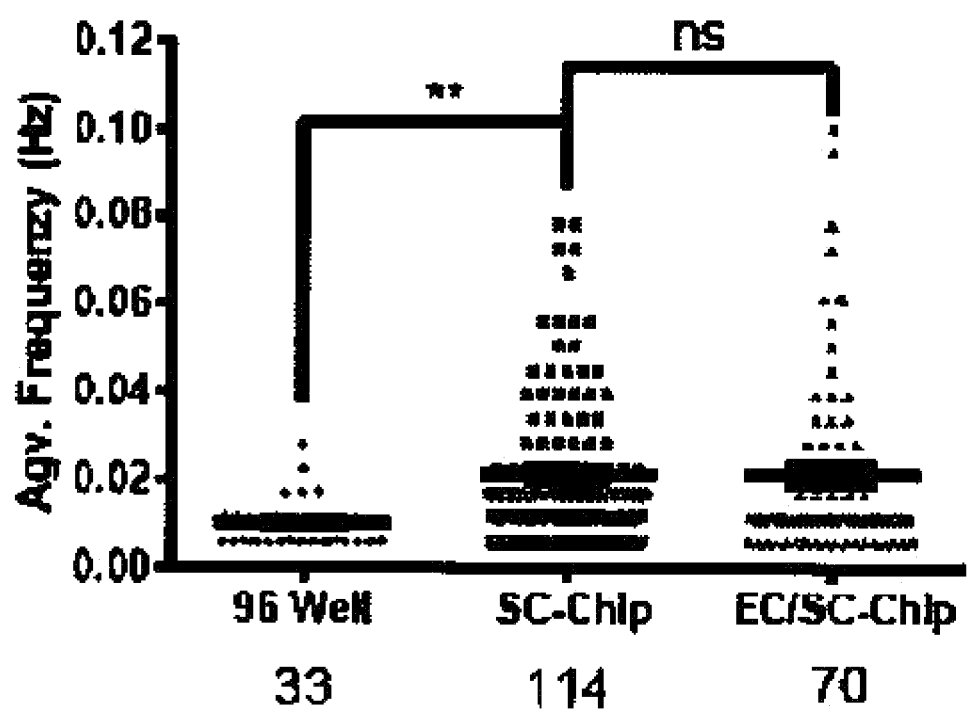

FIG. 34A-H Exemplary SC-Chip environment increases spontaneous neural activity. FIG. 34a Individual Representative calcium transient activity of SNP (top) and BMEC (bottom) cultures acquired at the seeding compartments plotted by change in florescence intensity over background (dF/F) with respect to time totaling 180 seconds. FIG. 34b Calcium transient activity plots of 30 representative neurons from each culture condition. Transient frequency of 194-297 neurons spanning three separate replicates per condition calculated in two individual lines FIG. 34c 83GFP and FIG. 34d 00iCTR. Neuron activity completely ablated with the administration of tetrodotoxin (TTX). FIG. 34e Immunocytochemistry staining of islet1 (ISL1) and smi32 (right) of site previously acquired for live calcium transients using fluro-4 dye (left). ISL1+ neurons (arrows) superimposed to determine MN firing specificity. FIG. 34f Mean transient frequency of representative active neurons compared to ISL1 overlaid MNs. Charts showing representative transient events from FIG. 34g ISL1 SMI32 double-positive neurons quantified and displayed as raster plot and plotted in FIG. 34h as frequency in hertz (Hz). Means represented by black bars and error bars represent standard error of the mean. Significance calculated by ANOVA,  denotes P<0.01, *=P<0.005, and ****=P<0.001.

Figure 35A:
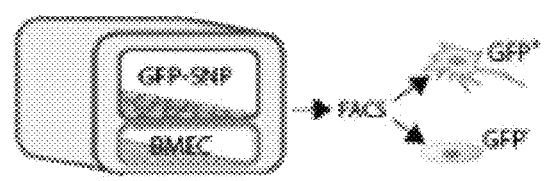
Figure 35B:
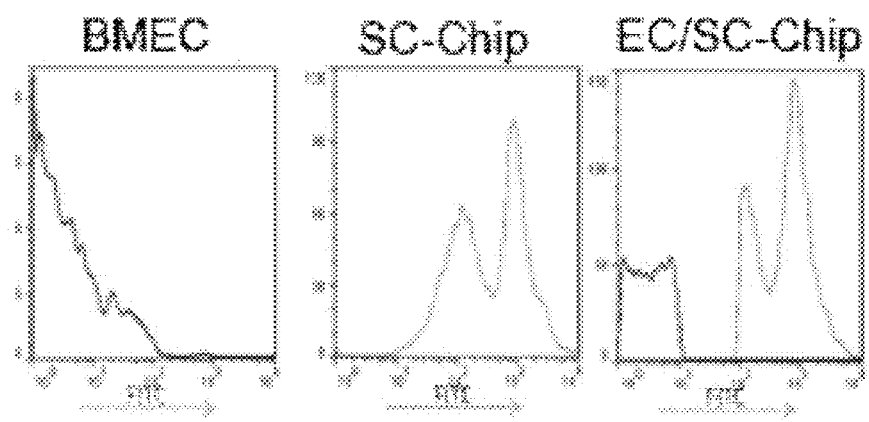
Figure 35C:
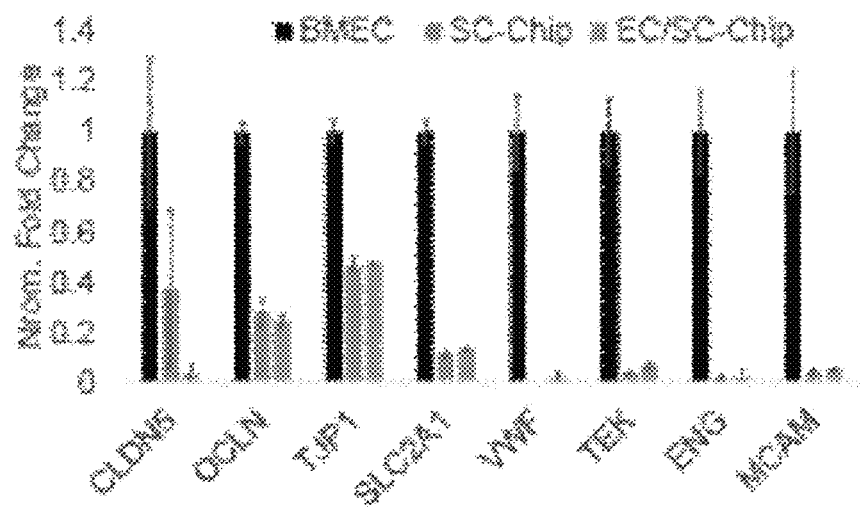
Figure 35D:
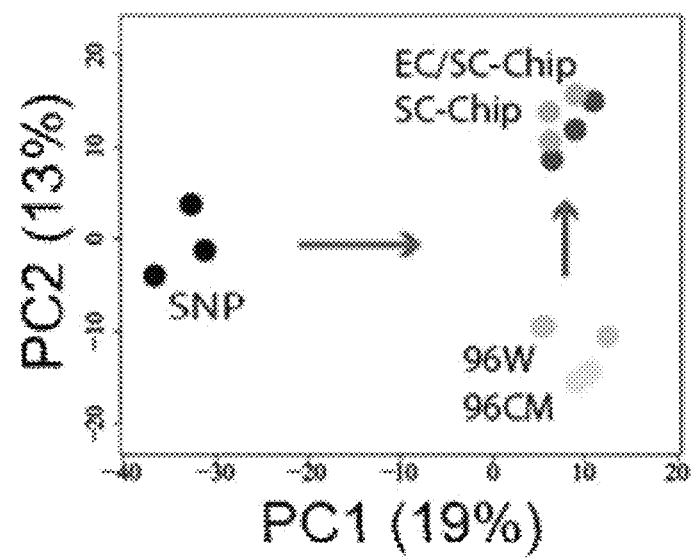
Figure 35D:
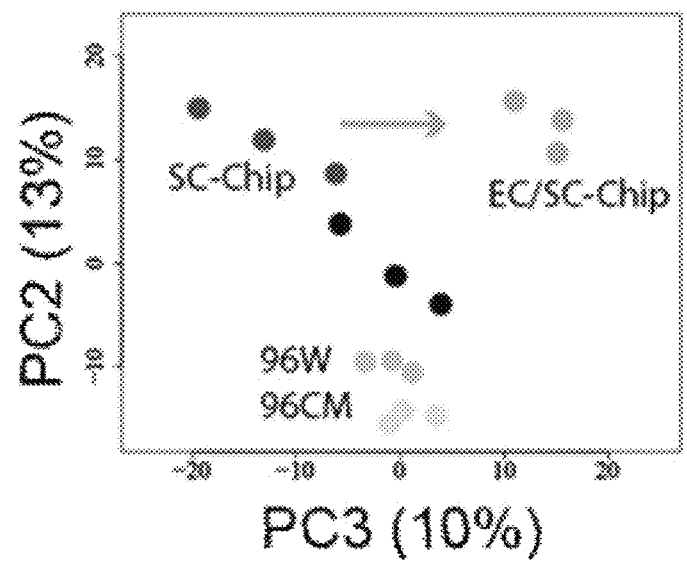
Figure 35E:
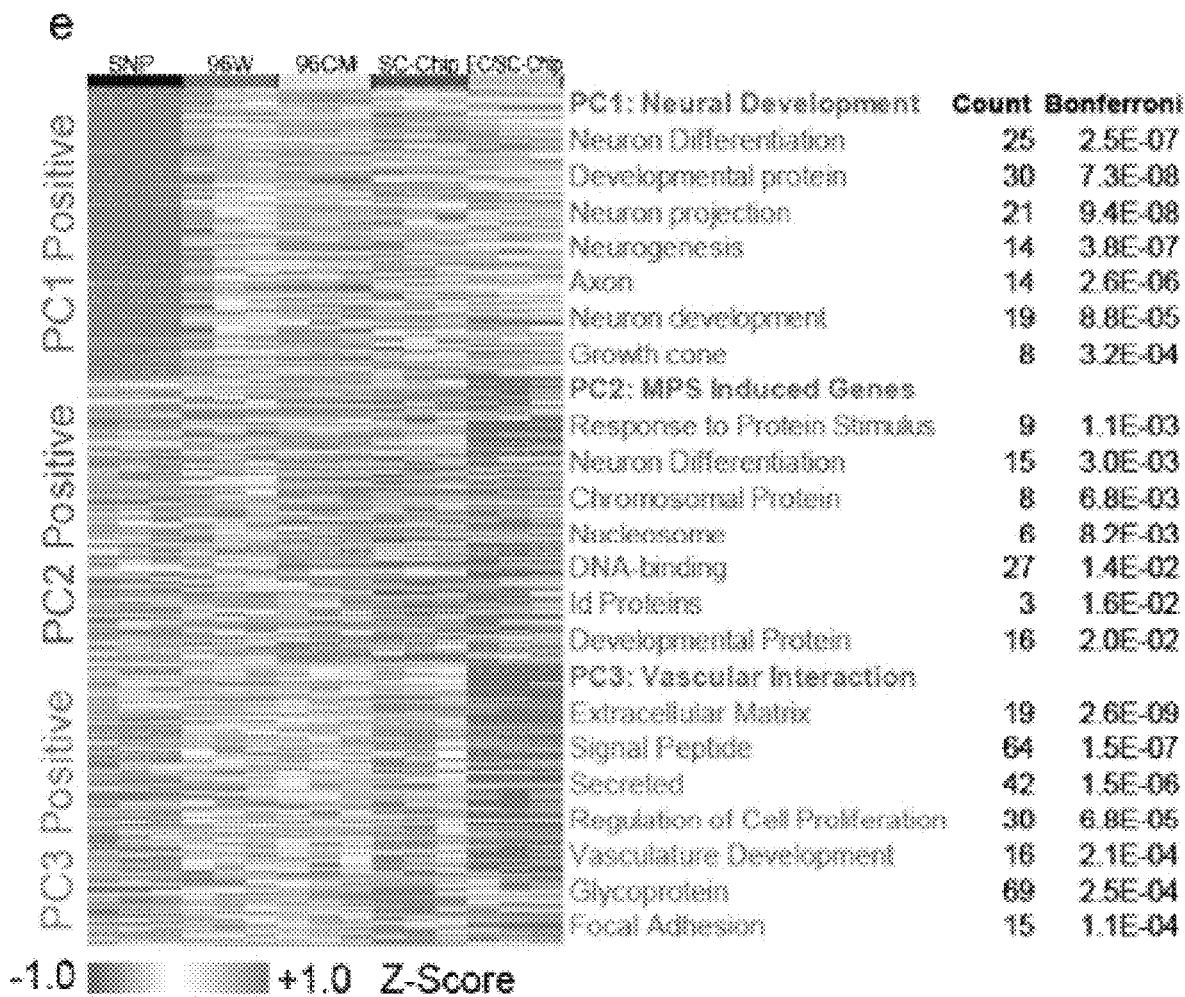

FIG. 35A-I Exemplary SC-Chip induces neural differentiation and vascular interaction gene expression. FIG. 35a GFP-MN isolation schematic: nuclear GFP expressing SNPs seeded on top channel with isogenic non-GFP expressing BMECs on bottom. Fluorescence-assisted cell sorting (FACS) conducted on FITC to purify spMNs after BMEC co-culture. FIG. 35b Single population histogram of chips seeded only with non-GFP BMECs (black) or GFP-MNs (green) that defined negative and positive fractions respectively. Number of events displayed on y-axis and FITC intensity on x-axis FIG. 35c Mean RPKM data of purified SC-Chip and EC/SC-Chip cultures normalized to RPKM data from iPSC derived BMECs cultured alone. Canonical markers claudin 5 (CLDN5), occluding (OCLN), Tight junction protein 1 (TJPI), Glut-1 (SLC2A1), von willebrand factor (VWF), Tie2 receptor (TEK), endoglin (ENG), and melanoma cell adhesion molecule (MCAM). FIG. 35d Principle component analysis plots of first two principle components (PC) (top) and PCs 2, and 3 (bottom). Arrows indicate weighting along the axis of each respective PC. FIG. 35e Top 200 ranked genes from each PC displayed as Z-score calculated across all conditions for each row and indicated by colorimetric scale. Each PC was entered into DAVID ontology pathway analysis and top 7 categories listed for each PC. The number of genes (count) in each category is displayed with corrected significance values from DAVID analysis (Bonferonni). FIG. 35f FIG. 35g Differentially expressed genes contributing to the "Response to Protein Stimulus" and "Neural Differentiation" DAVID terms enriched in PC2. RPKM data averaged across sample replicates and normalized to 96W control. (FIG. 35h, FIG. 35i) Differentially expressed genes contributing to "Vascular Development" and "Extracellular Matrix" DAVID terms enriched in PC3.

Figure 36A:
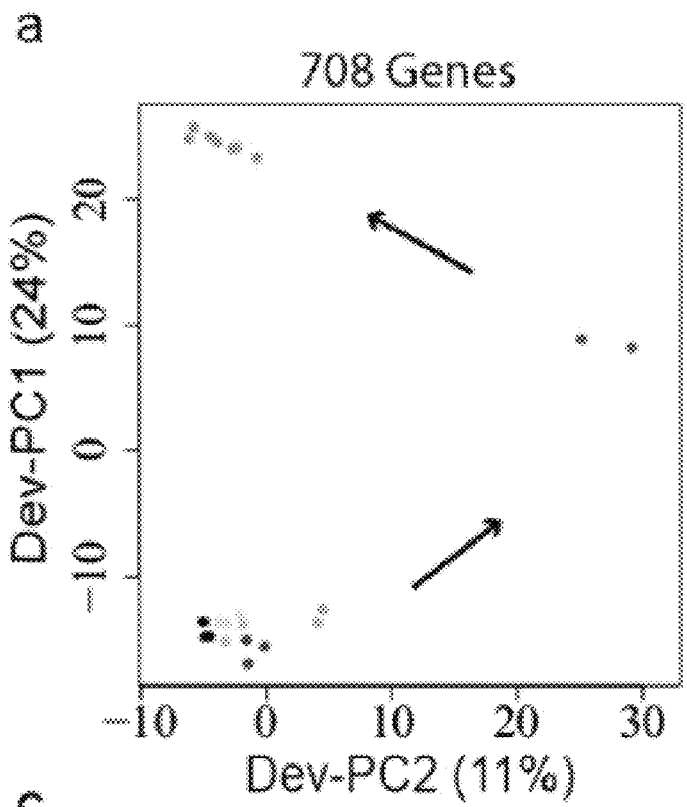
FIG. 36A-E Exemplary BMECs Induce Vascular Interaction Gene Expression In Chip.
Figure 36C:
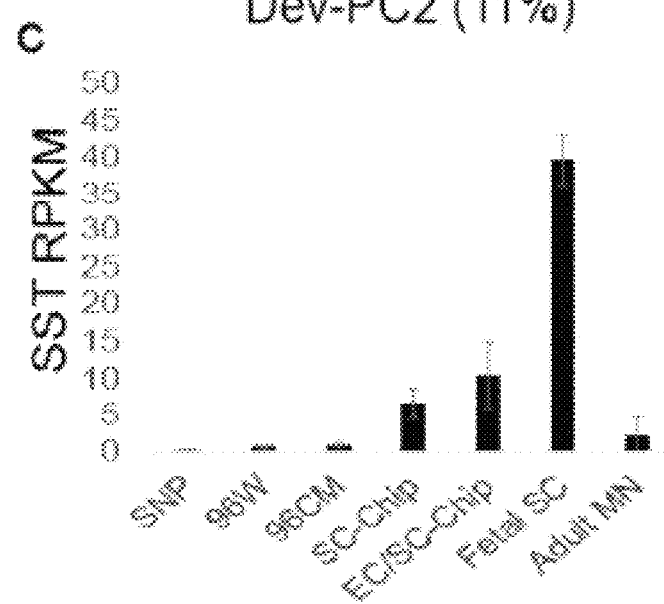
Figure 36B:
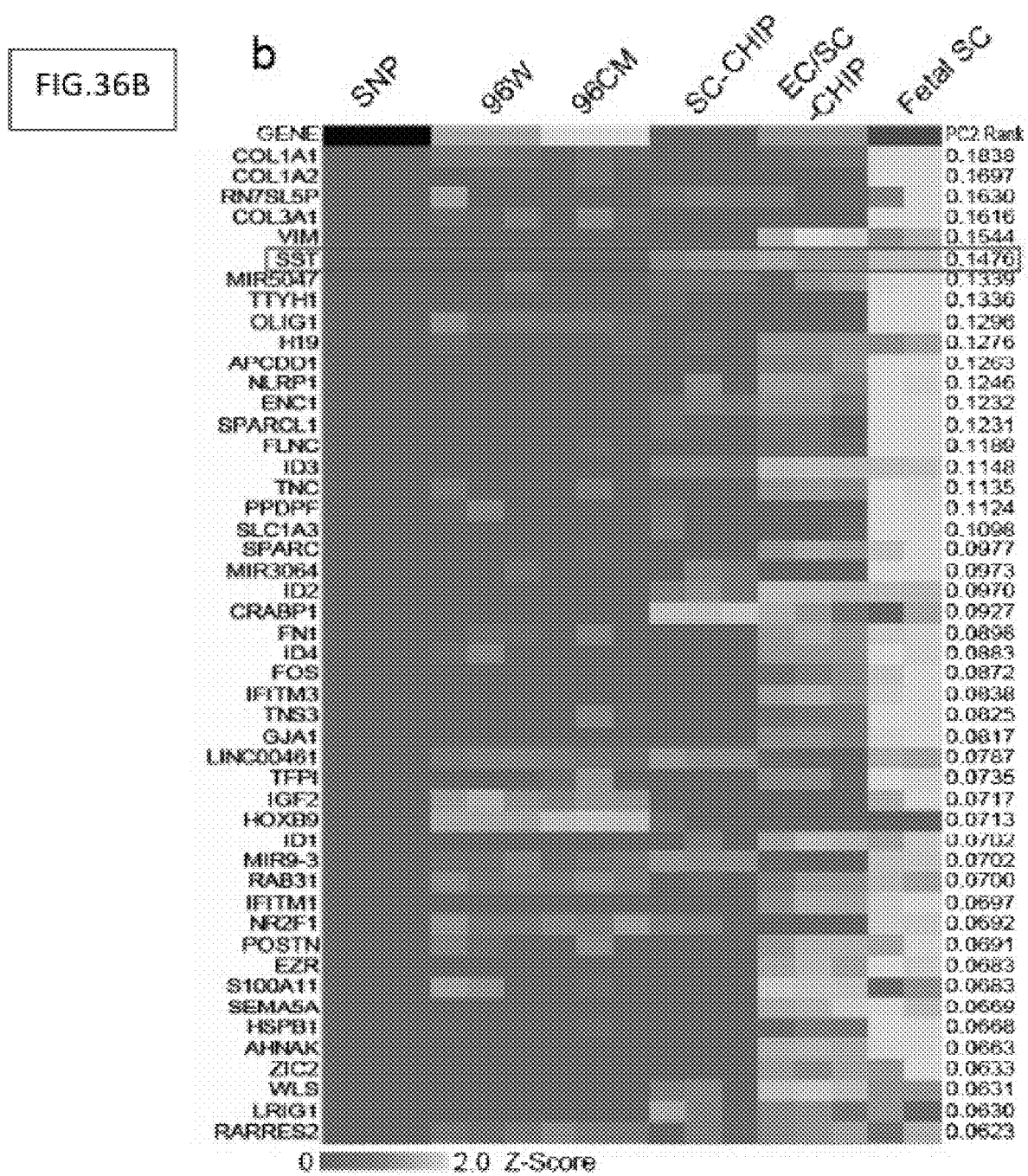
Figures 36D, 36E:
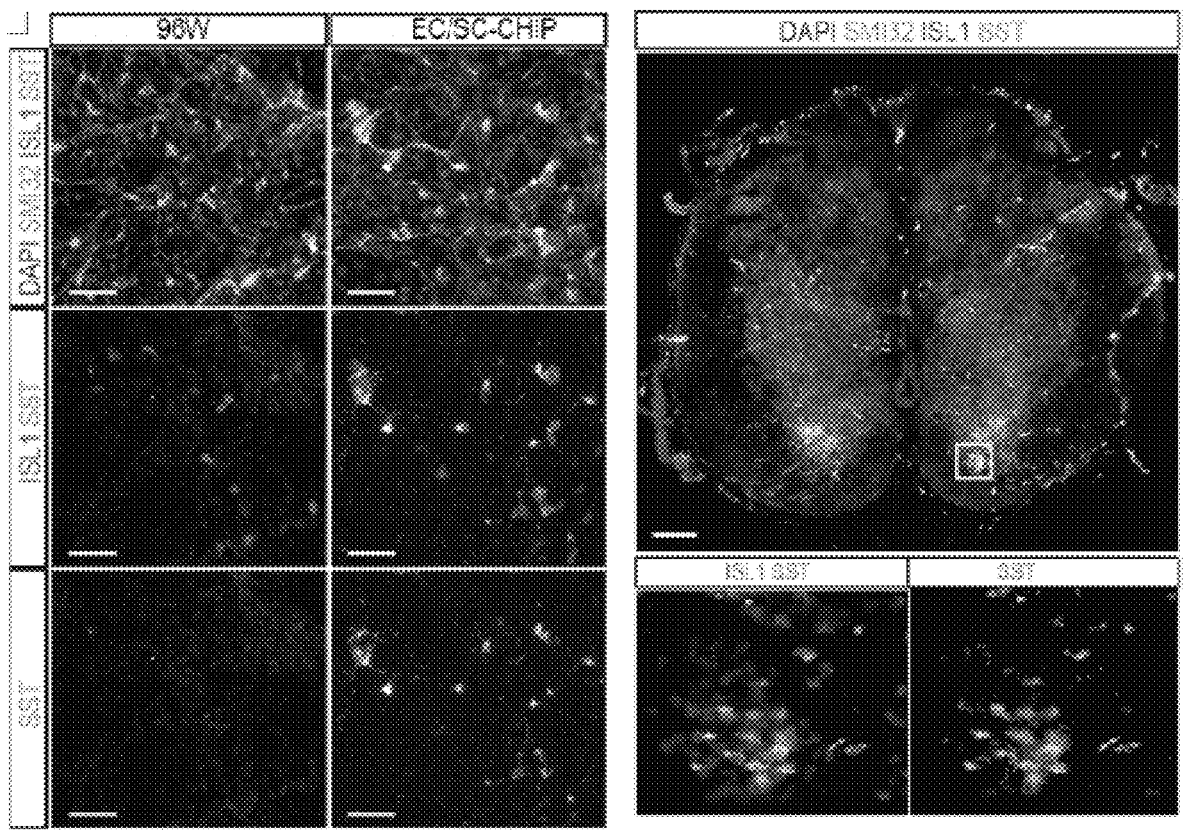

FIG. 36A-E Exemplary BMECs Induce Vascular Interaction Gene Expression In Chip. FIG. 36a PCA comparing expression data of differentially expressed genes from PC2 and PC3 and including in vivo adult laser captured MNs (green), in vivo fetal spinal cord (purple), and in vitro experimental data. FIG. 36b Heatmap of top ranking genes from Dev-PC2 that describe variance in fetal gene expression. Z-score calculated from Lop RPKM data per gene row and displayed by colorimetric scale. FIG. 36c Mean Somatostatin (SST) expression plotted for each condition, error bars represent standard deviation. FIG. 36d Representative images of 96 well (96W) and SC-Chips co-cultured with BMECs (EC/SC-Chip) immunostained with SST and MN markers SMI32 and ISL1, scale bars=40 microns. FIG. 36e Whole mount image of day 67 human fetal spinal cord (top) immunostained with SST, SMI32 and ISL1. Higher magnification of ventral horn ISL1 positive MN pool (box) co-expressing SST (bottom).

Figure 37B:
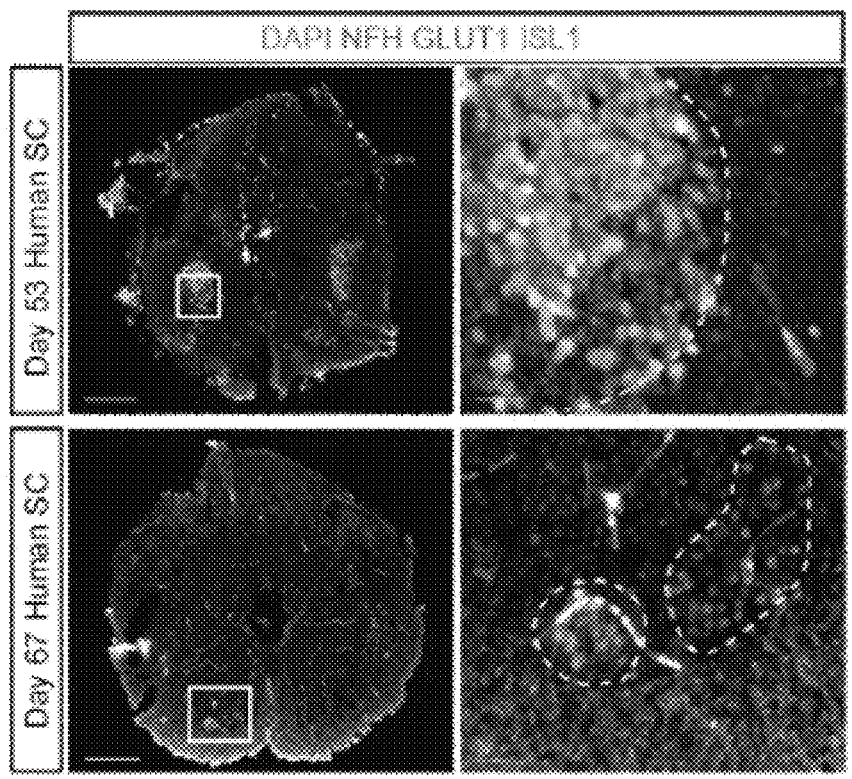
Figure 37C:
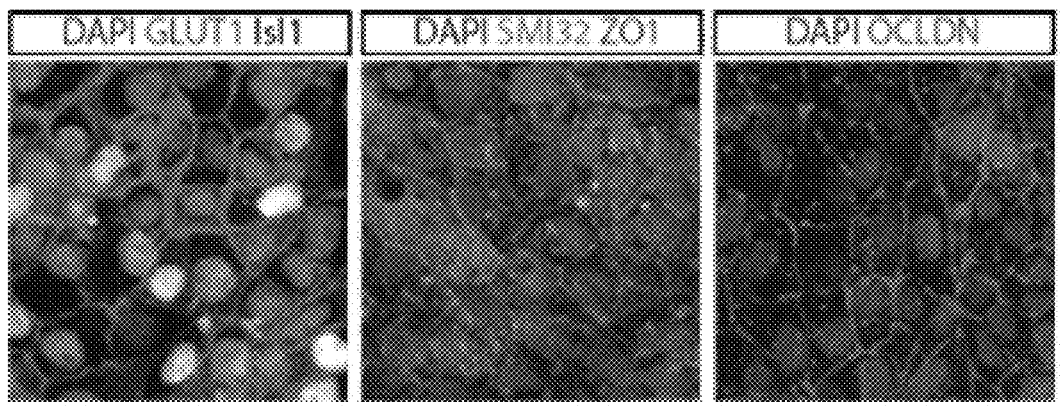
Figure 37D:
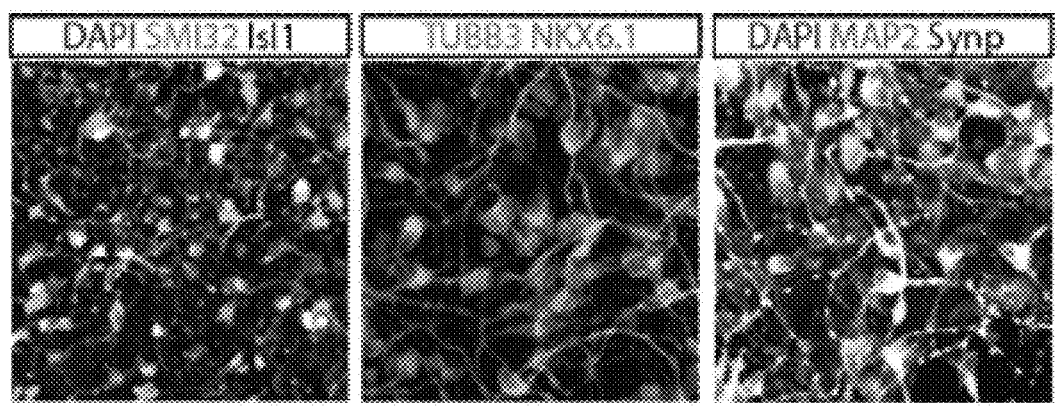

FIG. 37A-D Shows an illustrative comparison of fetal developmental stages (week 2 through birth) to differentiation of specialized cell types, including Motor Neurons, Endothelial Cells, Skeletal Muscle Cells and Astrocytes and examples of cell staining. FIG. 37a Schematic of relative emergence of cell types that directly interact with developing human MNs in vivo. FIG. 37b Days 53 and 67 human fetal spinal cords immunostained with neuronal marker neuofilament heavy chain (NFH), BMEC marker glucose transporter 1 (GLUT 1), and transcription factor ISL1. High magnification of ventral horns (box) show ISL1 positive MN pools (yellow dotted line). FIG. 37c Images of iPSC-derived BMECs cultured in 96-well plate for 6 days and immunostained with GLUT1, ISL1, and tight junction markers zona occludens 1 (ZO-1) and Occludin (OCLDN). FIG. 37d Images of SNPs cultured in 96W plate and immunostained with markers of spMNs SMI32, nuclear marker islet1 (ISL1), Beta 3 tubulin (TUBB3), NIOC6.1, neurofilament marker microtubule-associated protein 2 (MAP2), and synaptic marker synaptophysin (SYNP).

Figure 38A:
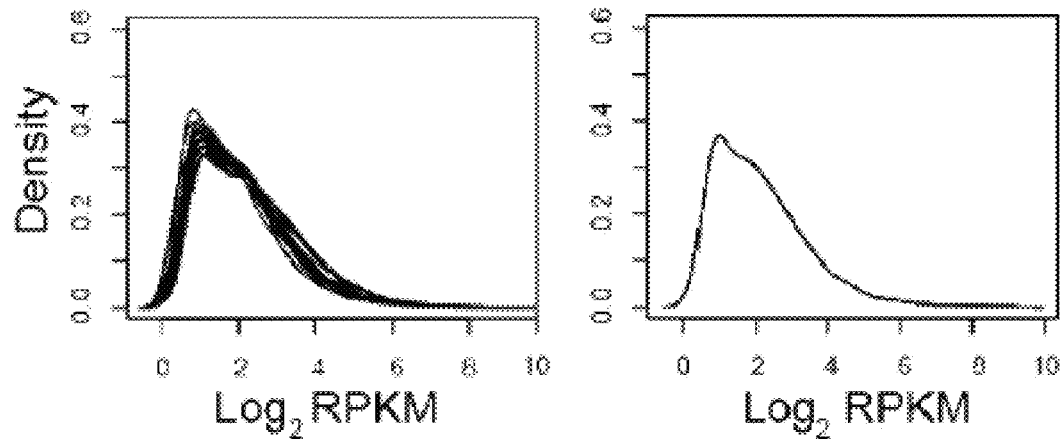
Figure 38B:
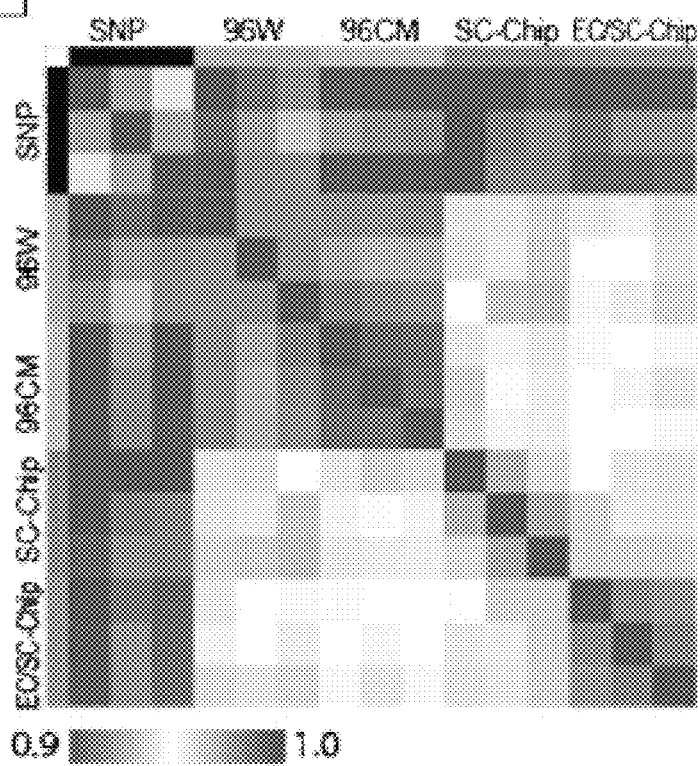

FIG. 38A-C An Exemplary Comparison Of Gene Expression Showing Density Plots And Comparison Of Datasets. FIG. 38a Density plots of 10,001 genes for each sample for transcriptomic analysis. Quantile normalized data (right). FIG. 38b Pierson correlation coefficient analysis of normalized RPKM datasets displayed by colorimetric scale. FIG. 38c Notch pathway genes differentially expressed in the SC-Chip conditions.

Figure 39B:
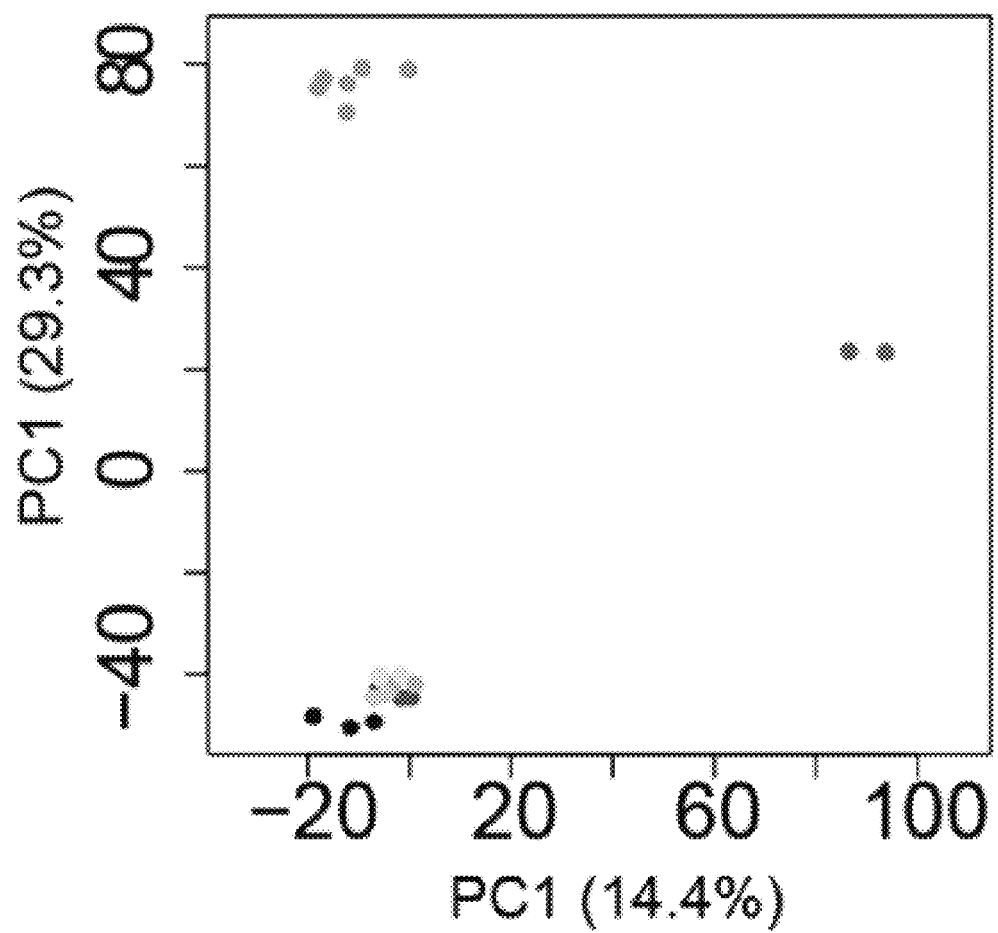

FIG. 39A-B An Exemplary Comparison Of Gene Expression Between Density And Principle Component Analysis (PCA). FIG. 39a Density plots of 10,001 genes of developmental comparison containing adult laser captured MNs (green: peaks on the left), fetal Spinal cord (purple: peaks on the right) and sorted iPSC-derived neurons (black: middle peaks); upper graph. Quantile normalized data (bottom). FIG. 39b PCA analysis of variance across all samples and all 10,001 genes. Adult laser captured MNs (green: upper left dots), fetal Spinal cord (purple: cluster of dots on the left) and sorted iPSC-derived neurons (black: lower left dots). Quantile normalized data (bottom).

DESCRIPTION OF PREFERRED EMBODIMENTS

In one embodiment, the present invention contemplates a BBB-on-chip where at least one population of cells is derived from a patient diagnosed with a disorder of the nervous system. While it is not intended that the present invention be limited to a particular CNS disorder, in one embodiment, the disorder is ALS. Amyotrophic lateral sclerosis (ALS) is a severe neurodegenerative condition characterized by loss of motor neurons in the brain and spinal cord. In one embodiment, the present invention contemplates generating induced pluripotent stem cells (iPSCs) from patients with ALS and differentiating them into motor neurons progenitors for seeding on a microfluidic device. There are currently no effective treatments for ALS. In one embodiment, the present invention contemplates the BBB-on-chip as a model system for testing drugs so as to predict success in subsequent clinical trials.

In another embodiment, the CNS disorder is Parkinson's disease (PD). PD is a neurodegenerative disorder primarily characterized by a loss of dopamine neurons, but which also leads to many other pathological changes.

In yet another embodiment, the CNS disorder is Alzheimer's disease. Alzheimer's is a type of dementia that causes problems with memory, thinking and behavior. Symptoms usually develop slowly and get worse over time, becoming severe enough to interfere with daily tasks.

It is contemplated that iPSC technology can be used together with microfluidic chips to mimic patient-specific phenotypes in disease states. For example, in another embodiment, cells derived from patients diagnosed with MCT8-specific thyroid hormone cell-membrane transporter deficiency are contemplated for use in microfluidic devices as at least one of the cellular components of the "BBB-on-chip." This disease is characterized by severe cognitive deficiency, infantile hypotonia, diminished muscle mass and generalized muscle weakness, progressive spastic quadriplegia, joint contractures, and dystonic and/or athetoid movement with characteristic paroxysms or kinesigenic dyskinesias. Seizures occur in about 25% of cases. Patients exhibit pathognomonic thyroid test results including high serum 3,3',5-triiodothyronine ($T_3$) concentration and low serum 3,3',5'-triiodothyronine (reverse $T_3$ or $rT_3$) concentration. Serum tetraiodothyronine (thyroxine or $T_4$) concentration is often reduced, but may be within the low normal range; serum TSH concentrations are normal or slightly elevated. SLC16A2 (also known as MCT8) is the only gene in which mutations are known to cause this disorder.

TABLE 1

Exemplary Experimental Conditions Tested.

| Condition | Apical Coating | Apical Cell Type | Density Apical | Apical Evaluation | Basal Coating | Cells Basal | Basal Density | Basal Evalutaion | Chip Number |
|---|---|---|---|---|---|---|---|---|---|
| 1. | Laminin (50 ug/mL) | DRY | none | Poor | COL/Fibro 2x | BMEC | ?? | Poor | 150 |
| 2. | Laminin (50 ug/mL) | EZ03 | 6.00E+06 | Success (High Density) | COL/Fibro 1x | BMEC 03iCTR | 2.0E+06 | Poor | 151 |
| 3. | Laminin (50 ug/mL) | iMNP25i | 2.50E+06 | Success (Med Density) | COL/Fibro 1x | BMEC 58iCTR | 2.0E+06 | Poor | 152 |
| 4. | Laminin (50 ug/mL) | iNPC | 1.50E+06 | Poor | COL/Fibro 1x | BMEC 03CTR | 2.0E+06 | Poor | 087 |
| 5. | Laminin (50 ug/mL) | iNPC | 1.50E+06 | Need eval . . . | COL/Fibro 1x | BMEC 03iCTR | 2.0E+06 | Poor | 083 |
| 6. | Laminin (50 ug/mL) | iMNp25i | 1.25E+06 | Success (Sphere and endo) | COL/Fibro 1x | BMEC 03iCTR | 2.0E+06 | Poor | 086 |
| 7. | Laminin (50 ug/mL) | iMNp25iSphere | n/a | Success (Lowest density) | COL/Fibro 1x | BMEC 03iCTR | 1.0E+06 | Success | 166 |
| 8. | Laminin (50 ug/mL) | iMNp25i | 1.25E+06 | Success (Med Density) | COL/Fibro 1x | BMEC 83iCTR | 1.0E+06 | Poor | 164 |
| 9. | Laminin (50 ug/mL) | EZ03 | 3.00E+06 | Success (Med Density) | COL/Fibro 1x | BMEC 58iMCT8 | 1.0E+06 | Poor | 165 |
| 10. | Laminin (50 ug/mL) | iNPC | 3.00E+06 | Success (Lowest density) | COL/Fibro 1x | BMEC 58iMCT8 | 2.0E+06 | Poor | 116 |
| 11. | Laminin (50 ug/mL) | EZ03 | 1.50E+06 | Success (High density) | COL/Fibro 1x | BMEC 58iMCT8 | 2.0E+06 | Poor | 295 |
| 12. | Laminin (50 ug/mL) | iMNp25i | 5.00E+06 | Success (Lowest density) | COL/Fibro 1x | BMEC 03iCTR | 2.0E+06 | Poor | 296 |
| 13. | Laminin (50 ug/mL) | EZ03 | 1.20E+07 | Success (High density) | COL/Fibro 0.2x | BMEC 03iCTR | 1.2E+07 | Fair | 281 |
| 14. | Laminin (50 ug/mL) | iMNp25i | 6.00E+06 | Success (High density) | COL/Fibro 0.2x | BMEC 03iCTR | 6.0E+06 | Poor | 291 |

TABLE 2

Exemplary Conditions Tested.

| Conditions | Chip ID | Top Cells | Density (mil/mL) | Top Coating | Top Concentration (ug/mL) | Bottom Cells | Cell Density | Coating Basal | Conc (ug/mL) | Apical Functionalization | Basal Functionalization | Flow Rate | Chips |
|---|---|---|---|---|---|---|---|---|---|---|---|---|---|
| 1 | 573 | 03CTR iBMEC | 14E6 | Col IV/Fibronectin (Fb) 1:4 (wet) | 320/80 | N/A | N/A | Col IV/Fibronectin (Fb) 1:4 (wet) | 320/80 | 100 W, 30 s, 15 sccm O2 | 100 W, 30 s, 15 sccm O2 | None | 1 |
| 2 | 574 | 03CTR iBMEC | 14E6 | Col IV/Fibronectin (Fb) 1:4 (dry) | 160/40 | N/A | N/A | Col IV/Fibronectin (Fb) 1:4 (dry) | 160/40 | 100 W, 30 s, 15 sccm O2 | 100 W, 30 s, 15 sccm O2 | None | 1 |
| 3 | 663 | iMNP | 14E6 | Laminin 1x | 50 | N/A | N/A | Laminin 1x | 50 | 100 W, 30 s, 15 sccm O2 | 100 W, 30 s, 15 sccm O2 | None | 1 |
| 4 | 664 | iMNP | TBD | Laminin 1x | 50 | iMNP | 14E6 | Col IV/Fibronectin (Fb) 1:4 (wet) | 320/80 | 100 W, 30 s, 15 sccm O2 | 100 W, 30 s, 15 sccm O2 | None | 1 |
| 5 | 665 | iMNP | TBD | Laminin 1x | 50 | 03CTR iBMEC | 14E6 | Col IV/Fibronectin (Fb) 1:4 (dry) | 160/40 | 100 W, 30 s, 15 sccm O2 | 100 W, 30 s, 15 sccm O2 | None | 1 |
| 6 | 667 | — | — | Col IV/Fibronectin (Fb) 1:4 (wet) | 320/80 | 03CTR iBMEC | 14E6 | Col IV/Fibronectin (Fb) 1:4 (wet) | 320/80 | 100 W, 30 s, 15 sccm O2 | Corona; 100 W, 30 s, 15 sccm O2 | None | 1 |
| 7 | 668 | — | — | Col IV/Fibronectin (Fb) 1:4 (dry) | 160/40 | 03CTR iBMEC | 14E6 | Col IV/Fibronectin (Fb) 1:4 (dry) | 160/40 | 100 W, 30 s, 15 sccm O2 | Corona; 100 W, 30 s, 15 sccm O2 | None | 1 |
| 8 | 693 | Neuron? | TBD | Laminin | 50 | 03CTR iBMEC | 14E6 | Col IV/Fibronectin (Fb) 1:4 (wet) | 320/80 | 100 W, 30 s, 15 sccm O2 | Corona; 100 W, 30 s, 15 sccm O2 | None | 1 |

TABLE 3

Exemplary Conditions Tested.

| Conditions | Chip ID | Top Cells | Density (mil/mL) | Top Coating | Top Concentration (ug/mL) | Bottom Cells | Cell Density | Coating Basal | Conc (ug/mL) | Apical Functionalization | Basal Functionalization | Flow Rate | C |
|---|---|---|---|---|---|---|---|---|---|---|---|---|---|
| 1 | 761 | 03CTR iBMEC | 14E6 | Col IV/Fibronectin (Fb) 1:4 (wet) | 320/80 | N/A | N/A | Col IV/Fibronectin (Fb) 1:4 (wet) | 320/80 | 100 W, 30 s, 15 sccm O2 | 100 W, 30 s, 15 sccm O2 | None | |
| 2 | 762 | 03CTR iBMEC | 14E6 | Col IV/Fibronectin (Fb) 1:4 (dry) | 160/40 | N/A | N/A | Col IV/Fibronectin (Fb) 1:4 (dry) | 160/40 | 100 W, 30 s, 15 sccm O2 | 100 W, 30 s, 15 sccm O2 | None | |
| 3 | 763 | 03CTR iBMEC | 14E6 | Laminin 1x | 50 | N/A | N/A | Laminin 1x | 50 | 100 W, 30 s, 15 sccm O2 | 100 W, 30 s, 15 sccm O2 | None | |
| 4 | 764 | Neuron? | TBD | Laminin 1x | 50 | 03CTR iBMEC | 14E6 | Col IV/Fibronectin (Fb) 1:4 (wet) | 320/80 | 100 W, 30 s, 15 sccm O2 | 100 W, 30 s, 15 sccm O2 | None | |
| 5 | 765 | — | — | Col IV/Fibronectin (Fb) 1:4 (wet) | 320/80 | 03CTR iBMEC | 14E6 | Col IV/Fibronectin (Fb) 1:4 (wet) | 320/80 | 100 W, 30 s, 15 sccm O2 | Corona; 100 W, 30 s, 15 sccm O2 | None | |
| 6 | 766 | — | — | Col IV/Fibronectin (Fb) 1:4 (dry) | 160/40 | 03CTR iBMEC | 14E6 | Col IV/Fibronectin (Fb) 1:4 (dry) | 160/40 | 100 W, 30 s, 15 sccm O2 | Corona; 100 W, 30 s, 15 sccm O2 | None | |

THE FOLLOWING REFERENCES ARE HEREIN INCORPORATED BY REFERENCE IN THEIR ENTIRETY

Avior, Y., I. Sagi and N. Benvenisty (2016). "Pluripotent stem cells in disease modelling and drug discovery." Nat Rev Mol Cell Biol 17(3): 170-182.

Bhatia, S. N. and D. E. Ingber (2014). "Microfluidic organs-on-chips." Nat Biotech 32(8): 760-772.

Borghese, L., D. Dolezalova, T. Opitz, S. Haupt, A. Leinhaas, B. Steinfarz, P. Koch, F. Edenhofer, A. Hampl and O. Briistle (2010). "Inhibition of Notch Signaling in Human Embryonic Stem Cell—Derived Neural Stem Cells Delays Gl/S Phase Transition and Accelerates Neuronal Differentiation In Vitro and In Vivo." STEM CELLS 28(5): 955-964.

Christopherson, K. S., E. M. Ullian, C. C. Stokes, C. E. Mullowney, J. W. Hell, A. Agah, J. Lawler, D. F. Mosher, P. Bornstein and B. A. Barres (2005). "Thrombospondins are astrocyte-secreted proteins that promote CNS synaptogenesis." Cell 120(3): 421-433.

Daneman, R., L. Zhou, A. A. Kebede and B. A. Barres (2010). "Pericytes are required for blood-brain barrier integrity during embryogenesis." Nature 468(7323): 562-566.

Demestre, M., M. Orth, K. J. Fohr, K. Achberger, A. C. Ludolph, S. Liebau and T. M. Boeckers (2015). "Formation and characterisation of neuromuscular junctions between hiPSC derived motoneurons and myotubes." Stem Cell Res 15(2): 328-336.

Domenech, M., H. Yu, J. Warrick, N. M. Badders, I. Meyvantsson, C. M. Alexander and D. J. Beebe (2009). "Cellular observations enabled by microculture: paracrine signaling and population demographics." Integrative biology: quantitative biosciences from nano to macro 1(3): 267-274.

Du, Z. W., H. Chen, H. Liu, J. Lu, K. Qian, C. L. Huang, X. Zhong, F. Fan and S. C. Zhang (2015). "Generation and expansion of highly pure motor neuron progenitors from human pluripotent stem cells." Nat Commun 6: 6626.

Engelhardt, B. and S. Liebner (2014). "Novel insights into the development and maintenance of the blood—brain barrier." Cell and Tissue Research 355(3): 687-699.

Ericson, J., P. Rashbass, A. Schedl, S. Brenner-Morton, A. Kawakami, V. van Heyningen, T. M. Jessell and J. Briscoe (1997). "Pax6 controls progenitor cell identity and neuronal fate in response to graded Shh signaling." Cell 90(1): 169-180.

Ferriero, D. M., R. A. Sheldon and R. O. Messing (1994). "Somatostatin enhances nerve growth factor-induced neurite outgrowth in PC12 cells." Brain Res Dev Brain Res 80(1-2): 13-18.

Gu, C. and E. Giraudo (2013). "The role of semaphorins and their receptors in vascular development and cancer." Experimental Cell Research 319(9): 1306-1316.

Guo, J.-H., W. Ma, J.-W. Yang, Y. Gao, Z. Liang, J. Liu, D.-Y. Wang, T. Luo, J.-R. Cheng and L.-Y. Li (2015). "Expression pattern of NeuN and GFAP during human fetal spinal cord development." Child's Nervous System 31(6): 863-872.

Hesselmans, L. F., F. G. Jennekens, C. J. Van den Oord, H. Veldman and A. Vincent (1993). "Development of innervation of skeletal muscle fibers in man: relation to acetylcholine receptors." Anat Rec 236(3): 553-562.

Ho, R., S. Sances, G. Gowing, M. W. Amoroso, J. G. O'Rourke, A. Sahabian, H. Wichterle, R. H. Baloh, D. Sareen and C. N. Svendsen (2016). "ALS disrupts spinal motor neuron maturation and aging pathways within gene co-expression networks." Nat Neurosci 19(9): 1256-1267.

Huang da, W., B. T. Sherman and R. A. Lempicki (2009). "Systematic and integrative analysis of large gene lists using DAVID bioinformatics resources." Nat Protoc 4(1): 44-57.

Kaupmann, K., C. Bruns, D. Hoyer, K. Seuwen and H. Lubbert (1993). "Distribution and second messenger coupling of four somatostatin receptor subtypes expressed in brain." FEBS Lett 331(1-2): 53-59.

Kurz, H. (2009). "Cell lineages and early patterns of embryonic CNS vascularization." Cell Adhesion & Migration 3(2): 205-210.

Lacar, B., S. B. Linker, B. N. Jaeger, S. Krishnaswami, J. Barron, M. Kelder, S. Parylak, A. Paquola, P. Venepally, M. Novotny, C. O'Connor, C. Fitzpatrick, J. Erwin, J. Y. Hsu, D. Husband, M. J. McConnell, R. Lasken and F. H. Gage (2016). "Nuclear RNA-seq of single neurons reveals molecular signatures of activation." Nat Commun 7: 11022.

Lee, N. V., M. Sato, D. S. Annis, J. A. Loo, L. Wu, D. F. Mosher and M. L. Iruela-Arispe (2006). "ADAMTS1 mediates the release of antiangiogenic polypeptides from TSP1 and 2." Embo j 25(22): 5270-5283.

Lippmann, E. S., A. Al-Ahmad, S. M. Azarin, S. P. Palecek and E. V. Shusta (2014). "A retinoic acid-enhanced, multicellular human blood-brain barrier model derived from stem cell sources." Sci Rep 4: 4160.

Lukaszewicz, A. I. and D. J. Anderson (2011). "Cyclin DI promotes neurogenesis in the developing spinal cord in a cell cycle-independent manner." Proceedings of the National Academy of Sciences 108(28): 11632-11637.

Maury, Y., J. Come, R. A. Piskorowski, N. Salah-Mohellibi, V. Chevaleyre, M. Peschanski, C. Martinat and S. Nedelec (2015). "Combinatorial analysis of developmental cues efficiently converts human pluripotent stem cells into multiple neuronal subtypes." Nat Biotech 33(1): 89-96.

Montoya, G. J., J. J. Sutachan, W. S. Chan, A. Sideris, T. J. Blanck and E. Recio-Pinto (2009). "Muscle-conditioned media and cAMP promote survival and neurite outgrowth of adult spinal cord motor neurons." Exp Neurol 220(2): 303-315.

Moody, W. J. and M. M. Bosma (2005). "Ion channel development, spontaneous activity, and activity-dependent development in nerve and muscle cells." Physiol Rev 85(3): 883-941.

O'Rourke, J. G., L. Bogdanik, A. Yanez, D. Lall, A. J. Wolf, A. K. Muhammad, R. Ho, S. Carmona, J. P. Vit, J. Zarrow, K. J. Kim, S. Bell, M. B. Harms, T. M. Miller, C. A. Dangler, D. M. Underhill, H. S. Goodridge, C. M. Lutz and R. H. Baloh (2016). "C9or f72 is required for proper macrophage and microglial function in mice." Science 351(6279): 1324-1329.

Palmer, T. D., A. R. Willhoite and F. H. Gage (2000). "Vascular niche for adult hippocampal neurogenesis." J Comp Neurol 425(4): 479-494.

Pasterkamp, R. J. (2012). "Getting neural circuits into shape with semaphorins." Nat Rev Neurosci 13(9): 605-618.

Patel, T. P., K. Man, B. L. Firestein and D. F. Meaney (2015). "Automated quantification of neuronal networks and single-cell calcium dynamics using calcium imaging." J Neurosci Methods 243: 26-38.

Persson, M., D. Stamataki, P. to Welscher, E. Andersson, J. Bose, U. Riither, J. Ericson and J. Briscoe (2002). "Dorsal-ventral patterning of the spinal cord requires Gli3 transcriptional repressor activity." Genes & Development 16(22): 2865-2878.

Pfaff, S. L., M. Mendelsohn, C. L. Stewart, T. Edlund and T. M. Jessell (1996). "Requirement for LIM Homeobox Gene Isl 1 in Motor Neuron Generation Reveals a Motor Neuron— Dependent Step in Interneuron Differentiation." Cell 84(2): 309-320.

Przybyla, L. and J. Voldman (2012). "Probing embryonic stem cell autocrine and paracrine signaling using microfluidics." Annual review of analytical chemistry (Palo Alto, Calif.) 5: 293-315.

Rezaie, P. and D. Male (1999). "Colonisation of the developing human brain and spinal cord by microglia: a review." Microsc Res Tech 45(6): 359-382.

Rushton, D. J., V. B. Mattis, C. N. Svendsen, N. D. Allen and P. J. Kemp (2013). "Stimulation of GABA-induced Ca2+ influx enhances maturation of human induced pluripotent stem cell-derived neurons." PLoS One 8(11): e81031.

Sasaki, M., S. Seo-Kiryu, R. Kato, S.-i. Kita and H. Kiyama (2001). "A disintegrin and metalloprotease with thrombospondin type 1 motifs (ADAMTS-1) and IL-1 receptor type 1 mRNAs are simultaneously induced in nerve injured motor neurons." Molecular Brain Research 89(1-2): 158-163.

Schweitzer, J., T. Becker, J. Lefebvre, M. Granato, M. Schachner and C. G. Becker (2005). "Tenascin-C is involved in motor axon outgrowth in the trunk of developing zebrafish." Dev Dyn 234(3): 550-566.

Shen, Q., S. K. Goderie, L. Jin, N. Karanth, Y. Sun, N. Abramova, P. Vincent, K. Pumiglia and S. Temple (2004). "Endothelial cells stimulate self-renewal and expand neurogenesis of neural stem cells." Science 304(5675): 1338-1340.

Shen, Q., S. K. Goderie, L. Jin, N. Karanth, Y. Sun, N. Abramova, P. Vincent, K. Pumiglia and S. Temple (2004). "Endothelial Cells Stimulate Self-Renewal and Expand Neurogenesis of Neural Stem Cells." Science 304(5675): 1338-1340.

Tuncdemir, S. N., B. Wamsley, F. J. Stam, F. Osakada, M. Goulding, E. M. Callaway, B. Rudy and G. Fishell (2016). "Early Somatostatin Interneuron Connectivity Mediates the Maturation of Deep Layer Cortical Circuits." Neuron 89(3): 521-535.

Varnum-Finney, B., K. Venstrom, U. Muller, R. Kypta, C. Backus, M. Chiquet and L. F. Reichardt (1995). "The Integrin Receptor $\alpha(8)\beta(1)$ Mediates Interactions of Embryonic Chick Motor and Sensory Neurons with Tenascin-C." Neuron 14(6): 1213-1222.

Walchli, T., A. Wacker, K. Frei, L. Regli, M. E. Schwab, S. P. Hoerstrup, H. Gerhardt and B. Engelhardt (2015). "Wiring the Vascular Network with Neural Cues: A CNS Perspective." Neuron 87(2): 271-296.

Warp, E., G. Agarwal, C. Wyart, D. Friedmann, C. S. Oldfield, A. Conner, F. Del Bene, A. B. Arrenberg, H. Baier and E. Y. Isacoff (2012). "Emergence of patterned activity in the developing zebrafish spinal cord." Curr Biol 22(2): 93-102.

Yu, H., C. M. Alexander and D. J. Beebe (2007). "Understanding microchannel culture: parameters involved in soluble factor signaling." Lab Chip 7(6): 726-730.

Zacchigna, S., D. Lambrechts and P. Carmeliet (2008). "Neurovascular signalling defects in neurodegeneration." Nat Rev Neurosci 9(3): 169-181.

EXPERIMENTAL

Immunohistochemistry

Fetal tissue was received from the Birth Defects Research Laboratory at the University of Washington under their approved Institutional review board (IRB), consent and privacy guidelines. Protocols were performed in accordance with the Institutional Review Board's guidelines at the Cedars-Sinai Medical Center under the auspice IRB-SCRO Protocol Pro00021505.

Spinal cord samples arrived with estimated age and as partially intact spinal columns which were partitioned into approximated cervical, thoracic and lumbar sections. Fetal tissue was subsequently fixed in 4% paraformaldehyde for 48 hr, and placed in 30% sucrose for an additional 24 hour. Finally, spinal cords were embedded in TISSUE-TEK® compound OCT (VWR) and sectioned at 25 μm an using a cryostat (Leica) at −20° C. and directly mounted on glass slides (Fisher Scientific). Tissue sections were permeabilized in cold MeOH for 20 minutes, and blocked in PBS containing 5% normal donkey serum (Sigma, D9663) and 0.25% TRITON™-X detergent solution for 1.5 hour, then transferred to primary antibody solution containing mouse anti-GLUT1 (R&D Systems, 1:100) SMI-32P-100 (Covance, 1:1,000), and goat anti-Islet-1 (R&D, AF1387, 1:500), and rabbit anti-NFH (Sigma, N4142, 1:1000), rabbit anti-SIRT (Sigma, SAB4502861, 1:100) and incubated overnight at 4° C. Samples were then incubated for 1 h at room temperature in donkey anti-mouse ALEXA FLUOR® dye 488 and donkey anti-goat 594 secondary antibodies (Life Technologies, A21202 and A21289, 1:1,000 each). Fetal samples were mounted in FLUOROMOUNT-G ml sealant (Southern Biotech, 0100-01) and acquired at 20× using automated stitching on a LEICA® DM 6000 microscope for whole mount image.

iPSC-derived cultures were fixed in 4% paraformaldehyde, and rinsed with PBS. Cultures were permeabilized in 10% TRITON™-X detergent solution at RT for 10 min and blocked in 5% donkey serum and 0.1% TRITON™-X detergent solution at RT for 1 h. Samples were incubated overnight at 4° C. in primary antibody solution containing the following antibodies: mouse anti-SMI-32 (Covance, SMI-32P-100, 1:1,000), rabbit anti-ZO-1 ( ) mouse anti-GLUT1 (GLUT1), mouse anti-Occiudin ( ) mouse anti-Claudin5 ( ) rinsed in PBS, and incubated for 1 h at room temperature in donkey anti-mouse ALEXA FLUOR® dye 488, donkey anti-goat 594, and donkey anti-goat 647 secondary antibodies (Life Technologies, A21202 and A21289, 1:1,000 each).

Imaging and Population

Confocal images were acquired using an A1 confocal microscope (Nikon) using a Plan Apo 10× objective at 1-micron increments. FIG. 33D was generated from autostitching three confocal stacks at 10× (Nikon Elements). Images were rendered with maximum projection and quantified using Imaris (Bitplane). For population and ISL1 nuclei size analysis, images were cropped to only top channel and max projected using IMARIS software. Sites were prioritized as containing maximal GFP positive nuclei in the frame. GFP positive nuclei were quantified using spots algorithm and ISL1 positive nuclei were quantified by filtering by GFP co-localization.

Transcriptomic Analysis

BMECs were seeded in endothelial cell media into either a T75 flask, or the bottom channel of the SC-chip. SNPs were thawed and seeded into either the 96 well plates or the top channel of the Chip and incubated overnight. The following day, media was replaced with Stage 3 media in all conditions. BMEC flask was washed 2× with minimal neural media (IMDM:F12 N2, 1% B27, 0.5× NEAA, 1× PSA). 24 hours later BMEC media was collected, centrifuged and filtered. BMEC conditioned media was then supplemented with remaining ingredients for Stage 3 media. Media for all conditions was replaced every two days. At 6 days postseeding, samples were dissociated with ACCUTASE® enzyme solution (Sigma-Aldrich). 3 Chip or 3 wells of a 96 well plate were pooled for each experimental replicate for a total of three replicates. Pooled samples were washed in PBS, resuspended in cold MACS buffer (Miltenyl Biotech), and filtered using a 40-micron screen. Cells were sorted using an Influx™ FACS sorter (BD). GFP positive gating was established using SC-chip seeded exclusively with 83iGFP MNs for a positive control, and 83iCTR BMECs for a negative control. Samples were sorted using this established gating. Positive fraction cell pellets were frozen at −80° C. until processing. For population counts at day 30, both channels were dissociated as before, and one Chip per replicate was quantified by number of GFP positive events.

Live Calcium Transient Imaging and Analysis

Fluo-4 calcium dye (Invitrogen), was prepared at 10 mM in 50% PLURONIC™ solution and DMSO, and diluted to a final concentration of 20 μM in ECS. Tissue cultures were incubated at RT for 30 minutes, then washed in fresh ECS and incubated an additional 30 minutes before acquiring. After a 2-minute burn in phase, 16 bit videos were acquired for 3 minutes at 20 Hz on an Eclipse Ti microscope (Nikon) using a Plan Flor 20× objective (Nikon) equipped with an Orca—Flash4.0 LT digital camera (Hamamatsu). As no difference in event detection was determined between 16—and 8-bit data, all datasets were down-sampled to 8-bit (ImageJ). Calcium activity was counted by tracing ROI in blinded fashion, i.e. the treatment conditions were not associated with the results, and creating masks for use in extracting intensity data (ImageJ). 20-50 neurons were counted per site, and at least 3 Chip or wells were included for each condition. A total of 148-400 neurons per condition were analyzed using MATLAB® software. dF/F traces were extracted through FluoroSNNAP (Patel, Man et al. 2015). Automated calcium event detection was accomplished through template libraries described previously at a threshold of 0.05. Events were then curated manually by a blinded counter, in other words a person evaluated the events without knowing the associated treatment conditions.

Example 1

Human induced pluripotent stem cells were derived and maintained. Cells are prepared either directly from cultured iPSCs or from frozen lots of pre-differentiated cells.

In the case of MNs, for example, cells are seeded at day 12 of differentiation either from freshly differentiated cultures or directly from a thawed vial. iPSC-derived forebrain neural progenitor cultures (dubbed EZs) were cultured in chip either dissociated or as neural spheres that attached and extended in 3 dimensions (See FIG. 3 apical). The various factors used in the protocol (see above chart and tabs) for the generation of motor neurons are provided (using iPSCs as the starting material).

A. Spinal Motor Neuron Progenitors (SNP).

More specifically, spinal motor neuron derivation was accomplished using a modification of a previously published protocol (i.e. Du, Chen et al. 2015). Briefly, iPSCs were mechanically passaged and maintained at low density. IPSCs were harvested then seeded into chips. Differentiation was induced for 6 days in neural induction media (days 0-6) consisting of IMDM/F12 (Gibco), B27, N2, 1% NEAA, 0.2 uM LDN193189, 10 uM SB431542, 3 uM CHIR99021 (Cayman Chemical); and Penicillin Streptomycin-Amphotericin B (PSA).

Cells were then passaged using ACCUTASE® enzyme solution (Sigma-Aldrich) and reseeded onto MATRIGEL® substrate and patterned in Stage 2 media (days 6-12) consisting of IMDM/F12 (Gibco), B27, N2, 1% NEAA, 200 ng/ml ascorbic acid, 0.1 uM retinoic acid, 1 uM SAG and Penicillin-Streptomycin-Amphotericin B (PSA) for an additional 6 days. Cells were then dissociated and cryogenically frozen for later use. At day 12 of culture cells are labeled ventral spinal neuron progenitors (SNP) when cultured using the method described in this and the above paragraph.

At day 12, SNPs may be frozen, banked and then thawed when used for seeding chips or used to directly seed chips, see Example 6, below.

B. BMEC Differentiation.

Cells are thawed (or dissociated fresh) and seeded into the chip at day 8-9 (in the case of BMECs differentiation) and at various points in neural differentiation. BMECs were differentiated as described previously (Lippmann, Al-Ahmad et al. 2014).

Figure 48:
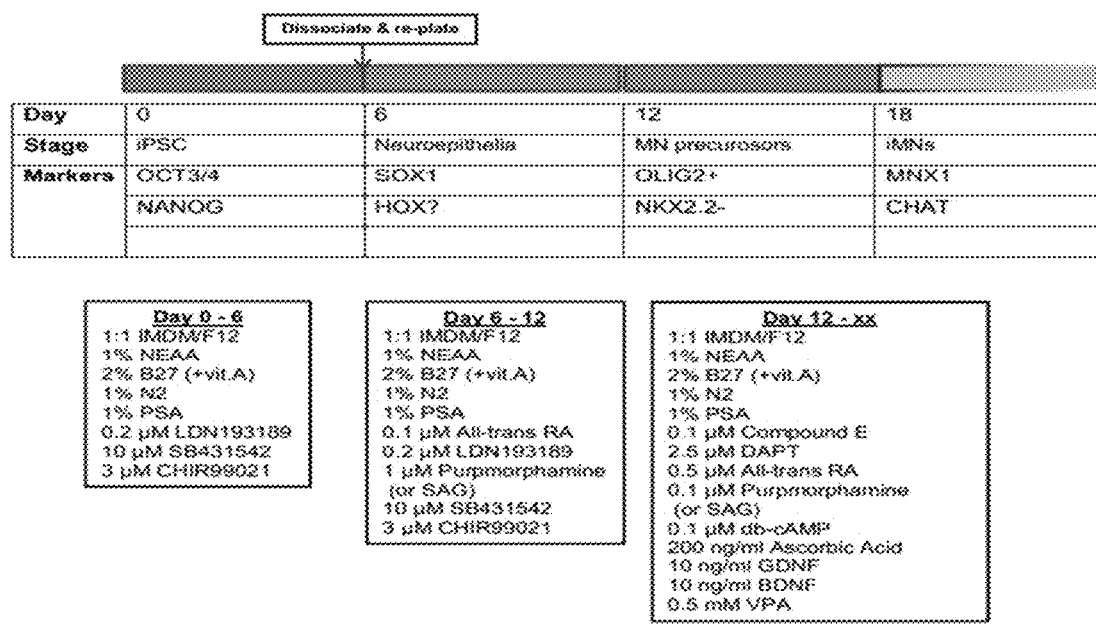
FIG. 48 illustrates exemplary materials and methods for one embodiment including factors used in the protocol for the generation of motor neurons (using iPSCs as the starting material).

FIG. 48 illustrates exemplary materials and methods including factors used in the protocol for the generation of motor neurons (using iPSCs as the starting material).

Example 2

In this example, another protocol for the generation of motor neurons is provided using iPSCs as the starting material.

Figure 49:
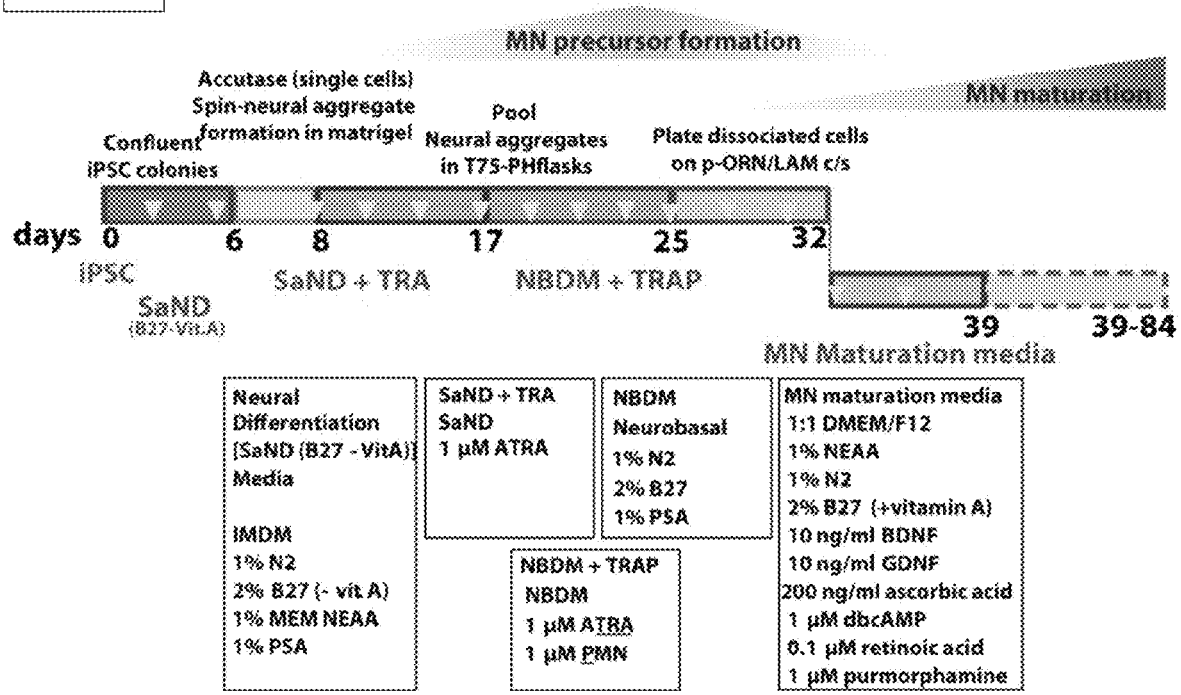
FIG. 49 illustrates exemplary materials and methods for one embodiment including various factors used in the protocol for the generation of motor neurons are provided (using iPSCs as the starting material).

FIG. 49 illustrates exemplary materials and methods for one embodiment including various factors used in the protocol for the generation of motor neurons are provided (using iPSCs as the starting material).

Example 3

This example explores various conditions tested for seeding neural (EZ spheres and iMNPs) and endothelial cells (iBMECs) from frozen stocks of cells on surfaces treated with different extracellular matrices (ECMs). The best results for iBMECs were achieved with a mixture of collagen and fibronectin (4:1 ratio) using a seeding concentration of $5 \times 10^6$ (FIG. 50). Given these results, seeding was attempted on microfluidic devices, i.e. chips. Table 1 shows various conditions tested for seeding neural (EZ spheres, iNPCs and iMNPs) and endothelial cells (iBMECs) on the apical and basal sides of a microfluidic chip using frozen stocks of cells.

Figure 2:
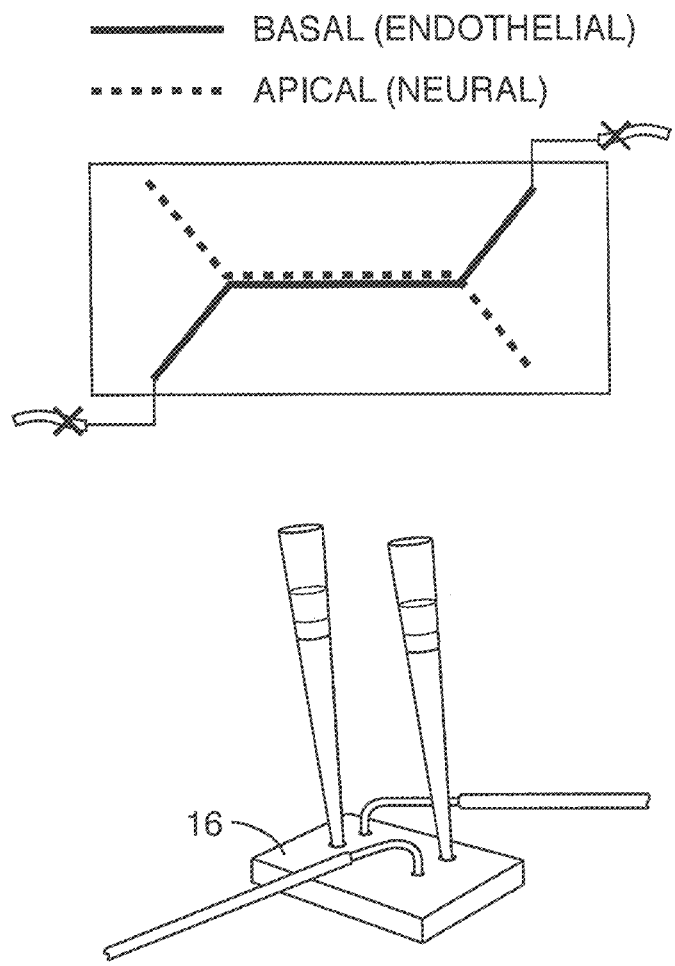
FIG. 2 shows two schematics of microfluidic devices. In one embodiment of a microfluidic device or chip (top), the device comprises top (apical) and bottom (basal) channels (the two Xs indicating that channels are blocked during at least part of the protocol). The other schematic (bottom) shows how the ports of a microfluidic device or chip (16) can be utilized to deposit fluids carrying surface coatings (e.g. dissolved proteins) and/or seed the cells using pipette tips. This image shows a modification to the typical chip ECM coating protocol based on the need in some embodiments to coat the top and bottom channels with different ECM solutions in wet and dry conditions. The procedure developed involved an "air dam" by which perfusion of ECM1 loaded into the bottom channel was prevented from perfusing through the membrane to the top channel by clamping flexible tubing and trapping air in the top channel. The ports of a second microfluidic channel can be air-filled and plugged up using clips, for example.

While a variety of protocols were explored, one embodiment for preparing and seeding a microfluidic chip comprising six steps. FIG. 1 shows the workflow. First, the chip (or regions thereof) are treated to promote wetting or protein adhesion (e.g. by plasma treatment). One or more channels are then plugged (see the top schematic of FIG. 2, where an "X" indicates a channel is blocked in a microfluidic device or chip with top and bottom channels). FIG. 2 (bottom schematic) shows how the ports of a microfluidic device can be utilized to introduce fluid (e.g. with ECMs) or cells using pipette tips. Using the protocol, the ECM mixture for the bottom channel is introduced first, with the excess removed, and the remainder dried. Thereafter (step 3), the ECM for the top channel is introduced. The BMECs can be seeded on the bottom channel. The top channel can be washed. Finally, the neural cells can be introduced and incubated for attachment. Cultures were seeded into chips following the seeding of BMECs described above either on the same day or the following day after BMECs had been seeded onto the chip. The chips were cultured for 14 days and fixed and stained for relevant markers. Confocal imaging shows the transmigration in z-stack.

Figure 3A:
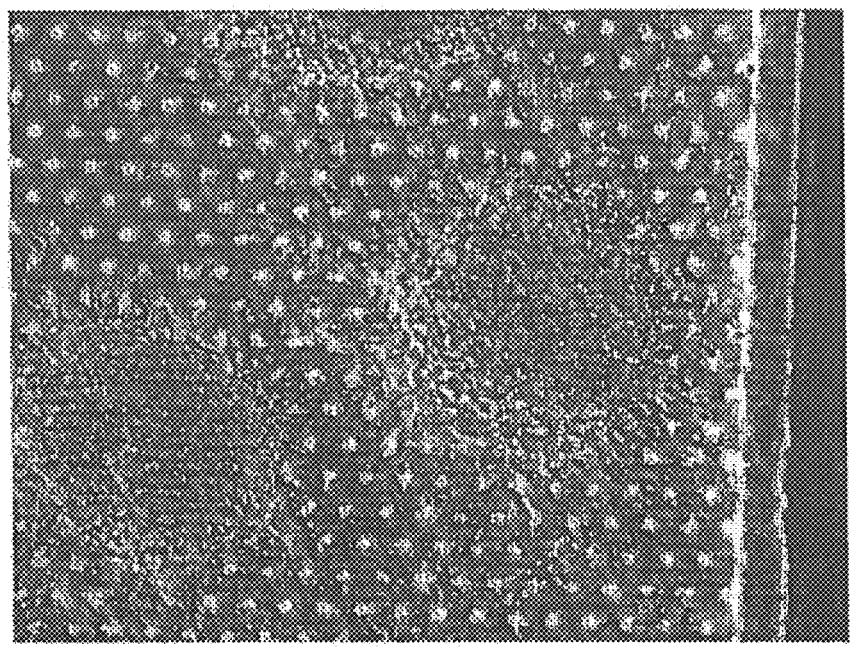
FIG. 3A-B provides a microscopic analysis of Chip 166 from Table 3, showing neural cells in the top channel of the microfluidic device (FIG. 3A) and BMECs on the bottom channel of the microfluidic device (FIG. 3B).
Figure 3B:

FIG. 3A-B provides a microscopic analysis of Chip 166 from Table 1, showing neural cells in the top channel of the microfluidic device (left) and BMECs on the bottom channel of the microfluidic device (right). The neural cells and BMECs have attached.

Figure 4B:
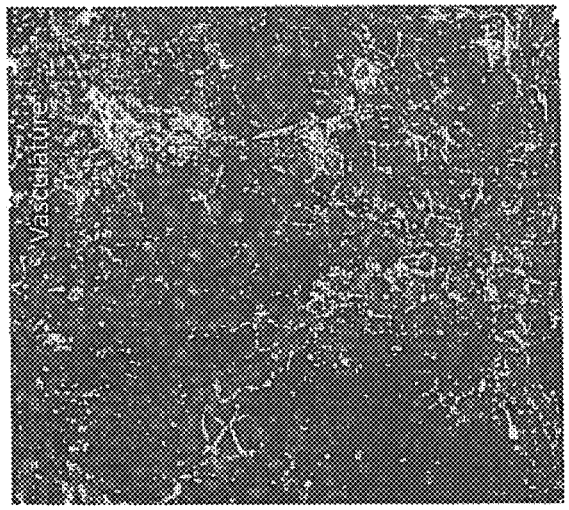
FIG. 4A-C provides three images from a microfluidic chip where the cells have been tested for markers to confirm their identity. The top right image (FIG. 4B) shows good staining of BMEC tight junctions indicating BBB formation on chip. On the top left (FIG. 4A), the staining shows neurons and astrocytes.
Figure 4A:
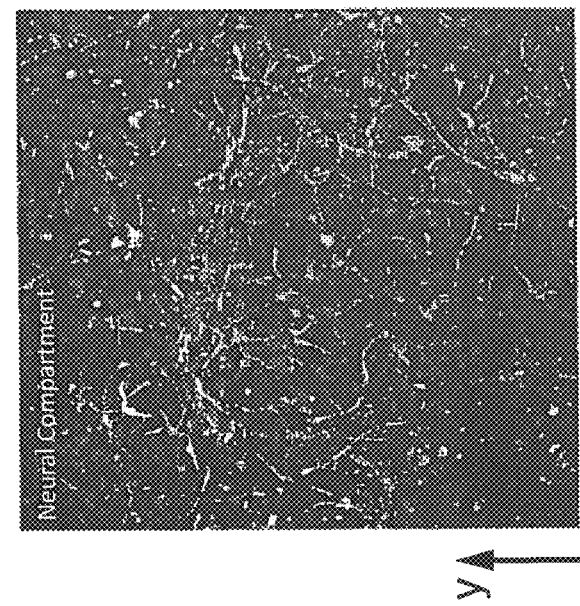
Figure 4C:
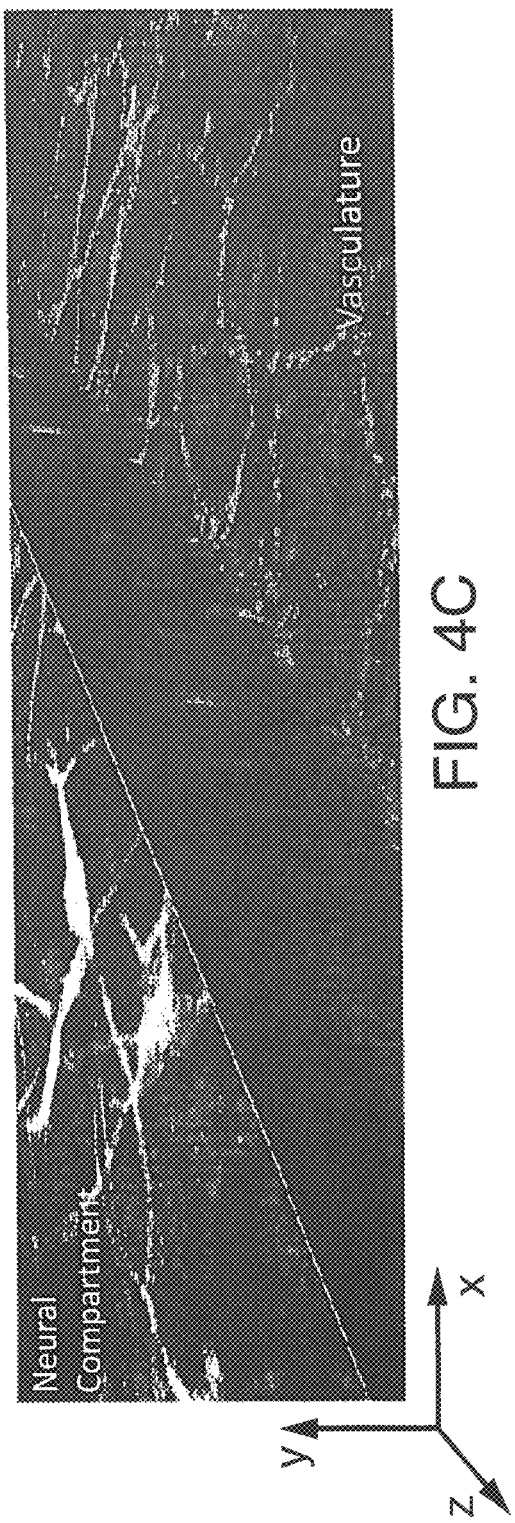

The attached cells were then tested for markers to confirm their identity. FIG. 4A-C is a vertical 2D projection of a 3D confocal stack of images slices, which allows for visualization of the neurons and endothelial cells together, even though they are not in the same plane on the microfluidic device. The BMECs display the Glut 1 marker, while the neurons are positive for NFH. DAPI was used to stain the nuclei.

Figure 5:
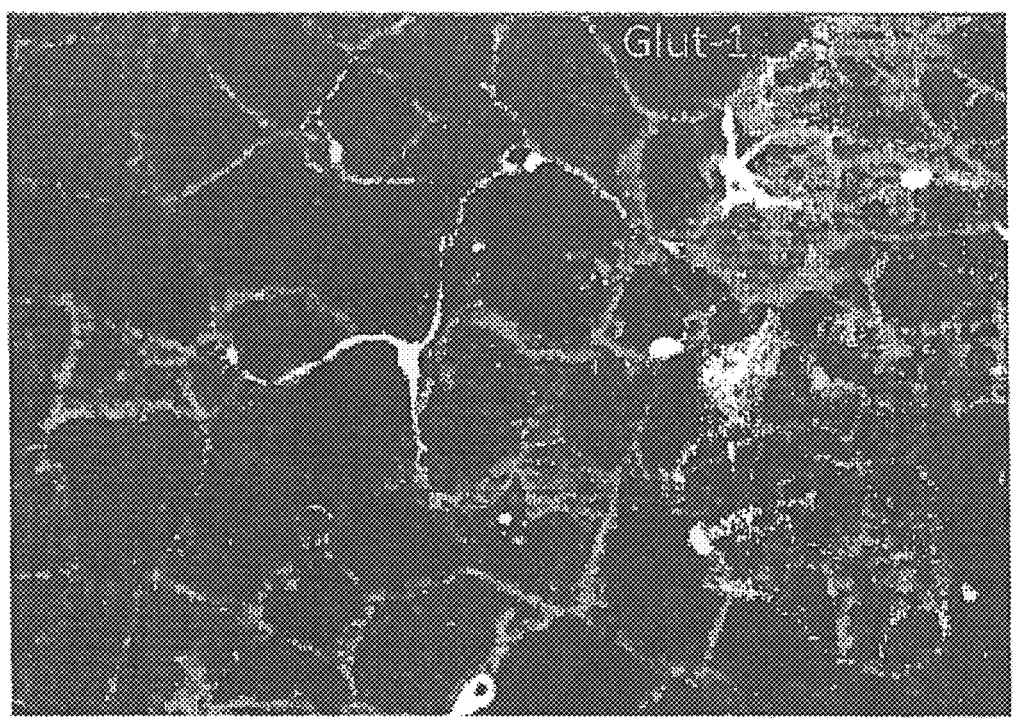
FIG. 5 provides an image from a microfluidic chip wherein at least a portion of an apical astrocyte (i.e. the endfoot) has transmigrated the membrane and contacted the BMECs on the other side. Contact or interfacing between astrocytes and endothelial cells is a recognized feature of in vivo blood-brain barriers. To our knowledge, this interface has never been previously observed in in vitro models of the blood-brain barrier. The potential for the formation of astrocyte-endothelial contact observed in some of the embodiments disclosed herein is desired and advantageous, as it is believed that the in vivo contact/junction is related to the tight barrier properties characteristic of the blood-brain barrier.

FIG. 5 provides an image from a microfluidic chip wherein at least a portion of an apical astrocyte (i.e. the endfoot) has transmigrated the membrane and contacted the BMECs on the other side. The astrocytes are shown in white against the red stained BMECs.

Example 4

Figure 6A:
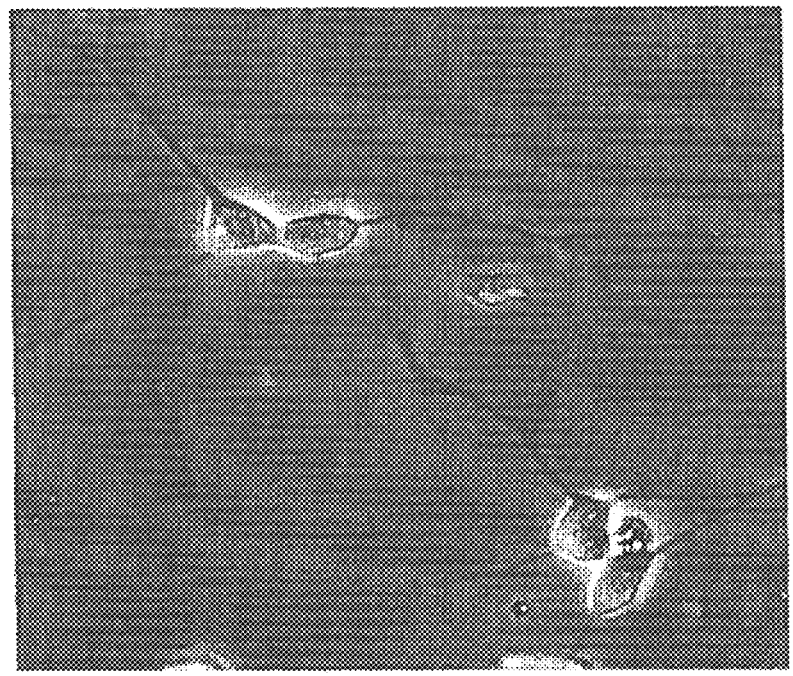
FIG. 6A-B shows a first image (FIG. 6A) where iMNs were seeded on a plain (un-patterned) surface, as well as a second image (FIG. 6B) where the same cells were seeded on a nanopatterned surface, resulting in directed neurite growth. Such nanopatterning can be applied to the membrane or any surface of the BBB-on-chip. In particular embodiments, the nanopatterning is applied to the top surface of the membrane to direct neurite growth for neuron seeded on said surface. It is desired in some uses to direct neurite growth, for example, in studying neuron biology or disease (e.g. conditions that disturb neurite growth or its directionality), as a readout of neuron or blood-brain-barrier health (e.g. by monitoring neurite growth or its directionality) or in facilitating electrophysiological measurements (e.g. using a multi-electrode array or patch clamping). The preferred nanopattern is linear valleys and ridges, but alternatives such as circular, curved, or any other desired shape or combination thereof are also contemplated. Linear nanopatterning can include, for example, line spacing ranging from 10 nm to 1 um, 0.5 um to 10 um or 5 um to 50 um, and line depth ranging from 10 nm to 100 nm, to 1000 nm, 200 nm to 5 um or 20 um to 50 um.
Figure 6B:
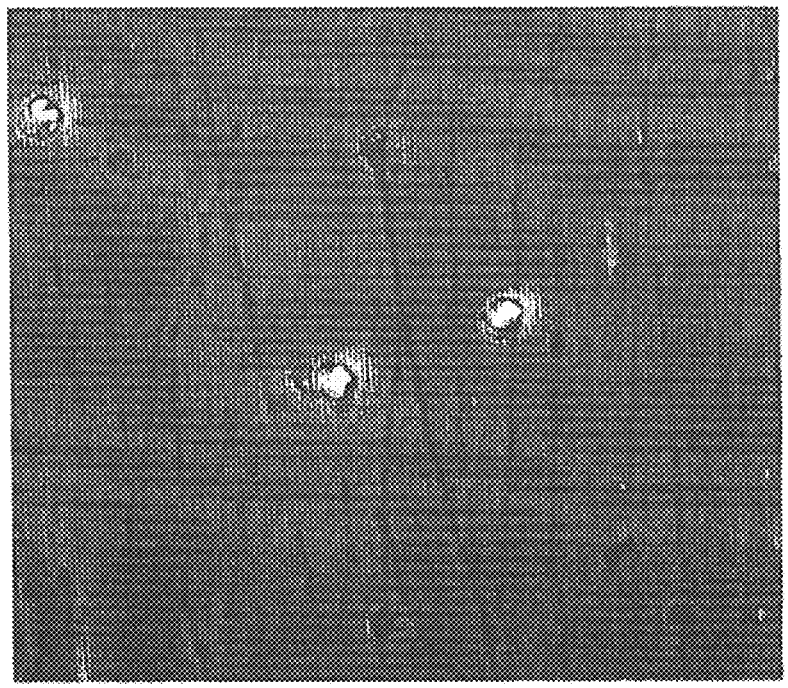

The present invention contemplates, in one embodiment, utilizing nanopatterned surfaces for seeding cells. FIG. 6A-B shows a first image (top) where iMNPs were seeded on a plain (un-patterned) surface, as well as a second image (bottom) where the same cells were seeded on a nanopatterned surface. Clearly, the nanopatterned surface results in directed neurite growth (e.g. in a line pattern)

Example 5

Figure 7A:
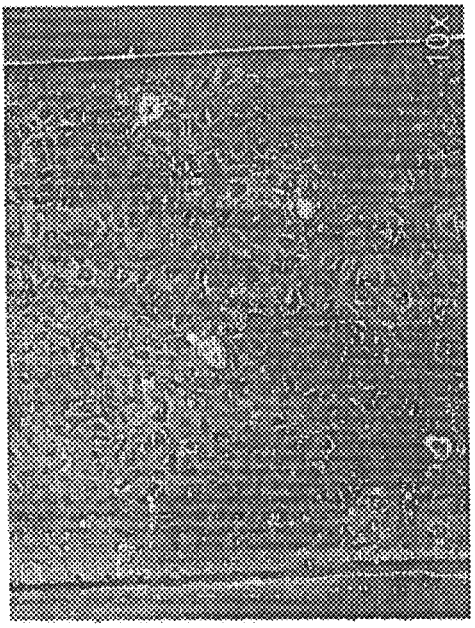
FIG. 7A-D show microscopic examination of the morphology of fresh (not frozen) BMECs seeded on a 4:1 mixture of collagen and fibronectin that has either been dried (FIG. 7A, top left) or remained wet (FIG. 7B, top right), as well as an example where the same fresh cells were seeded on laminin (FIGS. 7C and D, the arrow indicating contamination of the cells with neurons).
Figure 7B:
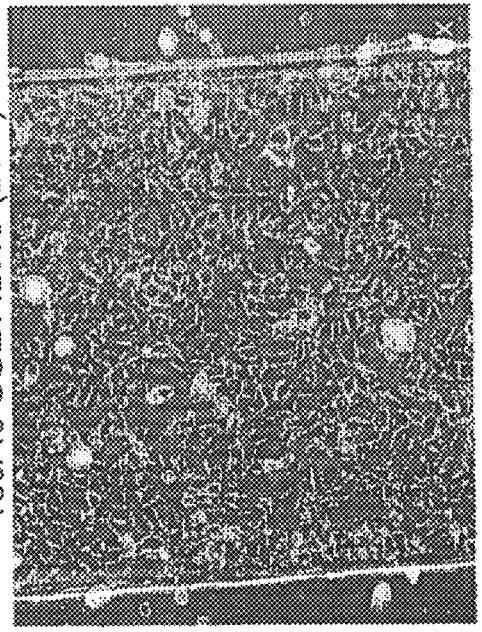
Figure 7C:
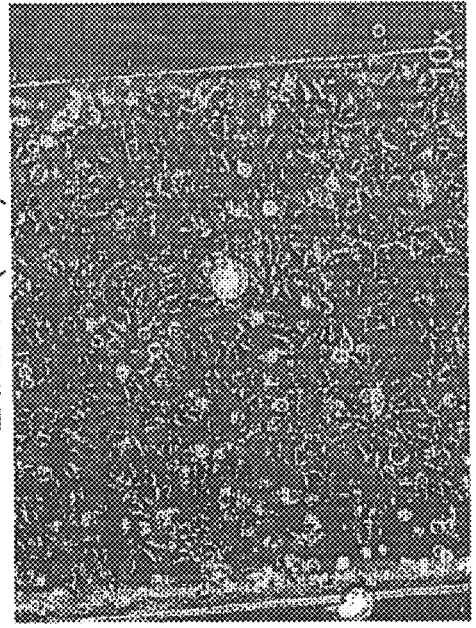
Figure 7D:
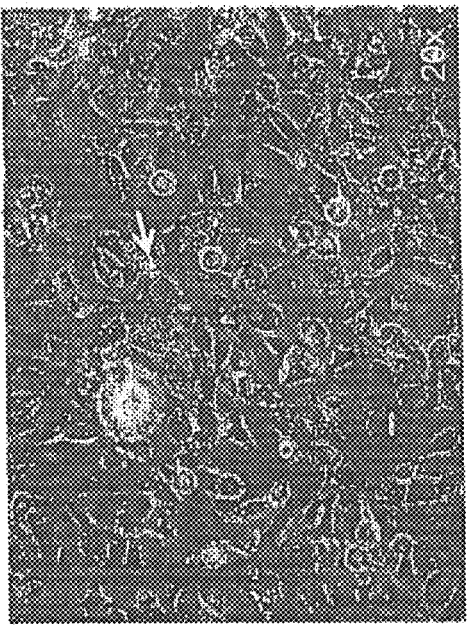

While frozen stocks of cells can be used (particular for the neural cells), it was found that better results can be obtained (particularly for BMECs) when fresh cells are used for seeding. FIG. 7A-D show microscopic examination of the morphology of fresh (not frozen) BMECs seeded on a mixture of collagen and fibronectin that has either been dried (FIG. 7A, top left) or remained wet (FIG. 7B, top right), as well as an example where the same fresh cells were seeded on laminin (FIGS. 7C and D). Interestingly, when laminin was used, the BMECs were not free of neurons (see the arrow in FIG. 7D indicating contamination of the cells with neurons).

Tables 2 and 3 show various conditions tested for seeding fresh neural (iMNPs) and fresh endothelial cells (iBMECs), where the particular conditions are associated by microfluidic chip number, allowing for a correlation of good tight junctions with the seeding conditions. Staining results (not shown) for microfluidic chip 574 (see Table 2 for conditions) indicated the cells are positive for Glut 1 (red stain), which is a marker of BMEC tight junctions (the nuclei were also stained blue from DAPI). The seeding conditions for chip 574 resulted in good tight junctions. Staining results (not shown) for microfluidic chip 665 (see Table 2 for conditions) indicated that the cells are positive for Glut 1. Thus, the seeding conditions for chip 665 also resulted in good tight junctions. Staining results (not shown) for microfluidic chip 667 (see Table 2 for conditions) indicated the cells are positive for Glut 1. Thus, the seeding conditions for chip 667 resulted in good tight junctions. Staining results (not shown) for microfluidic chip 693 (see Table 2 for conditions) indicated the cells are positive for Glut 1. Thus, the seeding conditions for chip 693 resulted in good tight junctions.

Staining results (not shown) for microfluidic chip 733 (see Table 3 for conditions) indicated the cells are positive for Glut 1. The results (not shown) also revealed that coating with laminin alone (before seeding) results in poor BMEC tight junction formation.

Example 6

Seeding Chips Using Day 12 Spinal Neural Progenitor (SNP) Cells.

SNPs (fresh or thawed) were seeded into the top channel of the SC-chip and incubated for 6 days. SNPS or MNs were cultured in Stage 3 media (after day 12) consisting of IMDM/F12 (Gibco), B27, N2, 1% NEAA, 200 ng/ml ascorbic acid, 0.5 uM retinoic acid, 0.1 uM cAMP, 0.1 uM SAG, 10 ng/ml GDNF, 10 ng/ml BDNF, 1% PSA and fed every two days.

After 6 days, cultures underwent immunostaining of cells in the main channel of the chip, including but not limited to markers of spMNs SMI32, nuclear marker islet1 (ISL1), Beta 3 tubulin (TUBB3), NKX6.1, neurofilament marker microtubule-associated protein 2 (MAP2), and synaptic marker synaptophysin (SYNP).

FIG. 32A-G Exemplary Spinal Neural Progenitor (SNP) Neurons Survive And Mature In The Chip Microenvironment. FIG. 32a Schematic of Spinal neural progenitor (SNP) differentiation from induced pluripotent stem cell (iPSC) cultures. Cells were fated to neural ectoderm (NE) using WNT agonist CHIR99021 and SMAD inhibitors LDN193189 and SB431542 for 6 days then patterned to ventral spinal neurons using Retinoic Acid (RA) and Sonic hedgehog agonist (SAG) in 6-well plates. At day 12, SNPs were frozen, banked and thawed for experiments (Cryobank). SNPs were seeded into the top channel of the SC-chip (dotted line) and incubated for 6 days. FIG. 32b Schematic of dual-channel organ chip seeded with SNPs in top channel. FIG. 32c Phosphorylated neurofilament heavy chain (SMI32) is enriched in spinal motor neurons (spMNs) and expressed in cells populating entire top channel. Scale bar=200 microns. FIG. 32d Immunostaining of main channel of the chip of markers of spMNs SMI32, nuclear marker islet1 (ISL1), Beta 3 tubulin (TUBB3), NKX6.1, neurofilament marker microtubule-associated protein 2 (MAP2), and synaptic marker synaptophysin (SYNP), scale=200 microns (left); 40 microns (right). FIG. 32e Representative image of SC-chip neurons treated with Fluo-4 calcium activated dye and acquired live in FITC channel. FIG. 32f Florescence of individual active neurons normalized to baseline florescence and plotted over time (dF/F). FIG. 32g Raster plot showing detected events of corresponding traces.

Example 7

Seeding Chips Using Day 12 Spinal Neural Progenitor (SNP) Cells and BMECs in SC-Chip.

Tall channel microphysiological systems (Emulate Inc.) were treated with plasma in 100% oxygen for 2:00 minutes and immediately coated with MATRIGEL® substrate for the neural channel and a mixture of collagen IV (Invitrogen), Fibronectin (Invitrogen), and diluted in water in a ratio of 1:4:5 respectively, and incubated overnight at 37° C. and 5% $CO_2$. Chips were seeded with MNs and BMECs on the same day sequentially by flipping the Chip and allowing cells to attach to the membrane by gravity. Chips were fed with approximately 25 uL of Stage 3, with an extra 25 uL in reservoir tips and media was replaced every other day.

FIG. 33A-H Exemplary Co-culture of iPSC derived MNs and BMECs in SC-Chip. FIG. 33a Schematic of dual-differentiation and seeding paradigm in EC/SC-Chip. Both SNPs and BMECs are generated from human iPSCs and seeded into top and bottom channels respectively. Transverse section of the EC/SC-Chip (right) shows two compartments separated by porous membrane. FIG. 33b Immunostaining of whole SC-Chip at 6-days incubation expressing SMI32 in top channel and ISL1 expressed by BMECs on bottom channel. FIG. 33c Maximum projection images cropped along Z-axis to show top and bottom compartments of seeding end of EC/SC-Chip immunostained with MN markers SMI32 and islet 1 (ISL1), and tight junction marker zona occludens 1 (ZO-1), Scale bar=400 microns (left) 40 microns (right). FIG. 33d Confocal optical reconstruction at along Z axis (top) of SC-Chip exhibits distinct separation of cultures at 6 days separated by porous PDMS membrane. Perspective view (bottom) exhibits confluent layer of BMECs surrounding entire bottom channel, Scale bar=100 microns. FIG. 33e Representative images of cells attached to porous membrane in the main channel (top and bottom planes). SC-Chip was seeded either with SNPs alone in the top channel (SC-Chip) or with the addition of non-GFP BMECs into the bottom compartment (EC/SC-Chip). FIG. 33f High magnification of top compartment show GFP negative, ISL1 positive clusters indicating BMEC infiltration. Quantification of FIG. 33g GFP and FIG. 33h ISL1 populations in top compartment. Error bars represent standard deviation. Plots were determined from 6 individual chips from three culture rounds (dots). No significant difference cultures determined by t-test (ns). FIG. 34A—H: SC-Chip environment increases spontaneous neural activity.

FIG. 34A-H Exemplary SC-Chip environment increases spontaneous neural activity. FIG. 34a Individual Representative calcium transient activity of SNP (top) and BMEC (bottom) cultures acquired at the seeding compartments plotted by change in florescence intensity over background (dF/F) with respect to time totaling 180 seconds. FIG. 34b Calcium transient activity plots of 30 representative neurons from each culture condition. Transient frequency of 194-297 neurons spanning three separate replicates per condition calculated in two individual lines FIG. 34c 83GFP and FIG. 34d 00iCTR. Neuron activity completely ablated with the administration of tetrodotoxin (TTX). FIG. 34e Immunocytochemistry staining of islet1 (ISL 1) and smi32 (right) of site previously acquired for live calcium transients using fluro-4 dye (left). ISL1+ neurons (arrows) superimposed to determine MN firing specificity. FIG. 34f Mean transient frequency of representative active neurons compared to ISL1 overlaid MNs. Charts showing representative transient events from FIG. 34g ISL1 SMI32 double-positive neurons quantified and displayed as raster plot and plotted in FIG. 34h as frequency in hertz (Hz). Means represented by black bars and error bars represent standard error of the mean. Significance calculated by ANOVA,  denotes $P<0.01$, *=$P<0.005$, and ****=$P<0.001$.

FIG. 35A-I Exemplary SC-Chip induces neural differentiation and vascular interaction gene expression. FIG. 35a GFP-MN isolation schematic: nuclear GFP expressing SNPs seeded on top channel with isogenic non-GFP expressing BMECs on bottom. Fluorescence-assisted cell sorting (FACS) conducted on FITC to purify spMNs after BMEC co-culture. FIG. 35b Single population histogram of chips seeded only with non-GFP BMECs (black) or GFP-MNs (green) that defined negative and positive fractions respectively. Number of events displayed on y-axis and FITC intensity on x-axis FIG. 35c Mean RPKM data of purified SC-Chip and EC/SC-Chip cultures normalized to RPKM data from iPSC derived BMECs cultured alone. Canonical markers claudin 5 (CLDN5), occluding (OCLN), Tight junction protein 1 (TJP1), Glut-1 (SLC2A1), von willebrand factor (VWF), Tie2 receptor (TEK), endoglin (ENG), and melanoma cell adhesion molecule (MCAM). FIG. 35d Principle component analysis plots of first two principle components (PC) (top) and PCs 2, and 3 (bottom). Arrows indicate weighting along the axis of each respective PC. FIG. 35e Top 200 ranked genes from each PC displayed as Z-score calculated across all conditions for each row and indicated by colorimetric scale. Each PC was entered into DAVID ontology pathway analysis and top 7 categories listed for each PC. The number of genes (count) in each category is displayed with corrected significance values from DAVID analysis (Bonferonni). FIG. 35f FIG. 35g Differentially expressed genes contributing to the "Response to Protein Stimulus" and "Neural Differentiation" DAVID terms enriched in PC2. RPKM data averaged across sample replicates and normalized to 96W control. (FIG. 35h, FIG. 35i) Differentially expressed genes contributing to "Vascular Development" and "Extracellular Matrix" DAVID terms enriched in PC3.

FIG. 36A-E Exemplary BMECs Induce Vascular Interaction Gene Expression In Chip. FIG. 36a PCA comparing expression data of differentially expressed genes from PC2 and PC3 and including in vivo adult laser captured MNs (green), in vivo fetal spinal cord (purple), and in vitro experimental data. FIG. 36b Heatmap of top ranking genes from Dev-PC2 that describe variance in fetal gene expression. Z-score calculated from $Log_2$ RPKM data per gene row and displayed by colorimetric scale. FIG. 36c Mean Somatostatin (SST) expression plotted for each condition, error bars represent standard deviation. FIG. 36d Representative images of 96 well (96W) and SC-Chips co-cultured with BMECs (EC/SC-Chip) immunostained with SST and MN markers SMI32 and ISL1, scale bars=40 microns. FIG. 36e Whole mount image of day 67 human fetal spinal cord (top) immunostained with SST, SMI32 and ISL1. Higher magnification of ventral horn ISL1 positive MN pool (box) co-expressing SST (bottom).

FIG. 37A-D Shows an illustrative comparison of fetal developmental stages (week 2 through birth) to differentiation of specialized cell types, including Motor Neurons, Endothelial Cells, Skeletal Muscle Cells and Astrocytes and examples of cell staining. FIG. 37a Schematic of relative emergence of cell types that directly interact with developing human MNs in vivo. FIG. 37b Days 53 and 67 human fetal spinal cords immunostained with neuronal marker neuofilament heavy chain (NFH), BMEC marker glucose transporter 1 (GLUT1), and transcription factor ISL1. High magnification of ventral horns (box) show ISL1 positive MN pools (yellow dotted line). FIG. 37c Images of iPSC-derived BMECs cultured in 96-well plate for 6 days and immunostained with GLUT 1, ISL1, and tight junction markers zona occludens 1 (ZO-1) and Occludin (OCLDN). FIG. 37d Images of SNPs cultured in 96W plate and immunostained with markers of spMNs SMI32, nuclear marker islet 1 (ISL1), Beta 3 tubulin (TUBB3), NKX6.1, neurofilament marker microtubule-associated protein 2 (MAP2), and synaptic marker synaptophysin (SYNP).

FIG. 37A-D Shows an illustrative comparison of fetal developmental stages (week 2 through birth) to differentiation of specialized cell types, including Motor Neurons, Endothelial Cells, Skeletal Muscle Cells and Astrocytes and examples of cell staining. FIG. 37a Schematic of relative emergence of cell types that directly interact with developing human MNs in vivo. FIG. 37b Days 53 and 67 human fetal spinal cords immunostained with neuronal marker neuofilament heavy chain (NFH), BMEC marker glucose transporter 1 (GLUT1), and transcription factor ISL1. High magnification of ventral horns (box) show ISL1 positive MN pools (yellow dotted line). FIG. 37c Images of iPSC-derived BMECs cultured in 96-well plate for 6 days and immunostained with GLUT 1, ISL1, and tight junction markers zona occludens 1 (ZO-1) and Occludin (OCLDN). FIG. 37d Images of SNPs cultured in 96W plate and immunostained with markers of spMNs SMI32, nuclear marker islet 1 (ISL1), Beta 3 tubulin (TUBB3), NKX6.1, neurofilament marker microtubule-associated protein 2 (MAP2), and synaptic marker synaptophysin (SYNP).

FIG. 38A-C An Exemplary Comparison Of Gene Expression Showing Density Plots And Comparison Of Datasets. FIG. 38a Density plots of 10,001 genes for each sample for transcriptomic analysis. Quantile normalized data (right). FIG. 38b Pierson correlation coefficient analysis of normalized RPKM datasets displayed by colorimetric scale. FIG. 38c Notch pathway genes differentially expressed in the SC-Chip conditions.

FIG. 39A-B An Exemplary Comparison Of Gene Expression Between Density And Principle Component Analysis (PCA). FIG. 39a Density plots of 10,001 genes of developmental comparison containing adult laser captured MNs (green: peaks on the left), fetal Spinal cord (purple: peaks on the right) and sorted iPSC-derived neurons (black: middle peaks); upper graph. Quantile normalized data (bottom). FIG. 39b PCA analysis of variance across all samples and all 10,001 genes. Adult laser captured MNs (green: upper left dots), fetal Spinal cord (purple: cluster of dots on the left) and sorted iPSC-derived neurons (black: lower left dots). Quantile normalized data (bottom).

Example 8

Figure 8:
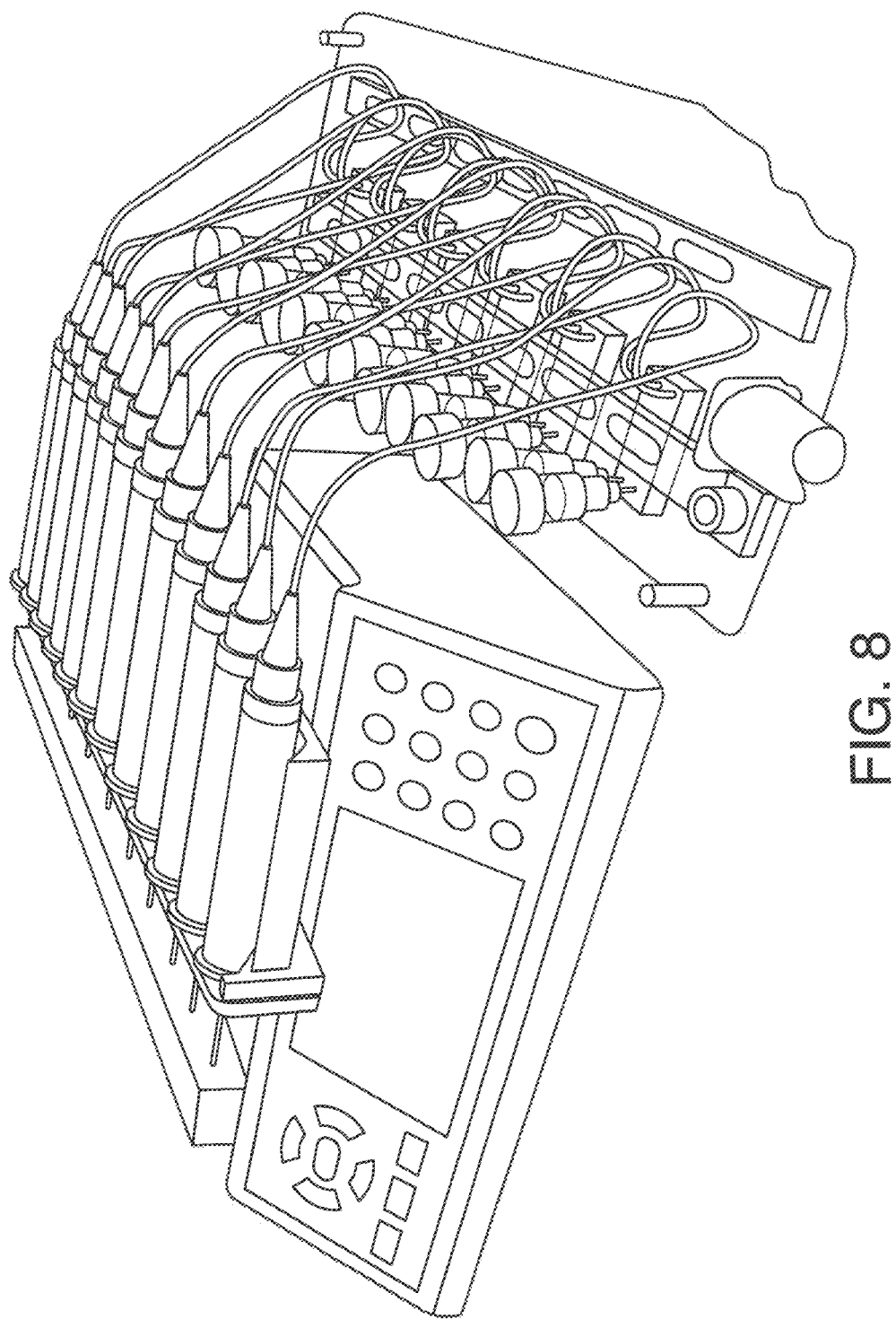
FIG. 8 is a schematic showing one embodiment of a standard syringe pump and reservoir setup for perfusion of the chips mediated by flexible tubing for introducing flow into the microfluidic chips. A plurality of fluid reservoirs are in fluidic communication with a corresponding plurality of microfluidic chips via inlet ports, with tubing coming from the exit ports and attached to a plurality of syringes used to draw fluid through the chip at a flow rate. While a convenient method for creating flow conditions, other methods involving different pumping approaches or pressure approaches to drive fluid are contemplated.
Figure 9A:
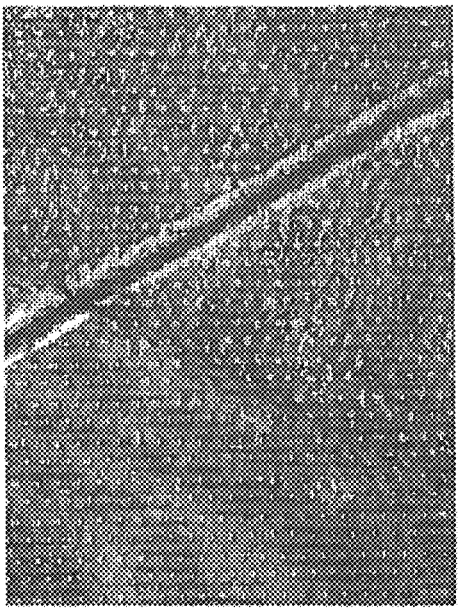
FIG. 9A-D comprises photographs of microscopic examination of cell morphology on the bottom (left-hand side) and top (right-hand side) of the membrane in a microfluidic device where the cells have been exposed to flow (using the system of FIG. 8) for a number of days (7 days).
Figure 9B:
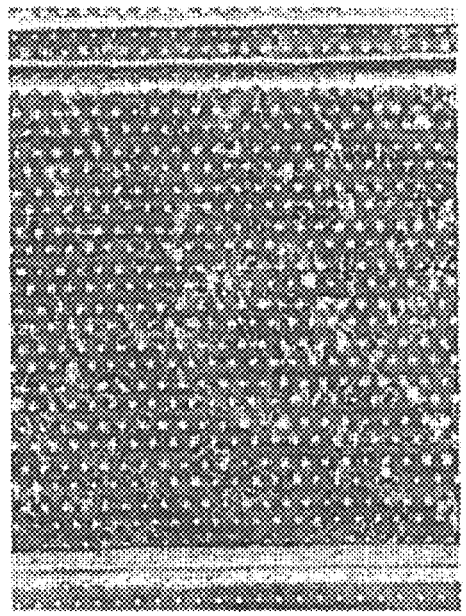
Figure 9C:
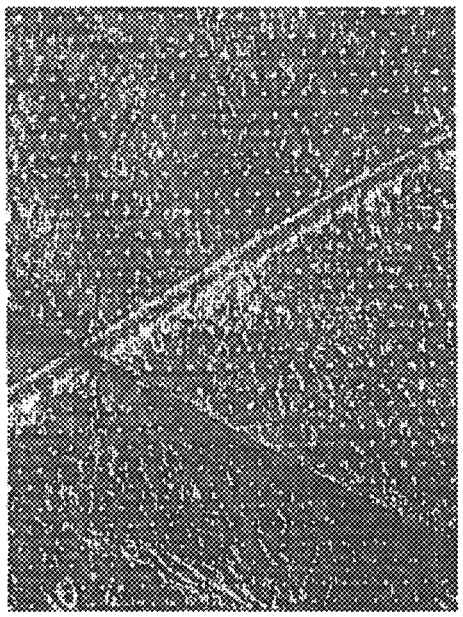
Figure 9D:
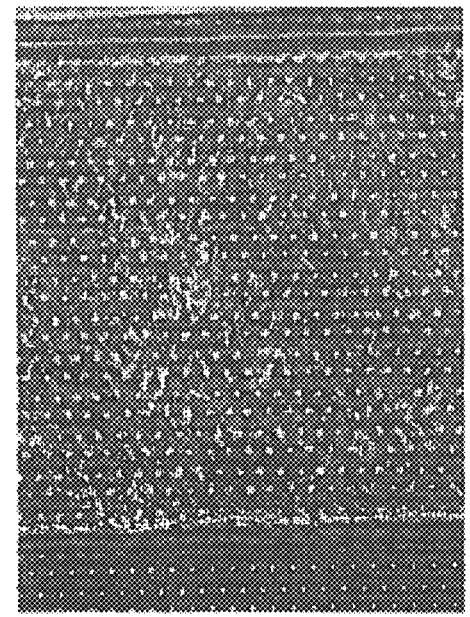
Figure 10:
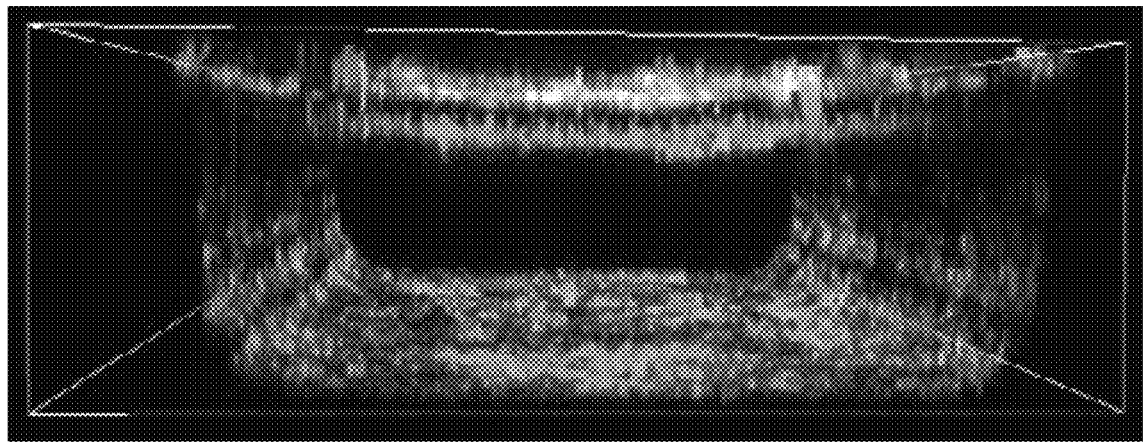
FIG. 10 is a photograph of fluorescent staining of cells in a microfluidic device where the cells have been exposed to flow (using the system of FIG. 8) for a number of days. The image is a 3D image of the BMEC in the bottom channel showing a complete contiguous BMEC lumen being formed in the chip.
Figure 11:
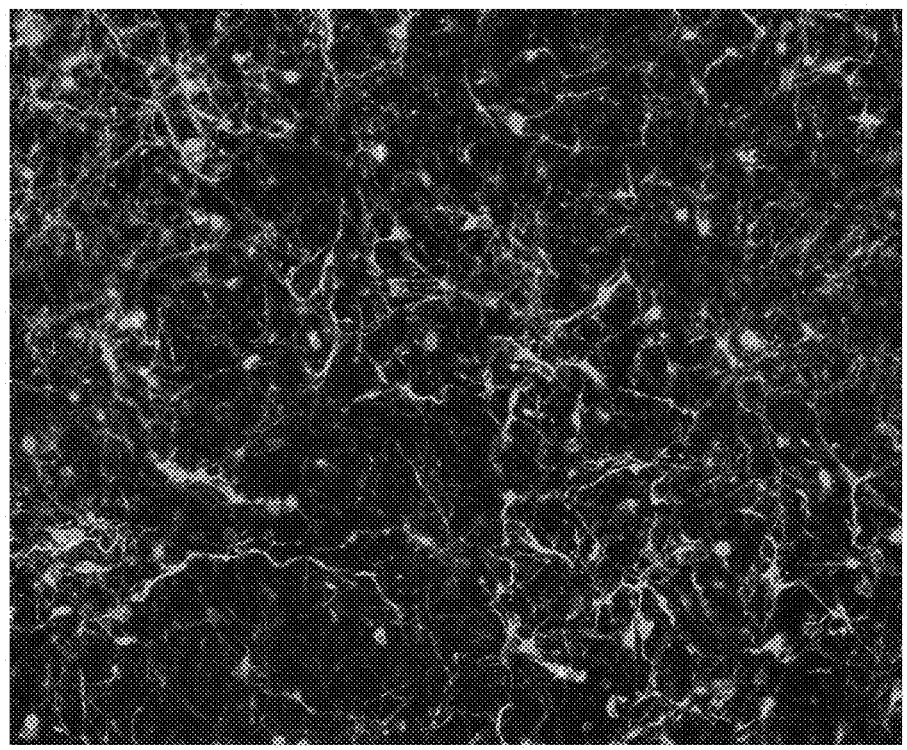
FIG. 11 is a photograph of fluorescent staining of cells showing the presence of neural stem cells (red) in addition to neural filaments (green), with the nuclei stained with DAPI. In the preferred embodiment, the BBB-on-chip includes endothelial or endothelial-like cells (preferably brain-related endothelial cells) and optionally astrocytes or astrocyte-like cells. However, in some embodiments, the BBB-on-chip contains additional cells type such as, for example, neurons, pericytes and various progenitor cells. Such cells may be included as an intended or unintended bi-product of the stem cell differentiation process from which the astrocytes or endothelial cells are generated (whether on chip or preceding it), as stem cells and progenitor cells are typically capable of differentiating into a plurality of cells types. The presence of neurons is desirable in some embodiments because they can be used as readouts of BBB function (e.g. agents penetrating the barrier may affect the neurons in measurable ways) or because they may interact with other cells types or help generate a local environment that improves the function of the BBB-on-chip. Similarly, pericytes are desirable in some embodiments, because it is believed in the art that they help establish the blood-brain barrier and can be potentially monitored to evaluate BBB health. Neuronal- or endothelial-lineage progenitors are desirable in some embodiments, as they may replenish cell populations and be potentially monitored to evaluate BBB health. Accordingly, in some embodiments, neurons, pericytes, neuronal-lineage progenitors, endothelial-lineage progenitors or combinations thereof or progenitors thereof may be deposited in the BBB-on-chip. In other embodiments, a differentiation process is employed (whether on chip or preceding it) to generate one or more of these cells types.

Unlike conventional static cultures, the present invention contemplates microfluidic devices where the cells are exposed to a constant flow of media providing nutrients and removing waste. FIG. 8 is a photograph showing one embodiment of a system for introducing flow into the microfluidic chips. A plurality of fluid reservoirs are in fluidic communication with a corresponding plurality of microfluidic chips via inlet ports, with tubing coming from the exit ports and attached to a plurality of syringes used to draw fluid through the chip at a flow rate. FIG. 9A-D comprises photographs of microscopic examination of cell morphology on the bottom (left-hand side) and top (right-hand side) of the membrane in a microfluidic device where the cells have been exposed to flow (using the system of FIG. 8) for a number of days. FIG. 10 shows fluorescent staining of cells in a microfluidic device where the cells have been exposed to flow (using the system of FIG. 8) for a number of days. The image is a 3D image of the BMEC in the bottom channel showing a complete contiguous BMEC lumen being formed in the chip. FIG. 11 is a photograph of fluorescent staining of cells showing the presence of neural stem cells (red) in addition to neurites (green), with the nuclei stained with DAPI.

Example 9

Good cell viability and function on the BB-on-chip allow for measurements of barrier integrity and physiology, whether by TEER, patch clamp or other testing measures.

Figure 12A:
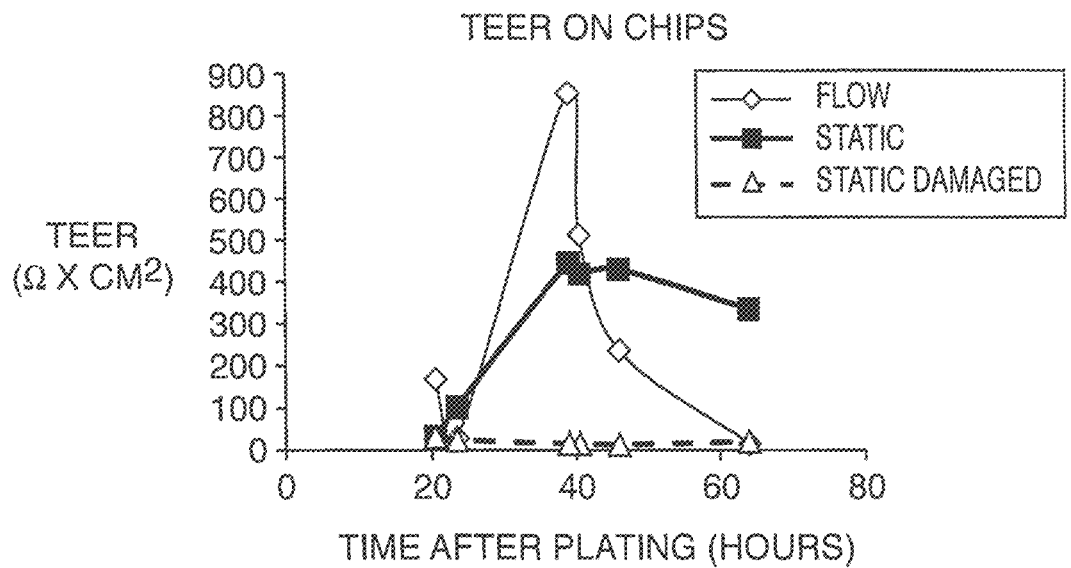
FIGS. 12A and 12B show graphs with functional measurements performed on BBB-on-chips.
Figure 12B:
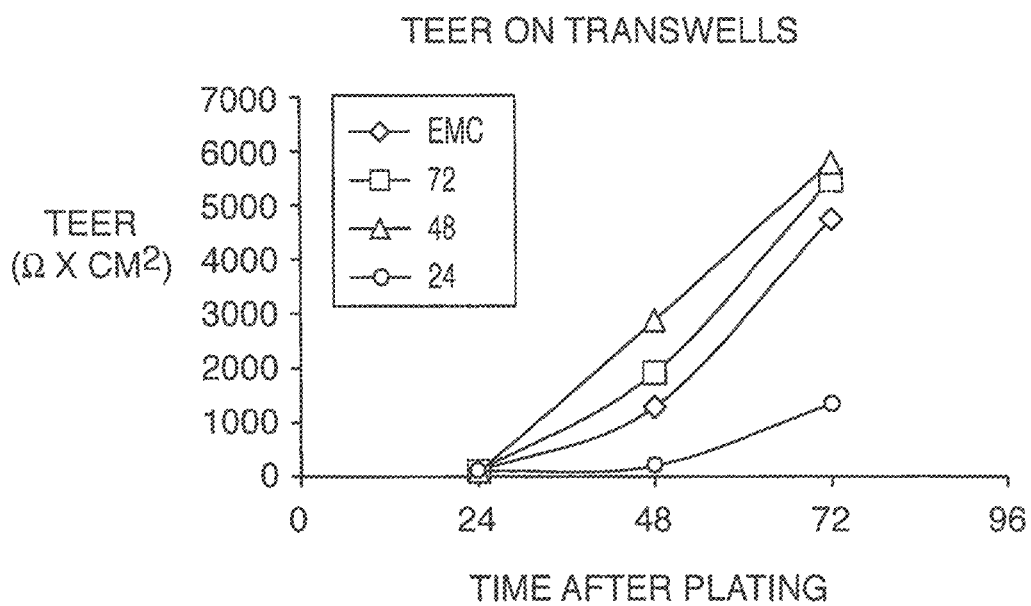
Figure 13A:
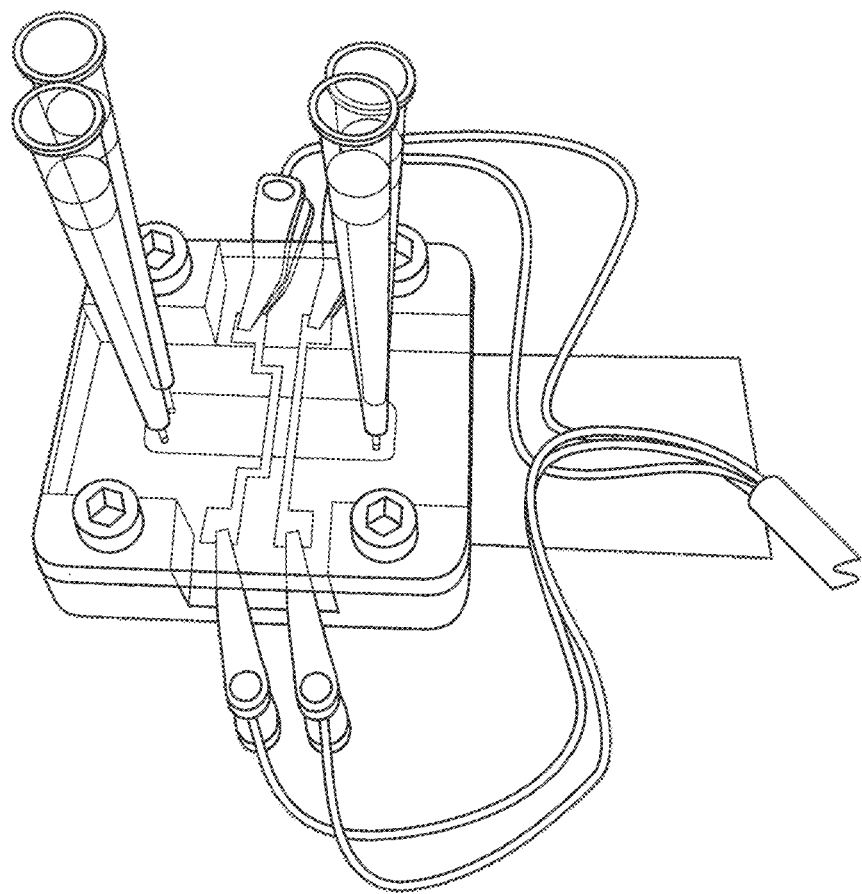
FIGS. 13A and B show how TEER measurements were made in one embodiment.
Figure 13B:
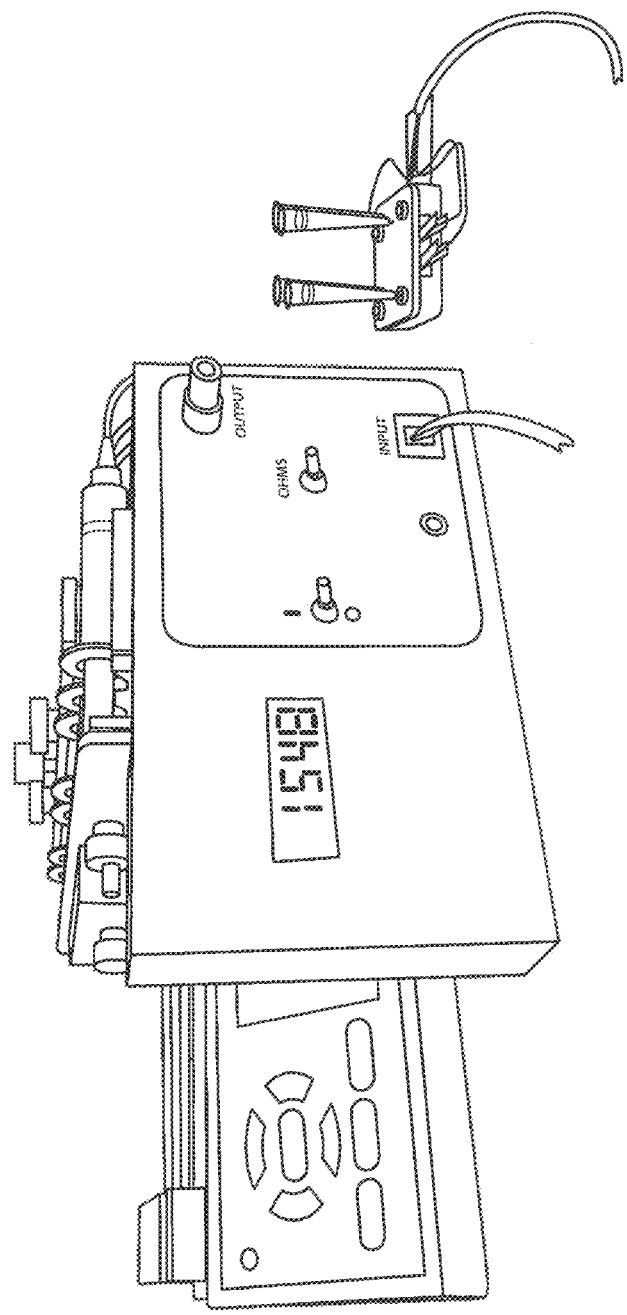
FIG. 13B shows the same connected chip to the right of a Epithelial Voltohmmeter.

TEER: FIG. 12A shows the results/readout from transepithelial electrical resistance (TEER) measurements on the microfluidic chip under flow, static, and control conditions. Cells were plated on tall channel PDMS chips equipped with incorporated gold electrodes on each channel (see FIG. 13A). Post seeding of BMECs, transendothelial electrical resistance was measured by connecting the electrodes to an EVOM2 voltohmmeter (see FIG. 13B). FIG. 12A displays preliminary data indicating the beneficial effect of flow in the BBB-on-chip, i.e. higher TEER in response to flow. In particular, at around the 40 hour time point, the TEER value observed for a BBB-on-chip under flow was significantly higher than a similar chip under static conditions, i.e. that the iPS brain microvascular endothelial cells (iBMECs) formed tighter cell-cell junctions or barrier function under flow conditions on a prototype TEER-Chip as compared to a chip maintained in static culture. The "damaged" chip was a failure due to the TEER-Chips being a prototype. FIG. 12B shows TEER results where the cells were cultured in transwells.

Figure 14A:
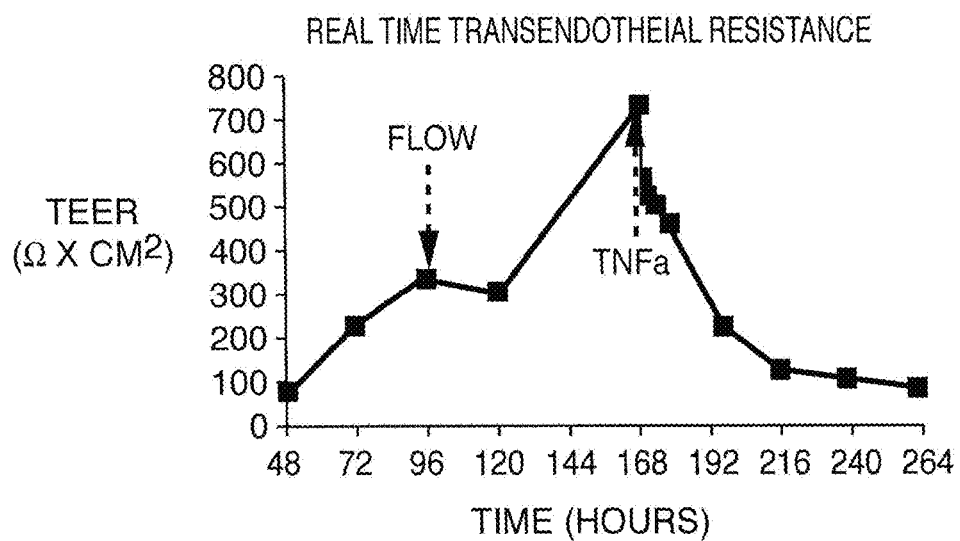
FIG. 14A was a follow-up experiment on another round of prototype TEER chips that showed iBMEC barrier function increasing in the presence of flow on a chip followed by a weakening of barrier function with the exposure of the chips to TNFa, a proinflammatory cytokine. Higher TEER values generally indicate a tighter barrier, which is typically desirable for a blood-brain barrier.

FIG. 14A was a follow-up experiment on another round of prototype TEER chips that showed iBMEC barrier function increasing in the presence of flow on a chip followed by a weakening of barrier function with the exposure of the chips to TNFa, a proinflammatory cytokine. Higher TEER values generally indicate a tighter barrier, which is typically desirable for a blood-brain barrier.

PATCH CLAMP: FIG. 18A-B shows electrophysiology recordings collected by patch-clamp from neurons in the microfluidic device ("BBB-on-Chip"). These measurements on-chip can be used to provide an indication of neuronal maturation, i.e. more precisely describe the maturity of a neuronal cell. Cells were cultured as described above in a specially designed "openable" chip (where the chips can be partially disassembled to expose directly cells on the semi-porous membrane) with a stiff PET membrane to aid in patch-clamp recording. PDMS was attempted, but was unsuccessful. PET membrane chips were opened at endpoint at 6 and 24 days in chip. Individual neurons seeded into the chip were directly accessed with a glass micropipette, and cell electrophysiology was recorded including capacitance, membrane resting voltage, spontaneous activity and induced activity. FIG. 18A-B is a whole cell patch recording of an induced action potential from a neuron cultured on the chip. An arrow (FIG. 18A) indicates single action potential. Current recordings (FIG. 18B, right) show negative sodium channel currents (Na$^+$) and positive potassium channel (IC) are necessary for normal neuron function and become more pronounced as a neuron matures.

Figure 19A:
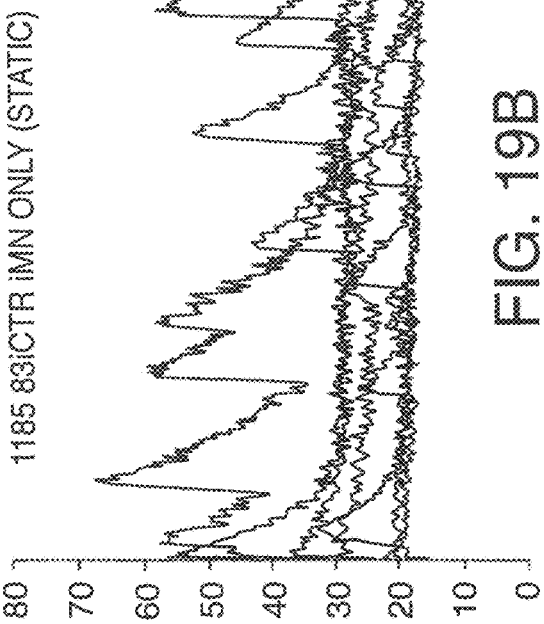
FIG. 19A-D show the results of calcium flux imaging in the neural channel. The photograph (FIG. 19A, top left) is a single fluorescent image from a movie of such images. The colored circles indicate the positions that correspond to the time traces in the 3 graphs. The traces (FIGS. 19B and C) show that it is possible to observe neuronal function in the microfluidic chips in real-time. The addition of tetrodotoxin (TTX), which is a potent blocker of voltage-gated calcium channels, ablates this activity (FIG. 19D, bottom right). Calcium imaging or imaging using voltage-sensitive dyes or proteins offer similar advantages to electrophysiological readouts but offers the advantage that no electrodes are necessary. Accordingly, some aspects of the present invention include methods of measuring the BBB-on-chip by imaging in the presence of calcium or voltage-sensitive dyes or proteins, to allow the potential recording and optional manipulation of neuronal or astrocyte excitations. These measurements can be used, for example, to provide an indication of neuronal maturation or as a readout of neuron health. In turn, neuronal maturation or health can be used as indicators of BBB-on-chip quality (for example, before starting an experiment) or as an experimental endpoint indicating, for example, that an agent as crossed the BBB, a disease condition has emerged, the BBB has been modified or compromised, or conversely, that the BBB or neural function or health have improved.
Figure 19B:
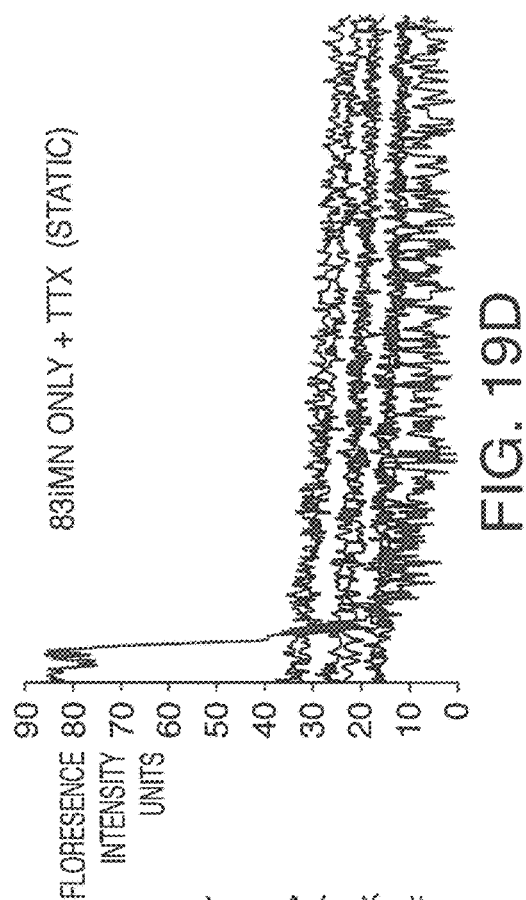
Figure 19C:
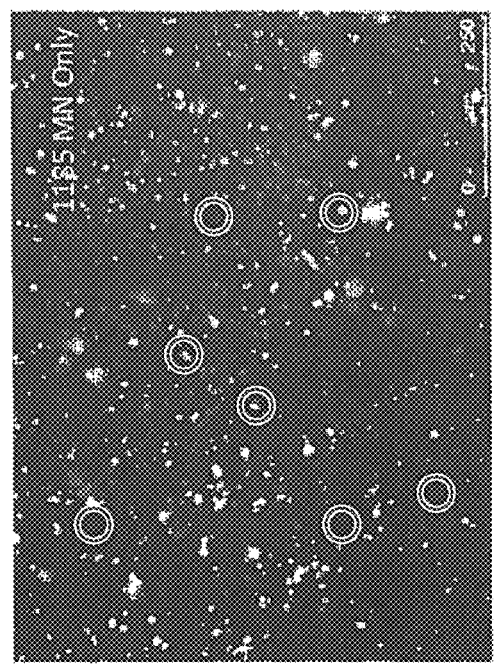
Figure 19D:
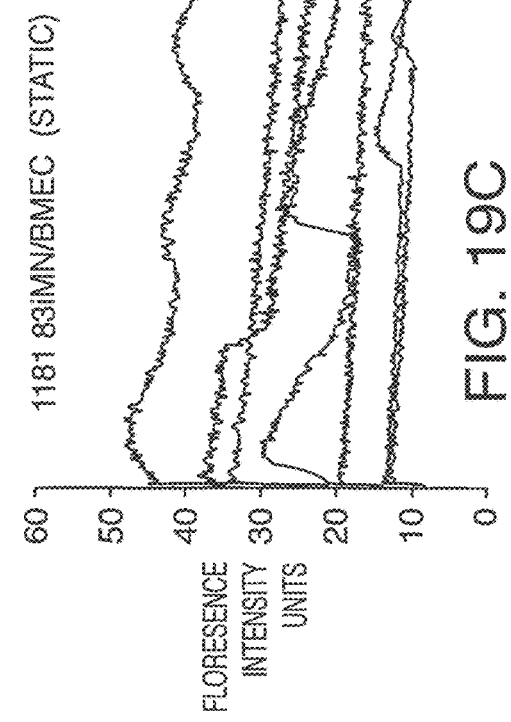
Figure 20:
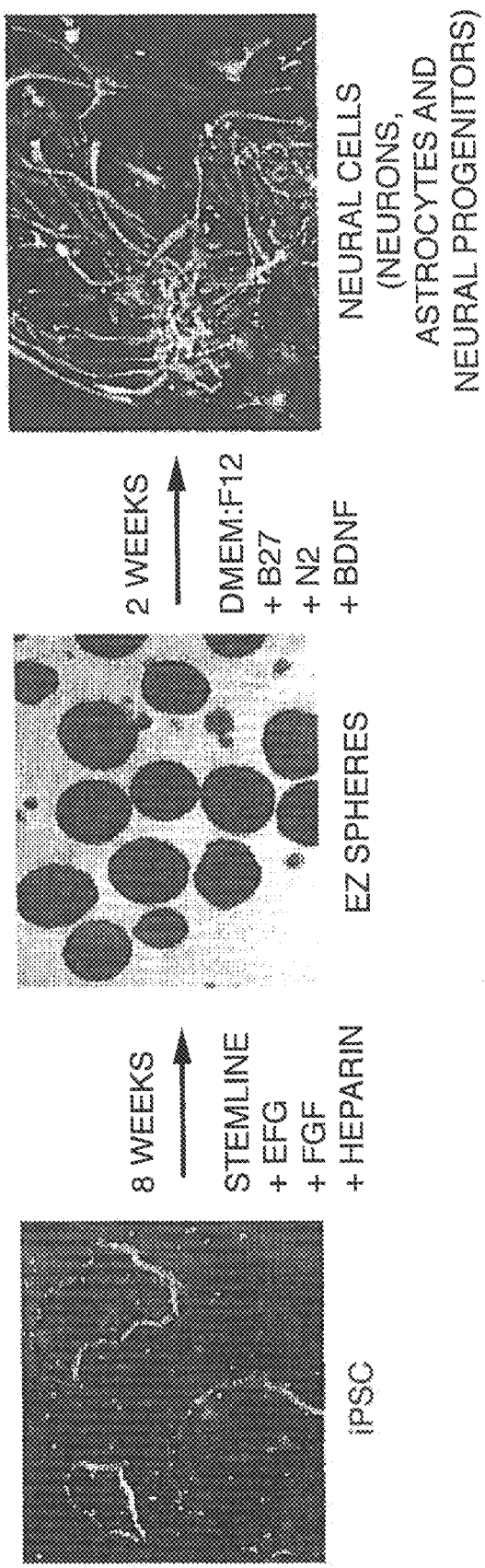
FIG. 20 shows both a protocol for generating, and staining results confirming the generation of, neural cells from neural progenitors. Such techniques allow one to make multipotent neural stem cells and motor neuron precursor directly from iPSC, allowing differentiation into many neural cell types (neurons, astrocytes, etc.).

CALCIUM FLUX: FIG. 19A-D show the results of calcium flux imaging in the neural channel. Using a florescent calcium influx-activated dye (Fluo-4), neurons seeded in chip were imaged using high resolution high frame-rate camera. Florescence intensity changes of up to hundreds of neurons were analyzed simultaneously by recording average pixel intensity over time (dF/F). These values were plotted with respect to time and are analyzed for waveform properties, which correlate spontaneous neural activity and neural network formation. This is accomplished through multi-step video post-processing and signal analysis (including video compression, signal cleanup, automatic or manual ROI detection, etc. which can be implemented from open-source MATLAB software packages). The photograph (FIG. 19A, top left) is a single fluorescent image from a movie of such images. The colored circles indicate the positions that correspond to the time traces in the 3 graphs. The traces show that it is possible to observe neuronal function in the microfluidic chips in real-time. In this case, it is shown that Ca2+ fluxes can be measured on chips to give a direct readout of neuronal activity. The addition of tetrodotoxin (TTX), which is a potent blocker of voltage-gated calcium channels, ablates this activity (FIG. 19D, bottom right). This type of experiment will be important when the neuronal activity is modulated by pharmacological stimulation.

ICC overlay data: By overlaying images taken after staining the cells, specific cell identification can be combined with original activity traces to determine specific activities of individual cell types in the chip. The overlay data (not shown) indicates that motor neurons are indeed more active in the chip. This can also be accomplished with cell type specific reporter lines.

Example 10

Brain microvascular endothelial cells (BMECs) constitute the blood-brain barrier (BBB) which forms a dynamic interface between the blood and the central nervous system (CNS) in vivo. This highly specialized interface restricts paracellular diffusion of fluids and solutes including chemicals, toxins and drugs from entering the brain. In this example, fluorescein sodium is used in a paracellular permeability assay of the BMECs seeded on a microfluidic device.

Figure 14B:
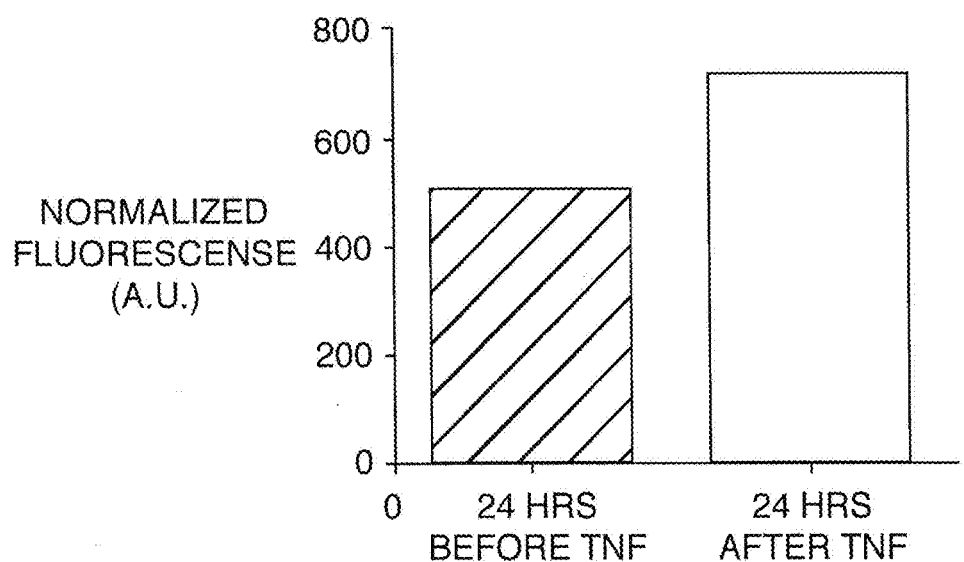
FIG. 14B also involves TNF alpha exposure, but the readout is membrane permeability as measured by Dextran-FITC.

Albumin or Dextran conjugated to a fluorescent probe (e.g., FITC or TRITC) are frequently used to monitor changes in leakage, and thus barrier function. In this case, Dextran-FITC, a green fluorescent molecule of 4 KDa, or sodium fluorescein (a 0.3 KDa molecule), was added to the bottom ("blood side") channel. Paracellular permeability was calculated by measuring the permeability of the fluorescent molecule on the Top ("brain side") channel. Low permeability is an indication for proper barrier functions. FIG. 14B involves TNF-alpha exposure, but the readout is membrane permeability as measured by Dextran-FITC. FIG. 14B confirms that TNFa exposure results in a decrease in barrier function and TEER by an increase in permeability through the semi-porous membrane by dextran-F1TC, a fluorescently labeled small molecule.

Figure 15:
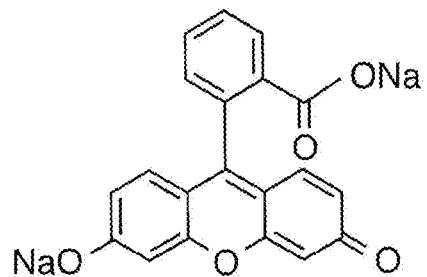
FIG. 15 shows permeability results for (and the structure of) fluorescein sodium. Some aspects of the present invention include ascertaining permeability for various additional agents (e.g. drugs, chemicals, hormones, blood components, biomarkers). Such methods can allow qualitative or quantitative estimation of the permeability of the in vitro blood-brain barrier to the one or more agents. Furthermore, according to some aspects of the present invention, the permeability of one agent is measured in response to a second agent, treatment or experimental condition (for example, measuring the effect of a medication on the blood-brain barrier permeability of another medication).
Figure 15:
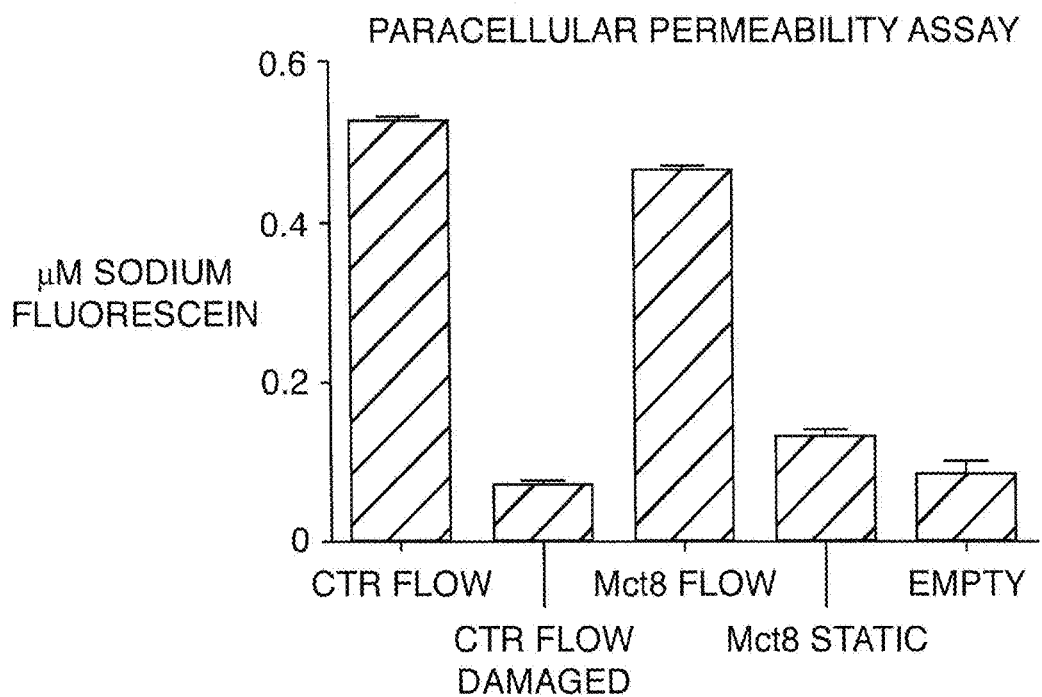

FIG. 15 shows the results for (and structure of) fluorescein sodium from a paracellular permeability assay. Chips were seeded with iPSC-derived BMECs taken from healthy controls (CTR) or MCT8-deficient patients, and the paracellular permeability was determined by monitoring Blood to brain permeability of the sodium fluorescein tracer as described above. Flow is clearly important.

In the present experiment, the agent used was fluorescein. In some aspects of the present invention, it is contemplated that similar testing will be done to ascertain permeability for various additional agents (e.g. drugs, chemicals, hormones, blood components, biomarkers). Such methods can allow qualitative or quantitative estimation of the permeability of the in vivo blood-brain barrier to the one or more agents. Furthermore, according to some aspects of the present invention, the permeability of one agent is measured in response to a second agent, treatment or experimental condition (for example, measuring the effect of a medication on the blood-brain barrier permeability of another medication). It is important to note that although we refer to permeability, we do not mean to exclude active transport, pumping or any other means for an agent to pass from one side of the barrier to the other (regardless of direction). The penetration of an agent through the barrier can be measured, for example, using mass spectroscopy, antibody-based methods (e.g. ELISAs, Western blots, bead-based assays), or optical methods (e.g. fluorescence signature, Raman spectroscopy, absorbance).

Example 11

Some embodiments include blood or blood components, optionally perfused through one or more fluidic channels within the device. The use of blood of blood components is desired as the blood or blood components can improve BBB-on-chip function, for example, by providing biochemical cues, or conversely hurt the BBB-on-chip, for example, because the blood may contain a harmful agent that may be under investigation. In some aspects, permeability assays include blood or blood components in order to provide a potentially more in vivo like result. In other aspects, individual-specific blood or blood components are used in order to potentially provide individualized BBB-related measures. This can include, for example, the measurement of the permeability of one or more agents or components from the blood or components, the effect of the blood or components on the permeability of one or more agents that may be added to the blood or another fluid included in the device, the effect of the blood or components on the health of the BBB-on-chip or any of its components (whether positive or negative), etc. This may include diagnostic uses, for example, to identify a disease, biomarker or infectious agent carried by the blood or blood components.

In this example, hormone transport across the BMECs was measured in the "BBB-on-chip" in healthy and diseased tissue by mass spectrometry. Thyroid hormone was added to the bottom channel and measured on the top channel. Thyroid hormones ($T_3$ and $T_4$) were detected using Liquid chromatography tandem-mass spectrometry (LC-MS/MS).

Figure 16A:
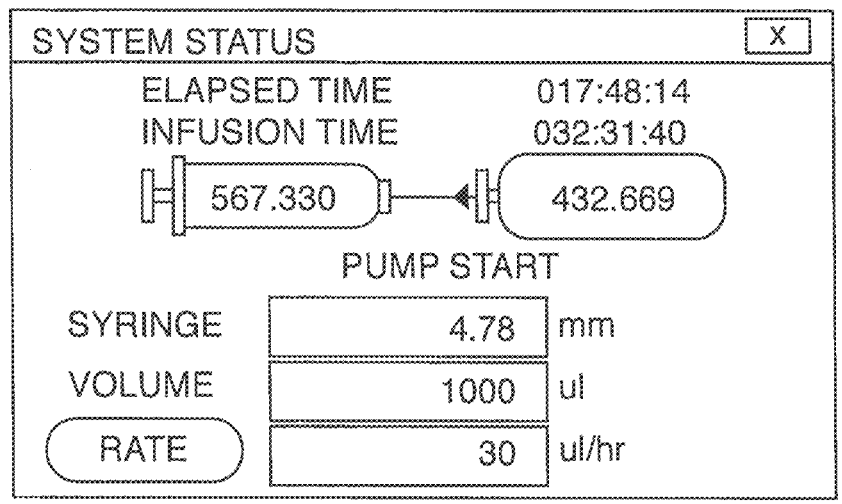
FIG. 16A shows the user interface and the conditions during the run of human blood across the blood brain barrier.
Figure 16B:
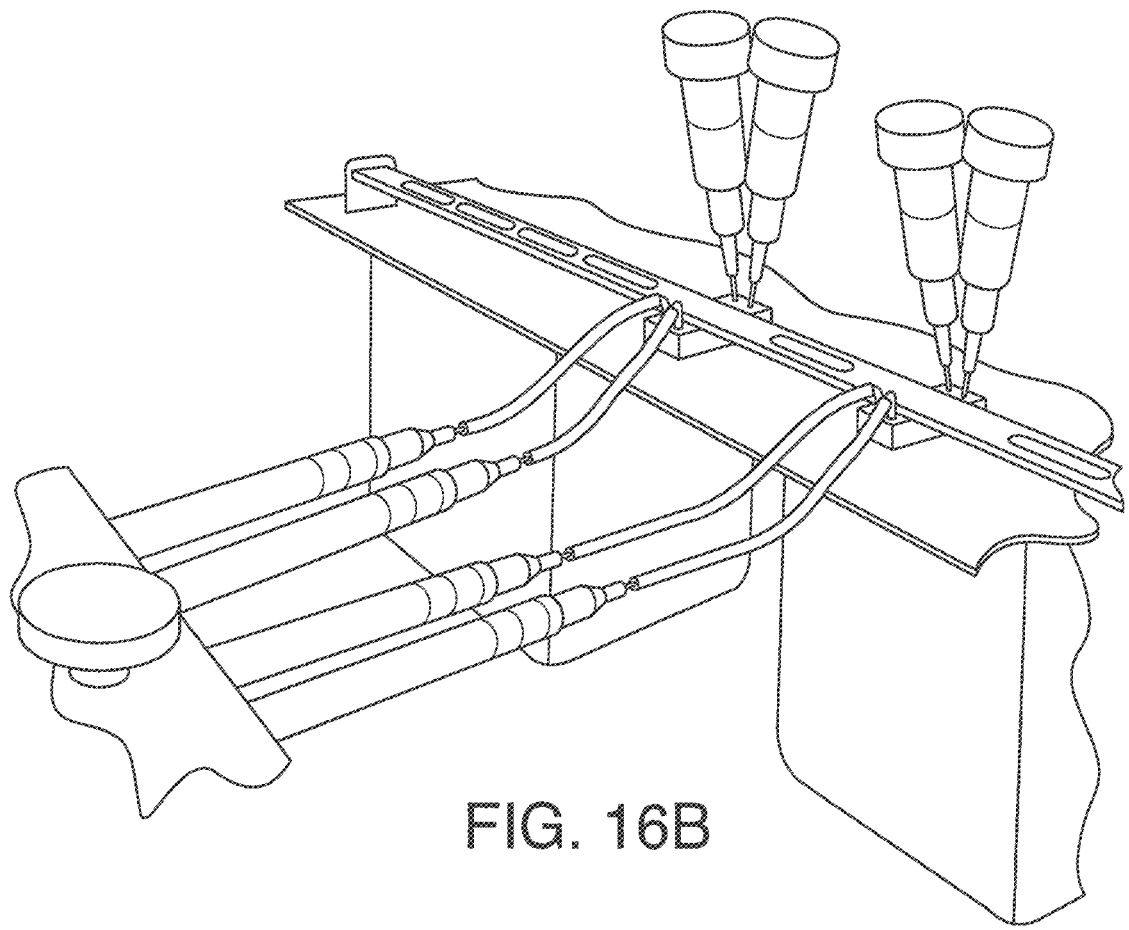
FIG. 16B shows the equipment setup for measuring the transport of solutes from human blood across the blood brain barrier (BBB), a barrier created in vitro in the microfluidic devices described herein using a layer of BMECs. As evidenced, some embodiments include blood or blood components, optionally perfused through one or more fluidic channels within the device. The use of blood of blood components is desired in some embodiments, as the blood or blood components can improve BBB-on-chip function, for example, by providing biochemical cues, or conversely hurt the BBB-on-chip, for example, because the blood may contain a harmful agent that may be under investigation. In some aspects, permeability assays include blood or blood components in order to provide a potentially more in vivo like result. In other aspects, individual-specific blood or blood components are used in order to potentially provide individualized BBB-related measures. This can include, for example, the measurement of the permeability of one or more agents or components from the blood or components, the effect of the blood or components on the permeability of one or more agents that may be added to the blood or another fluid included in the device, the effect of the blood or components on the health of the BBB-on-chip or any of its components (whether positive or negative), etc. This may include diagnostic uses, for example, to identify a disease, biomarker or infectious agent carried by the blood or blood components.

BMECs from a MCT8 background were used. FIG. 16A shows the user interface and the conditions during the run of human blood across the blood brain barrier. FIG. 16B shows the setup for measuring the transport of solutes from human blood across the blood brain barrier, a barrier created in vitro in the microfluidic devices describes herein using a layer of BMECs. FIG. 16B shows how human blood was perfused into the bottom channel of the tall chip. In this experiment thyroid hormones were measured by LC-MS/MS as described above. This setup will also be used to test the filtration of proteins across the BBB.

Figure 17A:
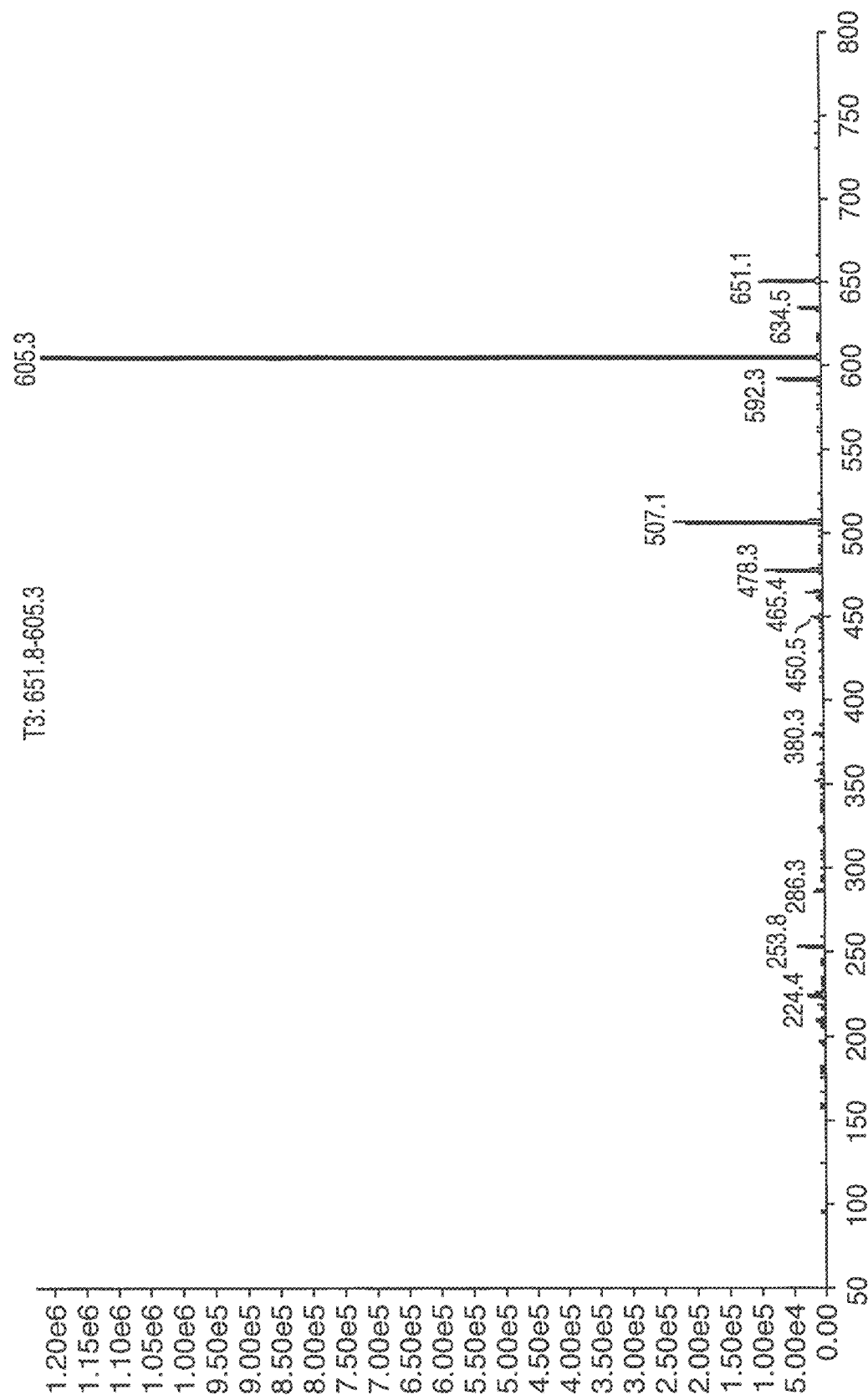
FIG. 17A-C shows the measurement of thyroid hormone transport by mass spectrometry (FIG. 17A) using the setup shown in FIG. 16A-B, along with the graphed results (FIG. 17B).
Figure 17B:
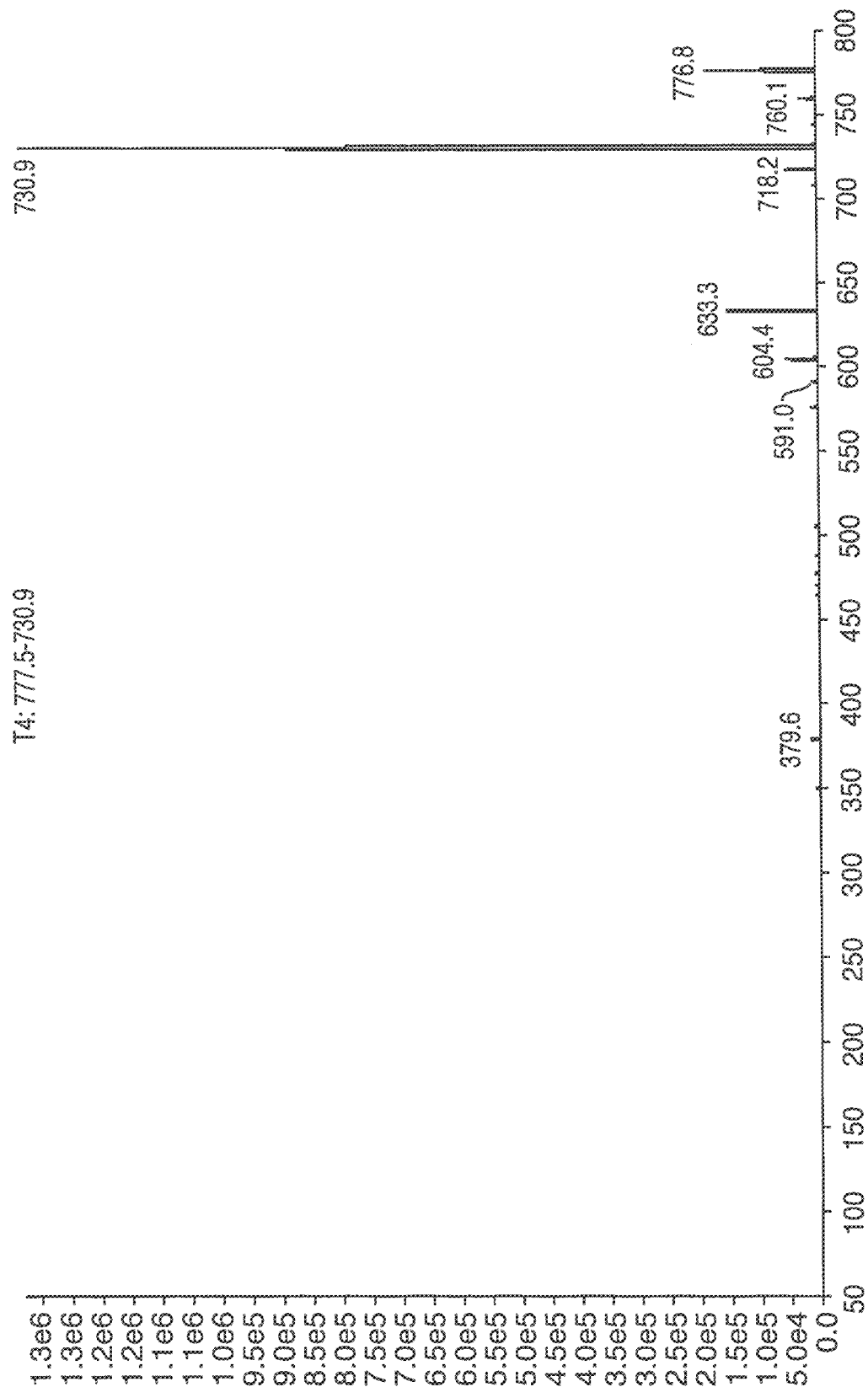
Figure 17C:
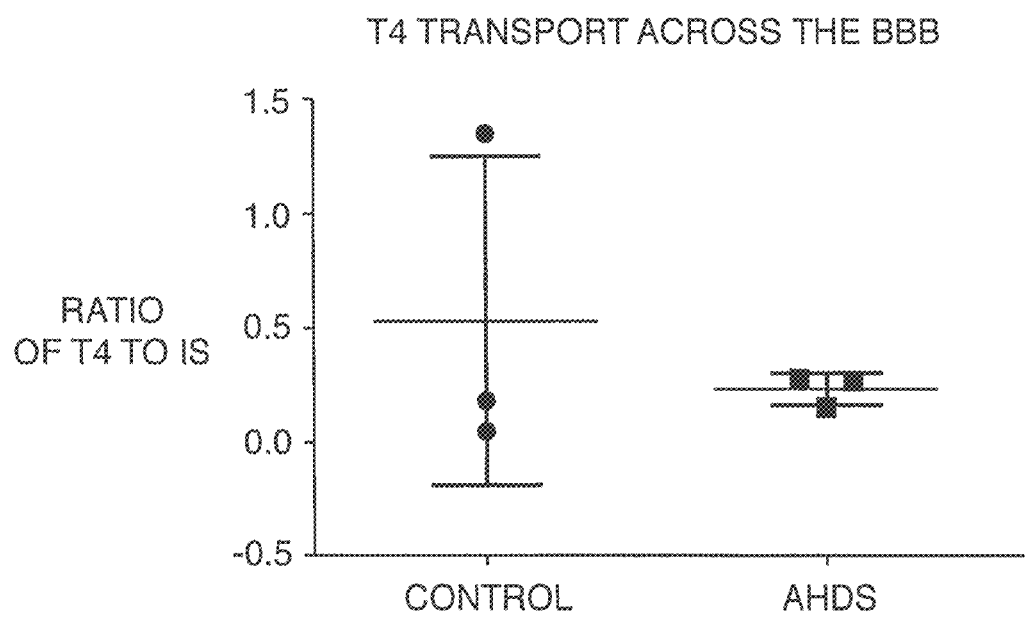

FIG. 17A-C shows the measurement of thyroid hormone transport by mass spectrometry (FIG. 17A) using the setup shown in FIG. 16B, along with the graphed results (FIG. 17B). After flowing patient blood through the microfluidic chips into the channel under the BMECs, it was possible to measure the transport of compounds from the blood into the neural compartment, i.e. through the BMEC barrier. In this case, the experiment included a control set of BBB-on-chips comprising iPS-derived cells originating from a non-diseased individual, and a second set of BBB-on-chips comprising iPS-derived cells originating from a patient diagnosed with Allan-Herndon-Dudley syndrome (AHDS). Briefly, iBMECs were generated from a patient with an inactivating genetic mutation in the MCT8 thyroid hormone transporter. This mutation leads to a defect in T3/T4 transport across the BBB and defects in neural development in patients. The mass-spectrometry data in FIG. 17A is an initial experiment to confirm that the MCT8 transporter defect can be recapitulated on an Organ-Chip.

Example 12

In this example, the disease model was further evaluated. Samples were prepared by taking 100 ul of each sample of T3 and mixing it with the equivalent sample of T4. This was done for each sample and also for the calibration curve. Proteins and salts were precipitated from the solution; the samples were dried and resuspended in the same volume. The calibration curve permitted the calculation of the concentrations (in mM) for both T3 and T4.

For the T3/T4 experiments, the following 4 conditions were tested in the microfluidic chip:
1. 1 nM T3 in normal media in the bottom channel and media without T3 on top channel. Both sides were running at a 30 ul/hr flow rate.
2. 100 nM T3 and T4 in normal media in the bottom channel and media without T3 on top channel. Again, both sides were running at a 30 ul/hr flow rate.
3. Human plasma on bottom channel at 90 ul/hr and media without T3 on top channel kept static for 1 hour.
4. Human plasma on bottom channel at 90 ul/hr and media without T3 on top channel kept static for 1 hour.

For each experiment, Dextran-FITC was used in the bottom channel to correct for paracellular diffusion.

Figure 21:
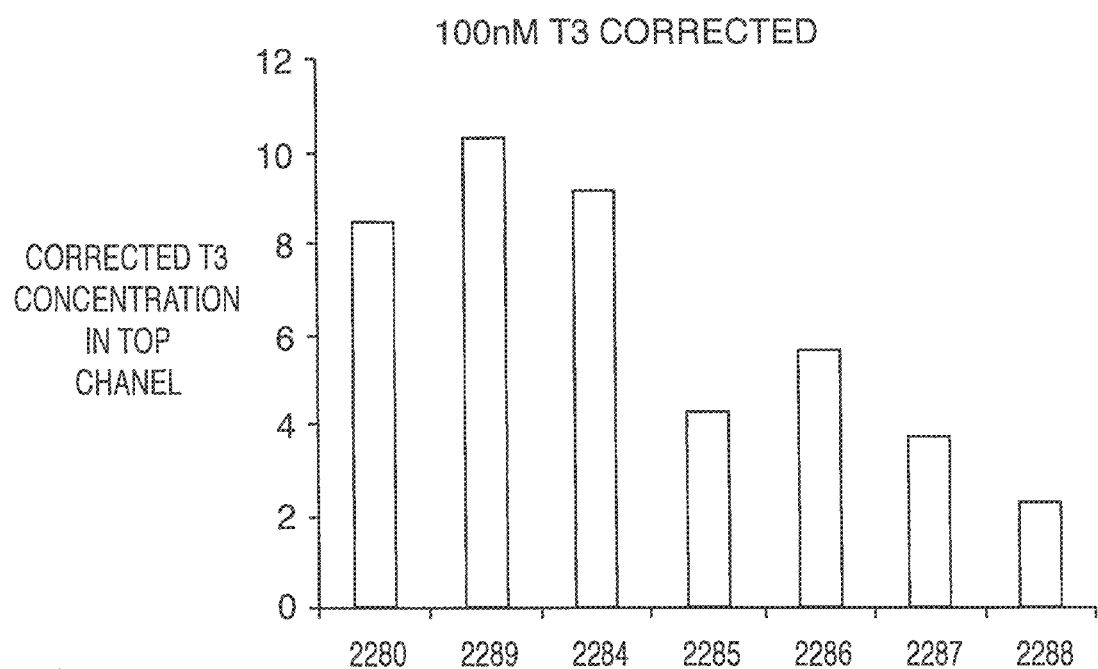
FIG. 21 shows the corrected T3 concentration in the top channel of seven different chips, i.e. chips populated with normal cells (2280, 2289 and 2284) as compared to chips populated with cells from an MCT8 cell line or patient (2285-2288).
Figure 23A:
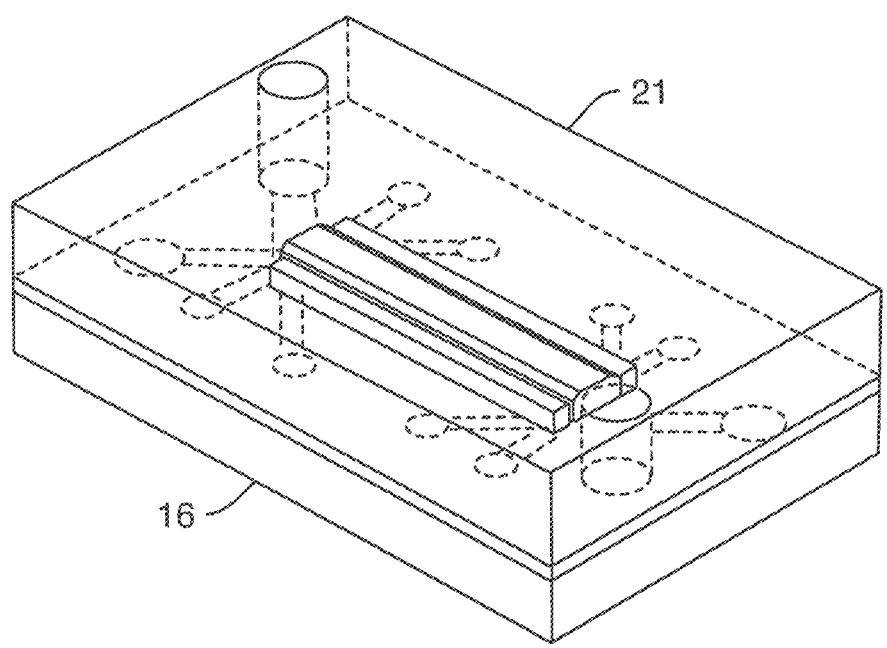
FIG. 23A-B shows a schematic of an illustrative microfluidic device or "organ-on-chip" (16) device. The assembled device is schematically shown in FIG. 23A with the top surface (21) indicated.
Figure 23B:
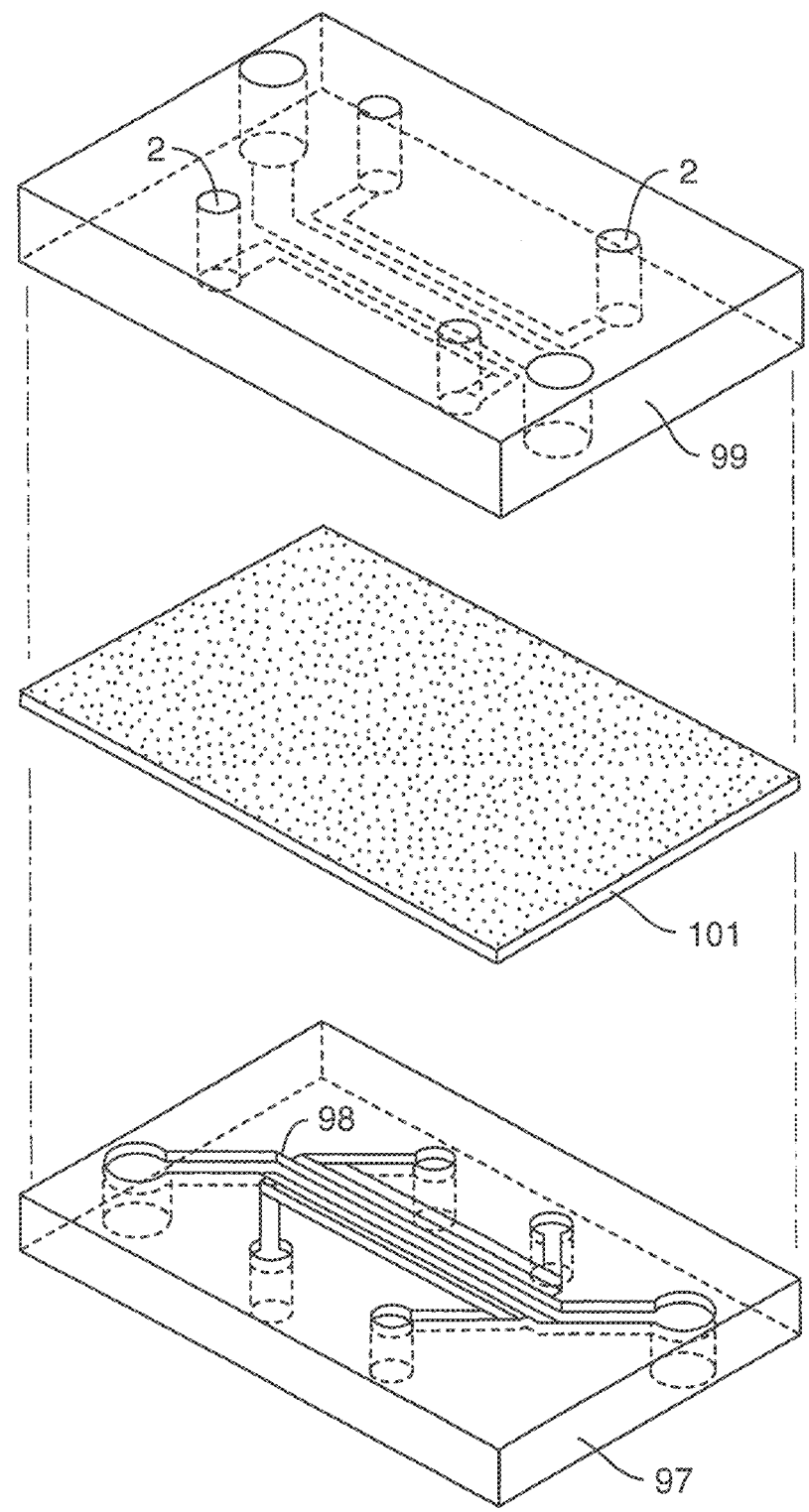

From the above-mentioned 4 conditions, only 100 nM was significantly above detection and these worked well as shown in FIG. 21. Chips 2280, 2289, and 2284 are populated with cells from a single control line. Chips 2285 and 2286 are populated with cells from the isogenic mutated MCT8 line. Chips 2287 and 2288 are populated with cells from a mutated MCT8 patient. FIG. 21 is a bar graph showing the corrected T3 concentration in the top channel of each chip. Clearly, there is reduced T3 transport in mutated MCT8 lines as compared to normal, demonstrating one aspect of disease modeling using the blood-brain barrier, organ-on-chip device.

Example 13

In one embodiment, the present invention contemplates contact of neurons and brain related vascular cells, and more preferably, direct contact of iMNs and iBMECs on the microfluidic chip to enhance neuronal physiology as measured by electrophysiology and transcriptomics. It has been found that the chip accelerates diMN electrophysiological maturation.

In this experiment, diMNs seeded into the chip were recorded after 12 days after seeding. FIG. 24A-B provides a whole cell patch clamp recording of a non-invoked spontaneously active neuron showing highly complex and repetitive bursts of neuronal activity indicative of neuronal networks being established in the chip.

When induced to fire by injecting current into the neuron at day 6 in chip, more resolved action potentials are observed (FIG. 25B) compared to traditional culture (FIG. 25A).

Figure 26A:
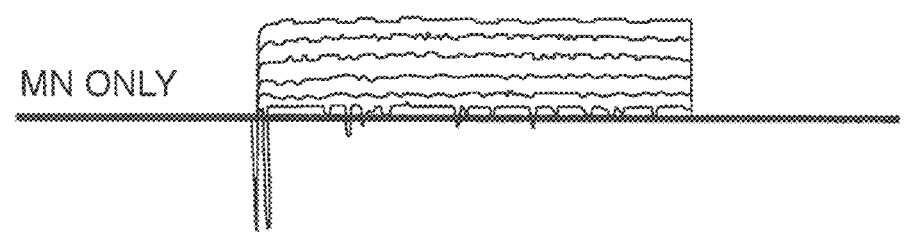
FIG. 26A-B shows print outs of electrophysiological data from neurons cultured alone (FIG. 26A, top panel) and co-cultured with BMECs (FIG. 26B, bottom panel) in a microfluidic device or chip, showing that neural tissue have more mature electrophysiological properties in the chip when in co-culture with BMECs.
Figure 26B:
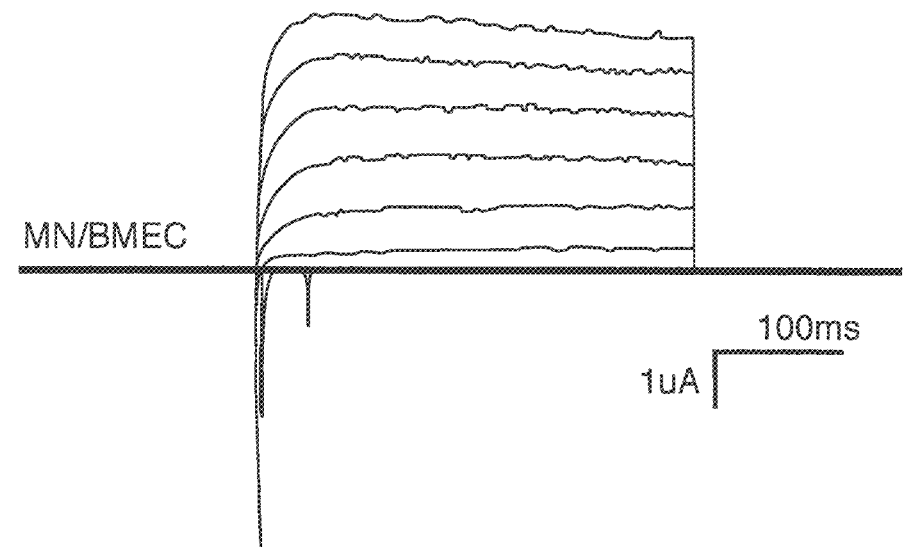
Figure 27A:
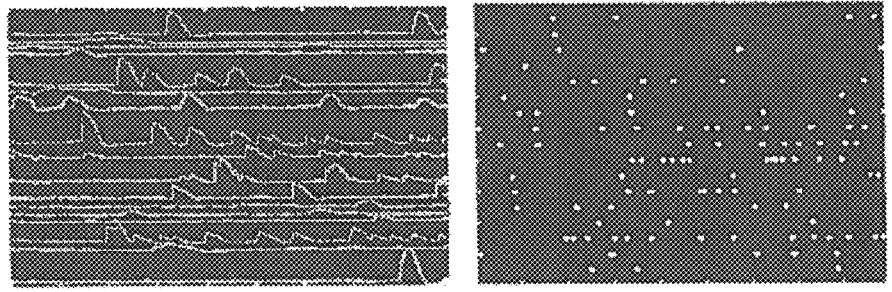
FIG. 27A-D provides neural calcium measurement readouts comparing neurons (MN) co-cultured with BMECs (FIG. 27D, bottom panel), cultured alone (FIG. 27C, first panel up from the bottom panel), cultured in endothelial cell conditioned medium or ECCM in a (96-well) static culture (FIG. 27B, second panel up from the bottom panel), along with an unconditioned media (96-well) static control (FIG. 27A, top panel). Each neuron's activity is simultaneously tracked and analyzed (calcium influx is an indirect measure for neuronal activity that can be observed live in the chip). The results show that co-culture increases diMN neural calcium transient activity, i.e. a significant increase in transient frequency is observed upon contact of MNs with iBMECs.
Figure 27B:
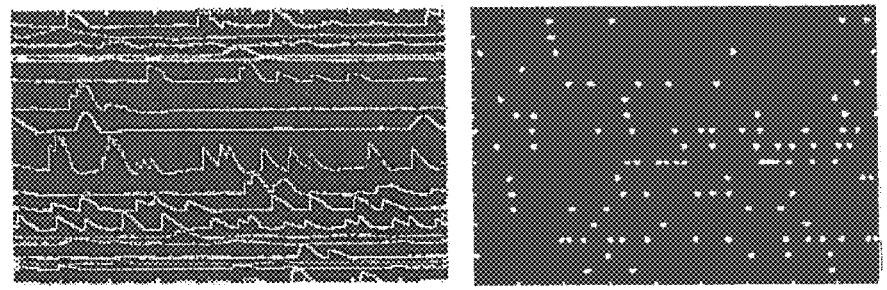
Figure 27C:
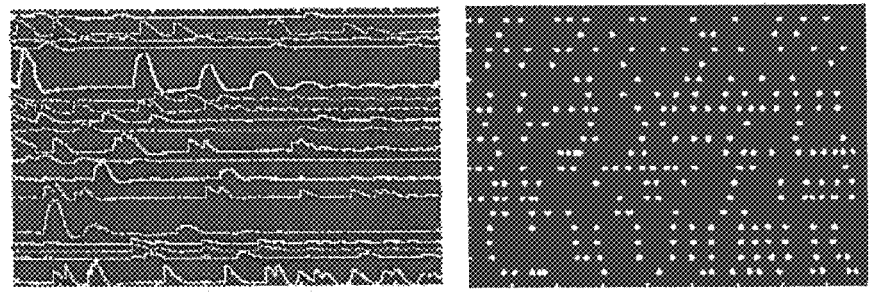
Figure 27D:
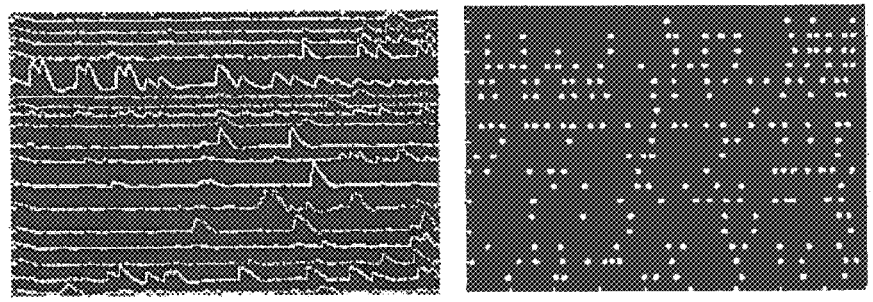

Neurons that are co-cultured with BMECs in chip (MN/BMEC) show more pronounced currents (FIG. 26B) than MNs cultured alone (FIG. 26A) on chip (MN Only) as depicted by current traces recorded as the neuron is induced to fire an action potential. These observed electrophyisiological properties are well established in the field as indicating neurons are more mature at this time point.

Example 14

In a controlled study, calcium influx live cell imaging was performed on diMNs that had been cultured in the chip (MN Chip) and in co-culture with BMECs (MN/BMEC). Neuron calcium influx was recorded as described previously, and plotted with respect to time (FIG. 27A-D, right panels). Calcium influx events or peaks correspond to neural activity and were counted by both automated software and blinded human technician. Each event was assigned a time-stamped value and depicted for each tracked neuron with respect to time.

Figure 28:
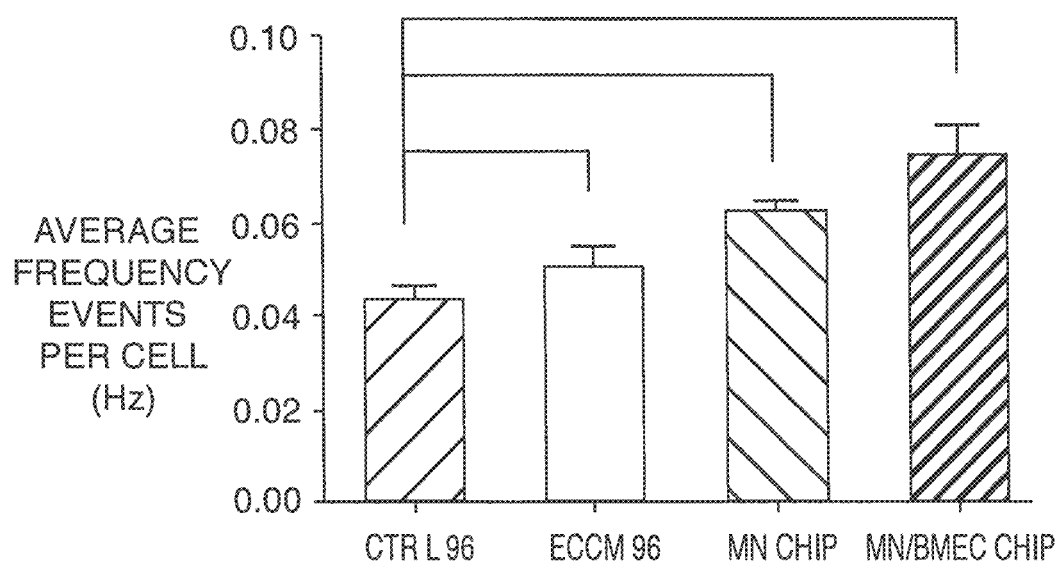
FIG. 28 is a bar graph of neural calcium measurements (average frequency events per cell) comparing neurons (MN) co-cultured with BMECs (far right), cultured alone (next bar to the left), cultured in endothelial cell conditioned medium or ECCM in a static culture (next bar to the left), along with an unconditioned media static control (far left). The results show that co-culture increases diMN neural calcium transient activity, i.e. a significant increase in transient frequency is observed upon contact of MNs with iBMECs.

FIG. 28 is a bar graph showing that the frequency of recorded neurons on the chip is significantly increased in both chip conditions compared to traditional 96 well culture control (CTRL 96). This increase was not observed in 96 well cultures that had been treated with media preconditioned with BMECs (ECCM 96) indicating the increase in the neurons ability to flux was achieved exclusively in the chip. This effect was further increased with the addition of BMECs to the chip in co-culture. Increased frequency is known to occur in vivo as MNs mature and indicate neurons mature faster in the chip.

Example 15

Figure 29A:
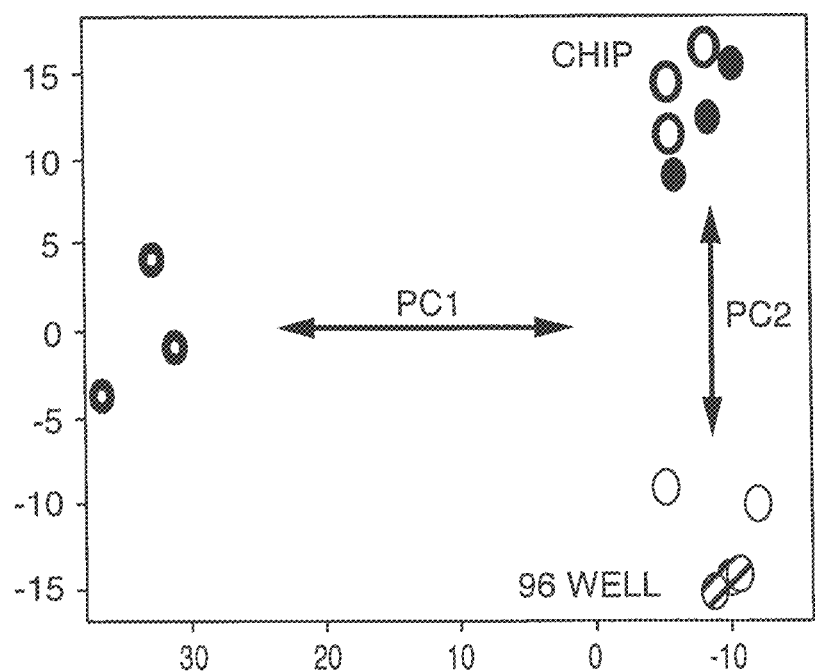
FIG. 29A-B shows the results of a transcriptomic study of iMNs in a microfluidic chip. Neurons were either cultured alone (FIG. 29A, top box) on the chip or in a co-culture with BMECs (FIG. 29B, bottom box), and this was compared with a 96-well static culture. The MNs were sorted on a FACS and RNA was sequenced (i.e. gene expression was detected). RNA-Seq from FACS sorted MNs show that neural development gene pathways (PC1) are upregulated in chip. Vascular interaction genes (PC3) are recreated in co-culture with iBMECs. In addition, there are chip induced genes (PC2), i.e. gene activity induced in the cells simply from being cultured on the chip.
Figure 29B:
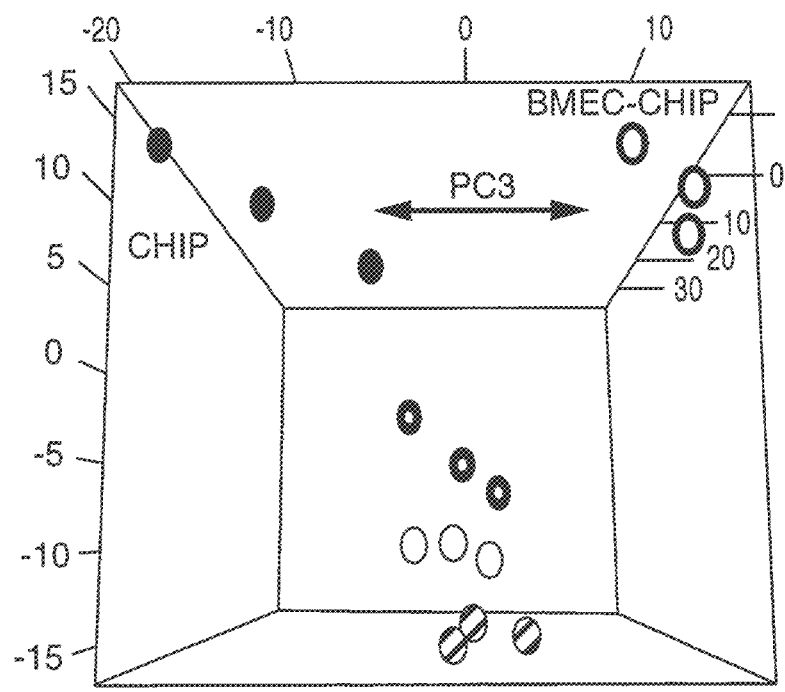

In this experiment, diMNs were stably transfected with a nuclear-tagged GFP reporter transgene and seeded on the top channel. NON-GFP BMECs were seeded into the bottom channel. Chips were allowed to mature either in this configuration, or non-BMEC controls (both diMN only on chip and diMN in a standard 96 well plate). The cells were FACS sorted to purify the diMN cultures away from the NON-GFP BMECs after 6 days on the chip. These purified cells were mRNA sequenced in all conditions, and a non-biased principle component analysis (PCA) was conducted on all samples. The first principle components separated the conditions by different genes expressed. PC1 separates all cultures from a progenitor pool (black) PC2 genes separated 96-well culture from diMNs in chip, and PC3 separated genes that were exclusively expressed in co-culture with BMECs (FIG. 29A-B).

Figure 30:
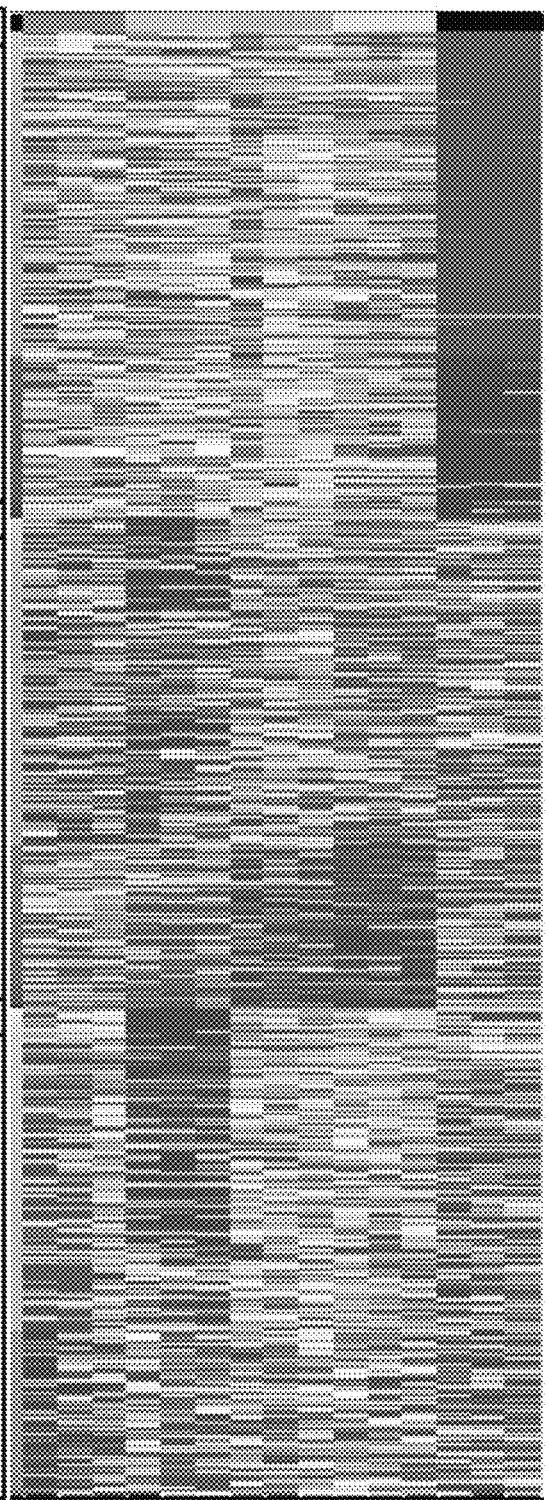
FIG. 30 shows the detailed results from which FIG. 29A-B was prepared, showing the names of various neural development genes (PC1), chip induced genes (PC2) and vascular interaction genes (PC3). The colored bars on the right in FIG. 30 represent the expression of each gene (row) in each of the 5 conditions (columns). Column order is MN Only, BMEC/MN, 96-well control, 96 well ECCM, MN progenitor. Red=high and blue=low. These vascular gene pathways have not been shown to be induced in any other culture system and may be inducing the observed increase in maturity and activity.
Figure 31:
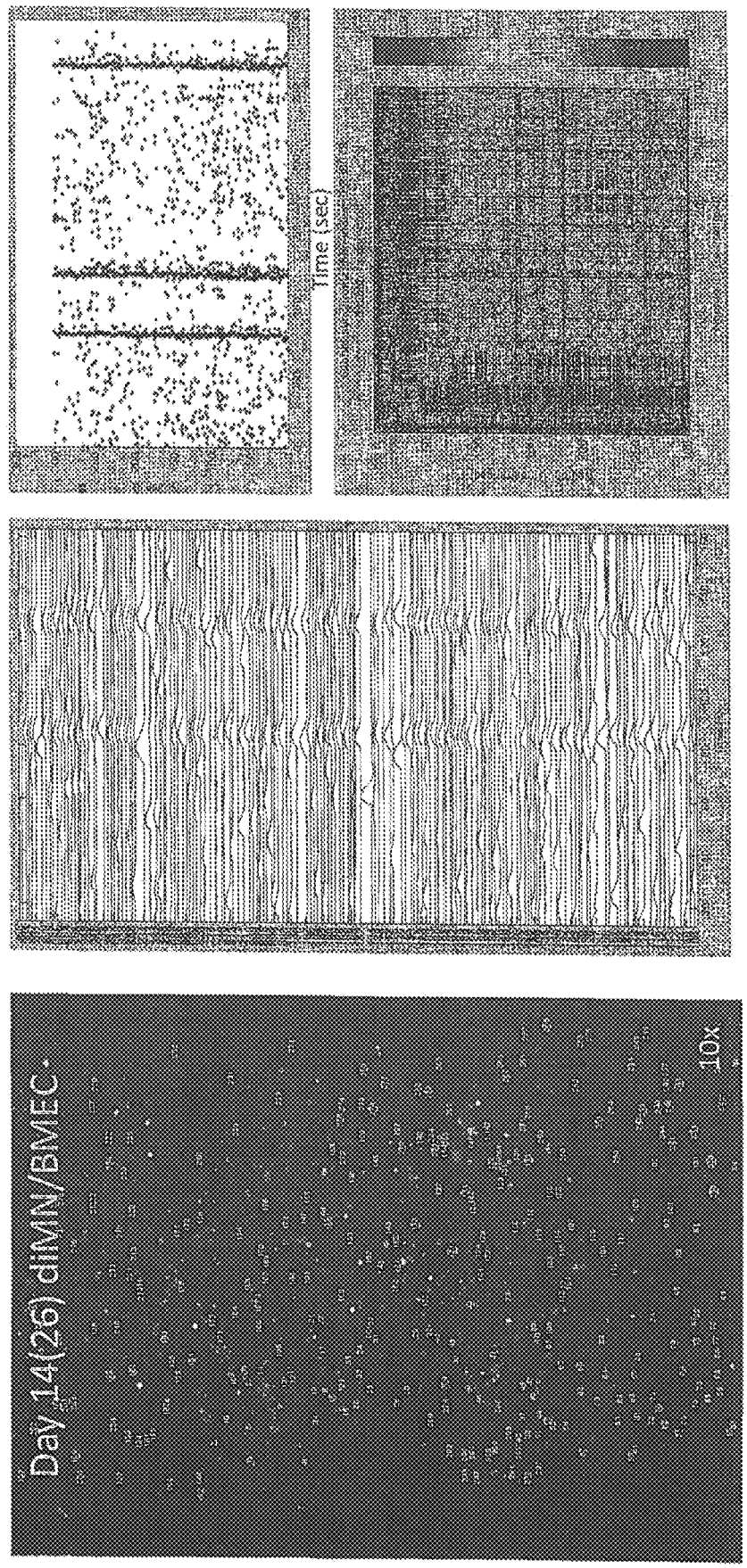
FIG. 31 shows, at 26 days, periodic spontaneous bursts of calcium transient activity that involves 30% of all active cells.

The top 200 highly expressed genes and bottom 100 low expressed genes from each PC were entered into the non-biased gene ontology platform DAVID. The resulting pathways included increased neural differentiation in the chip-specific PC2 gene set (FIG. 30, middle list). Vascular interaction gene pathways were found in the co-culture chips indicating that known in vivo gene pathways between the vascular system and neurons were recapitulated in the chip device. The colored bars on the right in FIG. 30 represent the expression of each gene (row) in each of the 5 conditions (columns). Column order is MN Only, BMEC/MN, 96-well control, 96 well ECCM, MN progenitor. Red=high and blue=low. These vascular gene pathways have not been shown to be induced in any other culture system and may be inducing the observed increase in maturity and activity.

Example 16

Brain Blood Vessel On-Chip Further Comprising Pericytes and Astrocytes.

FIG. 40A-B Exemplary schematic illustrations of a brain blood vessel in vivo and a microfluidic chip in vitro. FIG. 40A shows a schematic illustration of the histology of a cross section of a brain blood vessel in vivo depicting a blood vessel lumen formed by and surrounded by endothelial cells (EC), a vascular basement membrane separating ECs from pericytes (PC), which in turn are overlain with astrocytes. Kim, et. al., Journal of Cerebral Blood Flow and Metabolism. 2006. FIG. 40B shows one embodiment of a chip in vitro: 1. Upper channel, where the arrow depicts directional fluid flow. 2. Lower channel, where arrow depicts directional fluid flow. 3. Cell layer in upper channel. 4. Enodothelial cell layer in lower channel. 5. Porous Membrane. 6. Optional vacuum chambers for providing membrane stretch.

FIG. 41A-D Shows one embodiment of a chip in vitro as a blood brain barrier (BBB) on-chip demonstrating exemplary micrographs of immunofluorescently labeled cells in neuronal and vascular channels. FIG. 41A shows an exemplary overview (looking up through the lower channel (dark-purple staining of cells) into the upper channel (light-green staining of cells)) demonstrating cell coverage of both channels along with cell morphology. FIG. 41B shows an exemplary micrograph of immunofluorescently labeled cell markers in an enlarged view from FIG. 41A where the two channels begin overlapping. The cells on the upper right in the upper channel are labeled light-green for a GFAP marker. The cells on the upper left in the lower channel are stained for a Phalloidin marker (dark-purple) for cells restricted to the vascular channel. FIG. 41C shows an exemplary micrograph of an immunofluorescently labeled cell marker showing ZO-1 tight junctions (outlines) of endothelial cells in the vascular channel. Nuclei are stained with DAPI (blue). FIG. 41D shows an exemplary micrograph of an immunofluorescently labeled cell marker showing light-green for a GFAP marker in the neuronal channel, as an enlarged view from FIG. 41A. Nuclei are stained with DAPI (blue).

FIG. 42A-B Shows one embodiment of a chip in vitro as a blood brain barrier (BBB) on-chip demonstrating cell morphology of exemplary endothelial cells in the Vascular Compartment (lower channel). FIG. 42A schematic illustration of one embodiment of an On-Chip System showing neuronal cells in a neural compartment (upper channel) and cells lining a vasculature forming a simulated blood vessel in the lower channel as one embodiment for a chip as shown in FIG. 42B. FIG. 42B shows a micrograph demonstrating a cross section of one embodiment of a blood brain barrier on-chip as a 3D-Reconstruction of a Confocal Micrograph Image of fluorescently labeled cells, i.e. neuronal progenitors in the upper channel and HBMECs in the lower channel. As shown in the insert, endothelial cell markers (left to right) show immunofluorescent staining of Glut-1, PECAM-1, Occludin-5, and ZO-1.

FIG. 43A-B Shows one embodiment of a chip in vitro as a blood brain barrier (BBB) on-chip demonstrating cell morphology of exemplary pericytes and astrocytes as part of a neural compartment (upper channel). FIG. 43A shows exemplary micrographs of fluorescently labeled cells using markers for demonstrating exemplary pericytes (upper micrograph) labeled for alpha-SMA (green) and astrocytes (lower micrograph) labeled for GFAP (red) on-chips. FIG. 43B shows an exemplary micrograph of a lower power confocal micrograph image of fluorescently labeled cells as in FIG. 43A. Nuclei are stained with DAPI (blue). As shown in the insert, these labeled pericytes and astrocytes are an example of cells illustrated schematically in the neuronal compartment (upper channel) above a vascular channel in one embodiment of a blood brain barrier (BBB) on-chip.

FIG. 44A-C Exemplary micrographs of differentiating iPSC-derived endothelial cells on-chip and an exemplary chart showing that on-chip iPSC-derived endothelial cells form a tighter cell layer simulating a blood brain endothelial barrier. FIG. 44A An exemplary timeline for providing iPSC-derived endothelial cells on-chip. Day 0: exemplary morphology of an iPSC colony stained with GFP showing nuclei (blue). After expansion of iPSc colonies, Day 8-12 Start HBMECs Differentiation. Day 18-22 HBMECs selection for providing HBMECs. FIG. 44B shows a phase contrast micrograph of Human Brain Microvascular Endothelial Cells (HBMECs). FIG. 44C iPS-derived HBMECs (right blue column) demonstrates higher and more physiologically-relevant TEER values as compared to a brain endothelial cell-line (left grey column). $\Omega.cm^2$ vs. Average TEER ($ohm.cm^2$).

FIG. 45 Shows one embodiment of a chip in vitro as a blood brain barrier (BBB) on-chip demonstrating cells expressing typical markers of Astrocytes, Pericytes and HMBECs after 5 days on-chip. Middle fluorescent confocal micrograph shows a cross section of cells on a chip. Upper fluorescent confocal micrograph at a higher magnification shows cell morphology of exemplary pericytes (αSMA-red) and astrocytes (GFAP-green) as part of a neural compartment (upper neuronal channel). Nuclei are stained with DAPI (blue). Lower fluorescent confocal micrograph at a higher magnification shows cell morphology of exemplary endothelial cells (iHBMEC (Glut1-red) as part of a vascular compartment (lower vascular channel). Nuclei are stained with DAPI (blue).

FIG. 46A-B A Barrier Function test using Fluorescent Dextran (3 kDa) demonstrates exemplary low diffusion of Dextran indicating intact barrier function of the vasculature in one embodiment of a blood brain barrier (BBB) on-chip. FIG. 46A An exemplary chart showing Dextran Diffusion as % Dextran (fluorescence). The majority of dextrin is in the vascular channel. FIG. 46B An exemplary Barrier Function Schematic illustrating the movement of dextrin from the Vascular Channel to the Neuronal Channel.

FIG. 47A-F A Barrier Function test demonstrates exemplary low diffusion of human IgG and albumin but not transferrin indicating intact barrier function of the vasculature in one embodiment of a blood brain barrier (BBB) on-chip. FIG. 47A-B Low diffusion of IgG indicates robust and physiological barrier integrity at the vascular-neuronal interface. FIG. 47C-D Low diffusion of Albumin indicates robust and physiological barrier integrity at the vascular-neuronal interface. FIG. 47E-F High levels of transferrin in the neuronal channel indicates presence of transferrin transporters functionally active on iPS-derived brain endothelial cells. FIGS. 47A, C and E Exemplary charts showing human IgG measured by ELISA, human albumin diffusion as albumin concentration ug/ml, and human transferrn (ELISA), respectively. The majority of human IgG and albumin is in the vascular channel. FIGS. 47B, D and F Illustrate exemplary barrier function schematics illustrating the movement of human IgG, albumin or transferrin, respectively, from the Vascular Channel to the Neuronal Channel.

The invention claimed is:

1. A method of culturing cells, comprising:
    a) providing:
        i) a dual microchannel microfluidic device comprising a first microchannel and a second microchannel separated by a membrane;
        ii) human ventral spinal neuron progenitor cells seeded within said first channel; and
        iii) brain microvascular endothelial cells seeded within said second microchannel;
    b) differentiating at least a portion of said human ventral spinal neuron progenitor cells with a flowing culture media in said first microchannel; and
    c) culturing said human ventral spinal neuron progenitor cells to express at least one marker of a spinal motor neuron.

2. The method of claim 1, wherein said at least one marker is selected from the group consisting of SMI32, nuclear marker islet 1 (ISL1), Beta 3 tubulin (TUBB3), NIOC6.1, neurofilament marker microtubule-associated protein 2 (MAP2), and synaptic marker synaptophysin (SYNP).

3. The method of claim 1, wherein said first microchannel is fluidically coupled to a top chamber comprising an open region.

4. The method of claim 1, wherein said ventral spinal neuron progenitor cells seeded within said first microchannel are disposed within a gel or gel-precursor.

5. The method of claim 1, wherein said ventral spinal neuron progenitor cells are seeded on top of a gel present within a portion of said first microchannel.

6. The method of claim 1, wherein said ventral spinal neuron progenitor cells are derived from induced pluripotent stem cells.

7. The method of claim 1, wherein said ventral spinal neuron progenitor cells are derived from embryonic stem cells.

8. The method of claim 1, further comprising seeding glial cells within said first microchannel.

9. The method of claim 8, wherein said glial cells comprise one or more cell types selected from the list comprising astrocytes, oligodendrocytes, ependymal cells, Schwann cells, microglia, and satellite cells.

10. The method of claim 6, wherein said induced pluripotent stem cells, prior to step a), are differentiated using a Wingless/Integrated (WNT) agonist and SMAD inhibitors to neural ectoderm.

11. The method of claim 10, wherein said neural ectoderm cells, prior to step a), are exposed to retinoic acid and sonic hedgehog agonist to pattern said ventral spinal neural progenitor cells.

12. The method of claim 1, wherein said ventral spinal neural progenitor cells were frozen, banked, and thawed before step a).

13. A method of culturing cells, comprising:
    a) providing induced pluripotent human stem cells, brain microvascular endothelial cells, and a dual microchannel microfluidic device comprising a first microchannel and second microchannel separated by a membrane;
    b) differentiating said induced pluripotent stem cells to neural ectoderm;
    c) exposing said neural ectoderm to retinoic acid and sonic hedgehog agonist to pattern ventral spinal neural progenitor cells;
    d) seeding said ventral spinal neural progenitor cells in said first microchannel on said membrane and seeding said brain microvascular endothelial cells in said second microchannel on said membrane of said microfluidic device so as to create seeded cells; and
    e) culturing said ventral spinal neural progenitor cells with a flowing culture media such that at least a portion of said patterned ventral spinal neural progenitor cells and said brain microvascular endothelial cells are in direct physical contact with each other through said membrane.

14. The method of claim 13, wherein said cultured cells express a marker selected from the group consisting of SMI32, nuclear marker islet 1 (ISL1), Beta 3 tubulin (TUBB3), NKX6.1, neurofilament marker microtubule-associated protein 2 (MAP2), and synaptic marker synaptophysin (SYNP).

15. The method of claim 13, wherein said ventral spinal neural progenitor cells were frozen, banked and thawed before step d).

16. The method of claim 13, wherein said first and second microchannels each comprise a surface that is parallel to said membrane, and each comprise side walls, wherein said first and second microfluidic microchannels comprise polydimethylsiloxane.

17. The method of claim 13, further comprising seeding glial cells within said first microchannel.

18. The method of claim 17, wherein said glial cells comprise one or more cell types selected from the list comprising astrocytes, oligodendrocytes, ependymal cells, Schwann cells, microglia, and satellite cells.

19. A method of culturing cells, comprising:
a) providing human ventral spinal neuron progenitor cells, brain microvascular endothelial cells, glial cells and a dual microchannel microfluidic device comprising a first microchannel and a second microchannel separated by a membrane;
b) seeding said human ventral spinal neuron progenitor cells and said glial cells within said first microchannel and seeding said brain microvascular endothelial cells within said second microchannel so as to create seeded cells; and
c) differentiating said seeded human ventral spinal neuron progenitor cells with a culture media flowing over said human ventral spinal neuron progenitor cells such that at least a portion of said human ventral spinal neuron progenitor cells and brain microvascular endothelial cells are in direct physical contact with each other.

20. The method of claim 19, wherein said glial cells comprise one or more cell types selected from the list comprising astrocytes, oligodendrocytes, ependymal cells, Schwann cells, microglia, and satellite cells.

\* \* \* \* \*